(12) United States Patent
Crooke

(10) Patent No.: US 7,432,249 B2
(45) Date of Patent: *Oct. 7, 2008

(54) OLIGORIBONUCLEOTIDES AND RIBONUCLEASES FOR CLEAVING RNA

(75) Inventor: Stanley T. Crooke, Carlsbad, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 606 days.

This patent is subject to a terminal disclaimer.

(21) Appl. No.: 10/281,297

(22) Filed: Oct. 25, 2002

(65) Prior Publication Data

US 2003/0119777 A1    Jun. 26, 2003

Related U.S. Application Data

(60) Division of application No. 09/479,783, filed on Jan. 7, 2000, which is a division of application No. 08/870,608, filed on Jun. 6, 1997, now Pat. No. 6,107,094, which is a continuation-in-part of application No. 08/659,440, filed on Jun. 6, 1996, now Pat. No. 5,898,031.

(51) Int. Cl.
  A61K 31/70 (2006.01)
  C07H 21/02 (2006.01)
  C07H 21/04 (2006.01)
  C12N 5/00 (2006.01)

(52) U.S. Cl. .................. 514/44; 435/6; 536/23.1; 536/24.1; 536/24.5

(58) Field of Classification Search .......... None
  See application file for complete search history.

(56) References Cited

U.S. PATENT DOCUMENTS

| | | | |
|---|---|---|---|
| 3,687,808 A | 8/1972 | Merigan et al. |
| 4,373,071 A | 2/1983 | Itakura |
| 4,401,796 A | 8/1983 | Itakura |
| 4,469,863 A | 9/1984 | Ts'o et al. |
| 4,507,433 A | 3/1985 | Miller et al. |
| 4,720,483 A | 1/1988 | Jansz et al. |
| 4,757,141 A | 7/1988 | Fung et al. |
| 4,812,512 A | 3/1989 | Buendia et al. |
| 4,908,405 A | 3/1990 | Bayer et al. |
| 5,013,830 A | 5/1991 | Ohtsuka et al. |
| 5,023,243 A | 6/1991 | Tullis |
| 5,082,934 A | 1/1992 | Saba et al. |
| 5,130,302 A | 7/1992 | Spielvogel |
| 5,142,047 A | 8/1992 | Tullis |
| 5,149,797 A | 9/1992 | Pederson et al. |
| 5,151,510 A | 9/1992 | Stec et al. |
| 5,177,198 A | 1/1993 | Spielvogel et al. |
| 5,223,618 A | 6/1993 | Cook et al. |
| 5,235,033 A | 8/1993 | Summerton et al. |
| 5,256,775 A | 10/1993 | Froehler |
| 5,264,562 A | 11/1993 | Matteucci |
| 5,264,564 A | 11/1993 | Matteucci |
| 5,359,044 A | 10/1994 | Cook et al. |
| 5,366,878 A | 11/1994 | Pederson et al. |
| 5,378,825 A | 1/1995 | Cook et al. |
| 5,386,023 A | 1/1995 | Sanghvi et al. |
| 5,391,667 A | 2/1995 | Dellinger |
| 5,403,711 A | 4/1995 | Walder et al. |
| 5,424,413 A | 6/1995 | Hogan et al. |
| 5,457,191 A | 10/1995 | Cook et al. |
| 5,459,255 A | 10/1995 | Cook et al. |
| 5,466,786 A | 11/1995 | Buhr et al. |
| 5,476,925 A | 12/1995 | Letsinger et al. |
| 5,484,908 A | 1/1996 | Froehler et al. |
| 5,489,677 A | 2/1996 | Sanghvi et al. |
| 5,506,212 A | 4/1996 | Hoke et al. |
| 5,506,337 A | 4/1996 | Summerton et al. |
| 5,506,351 A | 4/1996 | McGee |
| 5,508,270 A | 4/1996 | Baxter et al. |
| 5,514,786 A | 5/1996 | Cook et al. |
| 5,519,134 A | 5/1996 | Acevedo et al. |
| 5,539,083 A | 7/1996 | Cook et al. |
| 5,561,043 A | 10/1996 | Cantor et al. |
| 5,612,469 A * | 3/1997 | Goodchild ............. 536/23.1 |
| 5,614,617 A | 3/1997 | Cook et al. |
| 5,631,148 A | 5/1997 | Urdea |
| 5,639,873 A | 6/1997 | Barascut et al. |
| 5,719,271 A | 2/1998 | Cook et al. |
| 5,760,202 A | 6/1998 | Cook et al. |

(Continued)

FOREIGN PATENT DOCUMENTS

DE    101 00 588    7/2002

(Continued)

OTHER PUBLICATIONS

Struck, "Vaccine R&D Success Rates And Development Times," *Nature Biotechnology*, May 1996, vol. 14, pp. 591-593.

(Continued)

*Primary Examiner*—Sean R McGarry
(74) *Attorney, Agent, or Firm*—Woodcock Washburn LLP

(57) ABSTRACT

Oligomeric compounds including oligoribonucleotides and oligoribonucleosides are provided that have subsequences of 2'-pentoribofuranosyl nucleosides that activate dsRNase. The oligoribonucleotides and oligoribonucleosides can include substituent groups for increasing binding affinity to complementary nucleic acid strand as well as substituent groups for increasing nuclease resistance. The oligomeric compounds are useful for diagnostics and other research purposes, for modulating the expression of a protein in organisms, and for the diagnosis, detection and treatment of other conditions susceptible to oligonucleotide therapeutics. Also included in the invention are mammalian ribonucleases, i.e., enzymes that degrade RNA, and substrates for such ribonucleases. Such a ribonuclease is referred to herein as a dsRNase, wherein "ds" indicates the RNase's specificity for certain double-stranded RNA substrates. The artificial substrates for the dsRNases described herein are useful in preparing affinity matrices for purifying mammalian ribonuclease as well as non-degradative RNA-binding proteins.

27 Claims, 8 Drawing Sheets

U.S. PATENT DOCUMENTS

| | | | |
|---|---|---|---|
| 5,804,683 A | 9/1998 | Usman et al. | |
| 5,861,493 A | 1/1999 | Cook et al. | |
| 5,891,683 A | 4/1999 | Usman et al. | |
| 5,891,684 A | 4/1999 | Usman et al. | |
| 5,898,031 A | 4/1999 | Crooke et al. | |
| 5,955,443 A | 9/1999 | Bennett et al. | |
| 5,962,425 A | 10/1999 | Walder et al. | |
| 5,998,203 A | 12/1999 | Matulic-Adamic et al. | |
| 6,087,484 A * | 7/2000 | Goodchild | 536/23.1 |
| 6,107,094 A | 8/2000 | Crooke | |
| 6,133,246 A | 10/2000 | McKay et al. | |
| 6,210,892 B1 | 4/2001 | Bennett et al. | |
| 6,222,025 B1 | 4/2001 | Cook et al. | |
| 6,262,036 B1 | 7/2001 | Arnold, Jr. et al. | |
| 6,274,723 B1 | 8/2001 | Nilsen | |
| 6,506,559 B1 | 1/2003 | Fire et al. | |
| 6,573,072 B1 * | 6/2003 | Goodchild | 435/91.31 |
| 6,818,759 B2 | 11/2004 | Beigelman et al. | |
| 6,849,726 B2 | 2/2005 | Usman et al. | |
| 7,022,828 B2 | 4/2006 | McSwiggen | |
| 2002/0165189 A1 | 11/2002 | Crooke | |
| 2003/0096286 A1 | 5/2003 | Crooke | |
| 2003/0096287 A1 | 5/2003 | Crooke | |
| 2003/0096784 A1 | 5/2003 | Crooke | |
| 2003/0119777 A1 | 6/2003 | Crooke | |
| 2003/0125241 A1 | 7/2003 | Wissenbach et al. | |
| 2003/0139585 A1 | 7/2003 | Uhlmann et al. | |
| 2003/0143732 A1 | 7/2003 | Fosnaugh et al. | |
| 2003/0206887 A1 | 11/2003 | Morrissey et al. | |
| 2004/0029275 A1 | 2/2004 | Brown et al. | |
| 2004/0146867 A1 | 7/2004 | Slattum et al. | |
| 2005/0142535 A1 | 6/2005 | Damha et al. | |

FOREIGN PATENT DOCUMENTS

| | | |
|---|---|---|
| DE | 10100588 A1 | 7/2002 |
| EP | 0 266 168 A2 | 5/1988 |
| EP | 339842 | 11/1989 |
| JP | 2-264792 | 10/1990 |
| WO | WO92/07065 | 4/1992 |
| WO | WO92/20822 | 11/1992 |
| WO | WO92/20823 | 11/1992 |
| WO | WO92/22651 | 12/1992 |
| WO | WO 93/07883 | 4/1993 |
| WO | WO 9401550 * | 1/1994 |
| WO | WO 94/02498 A1 | 2/1994 |
| WO | WO94/02499 | 2/1994 |
| WO | WO94/02501 | 2/1994 |
| WO | WO94/17093 | 8/1994 |
| WO | WO 96/07392 A2 | 3/1996 |
| WO | 9746570 A1 | 12/1997 |
| WO | WO 97/46570 | 12/1997 |
| WO | 9932619 A1 | 7/1999 |
| WO | 0063364 A2 | 10/2000 |
| WO | WO 00/63364 | 10/2000 |
| WO | WO 02/44321 A2 | 6/2002 |
| WO | 2004097049 A1 | 11/2004 |

OTHER PUBLICATIONS

Ohtsuka et al., "Recognition By Restriction Endonuclease *Eco*RI Of Deoxyoctanucleotides Containing Modified Sugar Moieties," *J. Biochem*, 1984, vol. 139, pp. 447-450.

International Search Report Dated Aug. 23, 2004 for International Application No. PCT/US03/09808.

Arya, S. K. et al., "Inhibition of RNA Directed DNA Polymerase of Murine Leukemia Virus by 2'-O-Alkylated Polyadenylic Acids," Biochem. Biophys. Res. Commun. (1974) 59(2):608-615.

Arya, S. K. et al., "Inhibition of Synthesis of Murine Leukemia Virus in Cultured Cells by Polyribonucleotides and Their 2'-O-Alkyl Derivatives," Mol. Pharm. (1976) 12:234-241.

De Clercq, E. et al., "Influence of Various 2- and 2'- Substituted Polyadenylic acids on Murine Leukemia Virus Reverse Transcriptase," Cancer Lett. (1979) 7:27-37.

Hamilton, A. J. et al., "A Species of Small Antisense RNA in Post-transcriptional Gene Silencing in Plants," Science (1999) 286:950-952.

Hobbs, J. et al., "Polynucleotides Containing 2'-Chloro-2'-deoxyribose," Biochem. (1972) 11(23):4336-4344.

Hobbs, J. et al., "Poly 2'-Deoxy-2'-Aminouridylic Acid," Biochem. Biophys. Res. Commun. (1972) 46(4):1509-1515.

Hobbs, J. et al., "Polynucleotides Containing 2'-Amino-2'-deoxyribose and 2'-Azido-2'-deoxyribose," Biochem. (1973) 12(25):5138-5145.

Hunter, C. P., "Genetics: A touch of elegance with RNAi," Current Biology (1999) 9:R440-R442.

Kumar, M. et al., "Antisense RNA: Function and Fate of Duplex RNA in Cells of Higher Eukaryotes," Microbiol. Mol. Biol. Rev. (1998) 62(4):1415-1434.

Pieken, W. A. et al., "Kinetic Characterization of Ribonuclease-Resistant 2'-Modified Hammerhead Ribozymes," Science (1991) 253:314-317.

Pilet, J. et al., "Structural Parameters of Single and Double Stranded Helical Polyribonucleotides," Biochem. Biophys. Res. Commun. (1973) 52(2):517-523.

Rottman, F. et al., "Polynucleotides Containing 2'-O-Methyladenosine. I. Synthesis of Polynucleotide Phosphorylase," Biochem. (1968) 7(7):2634-2641.

Rottman, F. et al., "Polymers Containing 2'-O-Methylnucleotides. II. Synthesis of Heteropolymers," Biochem. (1969) 8(11):4354-4361.

Wincott, F. et al., "Synthesis, deprotection, analysis and purification of RNA and ribozymes," Nucleic Acids Res. (1995) 23(14):2677-2684.

Zmudzka, B. et al., "Poly 2'-O-methylcytidylic acid and the role of the 2'-hydroxyl in polynucleotide structure," Biochem. Biophys. Res. Commun. (1969) 37(6):895-901.

EP Supplementary Search Report for EP 03716922 dated May 12, 2006.

Hamilton et al., "A species of small antisense RNA in post-transcriptional gene silencing in plants," *Science* (1999) 286(5441):950-952.

Hunter, "Genetics: a touch of elegance with RNAi," *Current Biology, Current Science* (1999) 9(12):R440-R442.

Kumar et al., "Antisense RNA: function and fate of duplex RNA in cells of higher eukaryotes," *Microbiology and Molecular Biology Reviews* (1998) 62(4):1415-1434.

Hunziker et al., Nucleic Acid Analogues: Synthesis and Properties in Modern Synthetic Methods, ed., Ernst and Leumann, pp. 331-417 (1995).

Opalinska et al., "Nucleic-acid therapeutics: basic principles and recent applications," *Nature Reviews* (2002) 1:503-514.

Milligan et al., "Current concepts in antisense drug design,"*J of Medicinal Chemistry* (1993) 36(1):1923-1927.

Ausubel, et al., Eds., Current Protocols in Molecular Biology, 1988, Wiley & Sons, New York.

Beaucage S. and Iyer, R., "Advances in the synthesis of oligonucleotides by the phosphoramidite approach", *Tetrahedron Letters*, 1992, 48, 2223-2311.

Beaucage S. and Iyer, R., "The synthesis of modified oligonucleotides by the phosphoramidite approach and their applications", *Tetrahedron*, 1993, 49, 6123-6194.

Bhat, et al., "A Simple and Convenient Method for the Selective N-Acylations of Cytosine Nucleosides", *Nucleosides and Nucleotides*, 1989, 8, 179-183.

Crooke, S.T. and Bennett, C.F., "Progress in Antisense Oligonucleotide Therapeutics", *Annu. Rev. Pharmacol. Toxicol.*, 1996, 36, 107-129.

Crooke, et al., "Kinetic characteristics of *Escherichia coli* RNase Hl: cleavage of various antisense oligonucleotide-RNA duplexes", *Biochem. J.*, 1995, 312, 599-608.

Dagle, et al., "Targeted degradation of mRNA in Xenopus oocytes and embryos directed by modified oligonucleotides: studies of An2 and cyclin in embryogenesis", *Nucleic Acids Research*, 1990, 18, 4751-4757.

Dagle, et al., "Pathways of Degradation and Mechanism of Action of Antisense Oligonucleotides in *Xenopus laevis* Embryos", *Antisense Res. And Dev.*, 1991, 1, 11-20.

Dagle, et al., "Physical properties of oligonucleotides containing phosphoramidate-modified internucleoside linkages", *Nucleic Acids Research*, 1991, 19, 1805-1810.

Englisch, U. And Gauss, D.H., "Chemically Modified Oligonucleotides as Probes and Inhibitors", *Angewandt Chemie, International Edition Engl.*, 1991, 30, 613-629.

Haeuptle and Dobberstein, "Translation arrest by oligonucleotides complementary to mRNA coding sequences yields polypeptides of predetermined length", *Nucleic Acids Res.*, 1986, 14, 1427-1448.

Eder, P.S. and Walder, J.A., "Ribonuclease H from K562 Human Erythroleukemia Cells", *J. Biol. Chem.*, 1991, 266, 6472-6479.

Kawasaki, et al., "Uniformly Modified 2'-Deoxy-2'-fluoro Phosphorothioate Oligonucleotides as Nuclease-Resistant Antisense Compounds with High Affinity and Specificity for RNA Targets", *J. Med. Chem.*, 1993, 36, 831-841.

Kawasaki, et al., "Synthesis and Biophysical Studies of 2'-dRIBO-2'-F Modified Oligonucleotides", Conf. on Nucleic Acid Therapeutics, Clearwater, FL, Jan. 13-16, 1991, 10 pages.

Martin, "Ein neuer Zugang zu 2'-O-Alkylribonucleosiden und Eigenschaften deren Oligonucleotide", *Helv. Chim. Acta.*, 1995, 78, 486-504.

Monia, et al., "Selective Inhibition of Mutant Ha-ras mRNA Expression by Antisense Oligonucleotides", *J. Biol. Chem.*, 1992, 267, 19954-19962.

Monia, et al., "Evaluation of 2'-Modified Oligonucleotides Containing 2'-Deoxy Gaps as Antisense Inhibitors of Gene Expression", *J. Biol. Chem.*, 1993, 268, 14514-14522.

Reese, C.B., et al., "4-(1,2,4-Triazol-1-yl)-and 4-(3-Nitro-1,2,4-triazol-1-yl)-1-(β-D-Arabinofuranosyl)cytosine(Ara-C)", *J. Chem. Soc. Perkin Trans. 1*, 1982, pp. 1171-1176.

Robins, et al., "Nucleic acid related compounds. 41. Restricted furanose conformations of 3',5'-O(1,1,3,3-tetraisoprpyldisilox-1,3-diyl)nucleosides provide a convenient evaluation of anomeric configuration[1,2]", *Can. J. Chem.*, 1983, 61, 1911-1920.

Saison-Behmoaras, T., et al., "Short modified antisense oligonucleotides directed against Ha-ras point mutation induce selective cleavage of the mRNA and inhibit T24 cells proliferation", *EMBO*, 1991, 10, 1111-1118.

Concise Encyclopedia of Polymer Science and Engineering, pp. 858-859, Kroschwitz, J.I., Ed., John Wiley & Sons, 1990.

Oligonucleotide Synthesis, A Practical Approach, M.J. Gait, Ed., IRL Press, 1984.

Oligonucleotide and Analogs, A Practical Approach, F. Eckstein, Ed., IRL Press, 1991, Chapters 1-7.

De Mesmeker, et al., "Antisense Oligonucleotides", *Acc. Chem. Res.*, 1995, 28, 366-374.

Goodchild, et al., "Conjugates of Oligonucleotides and Modified Oligonucleotides: A Review of their Synthesis and Properties", *Bioconjugate Chem.*, 1990, 1(3), 165-187.

Menelev, et al., *Bioorg. & Med. Chem. Lett.*, 1994, 4(24), 2929-2934.

Lengyel, *J. Enzym. Res.*, 1987, 7, 511-519.

Milligan, *J. Med. Chem.*, 1993, 36, 1923.

Tseng, et al., "Antisense Oligonucleotide Technology in the Development of Cancer Therapeutics", *Cancer Gene Therapeutics*, 1994, 1, 65-71.

Westermann, et al., "Inhibition of expression of SV40 virus large T-antigen by antisense oligodeoxyribonucleotides", *Biomed. B. Acta.*, 1989, 48, 85-93.

Stein, C.A. et al., "Antisense Oligonucleotides as Therapeutic Agents—Is the Bullet Really Magical?", *Science*, 1993, 261, 1004-1012.

Stull, et al., "Antigene, Ribozyme and Aptamer Nucleic Acid Drugs: Progress and Prospects", *Pharm. Res.*, 1995, *Pharm. Rev.*, 12, 465-482.

Uhlmann, et al., "Antisense Oligonucleotides: A New Therapeutic Principle", *Chem. Rev.*, 1990, 90, 543.

Sands, et al., "Biodistribution and Metabolism of Internally [3]H-Labeled Olionucleotides. II. 3',5'-Blocked Oligonucleotides", *Am. Soc. Pharmacol. Exp. Ther.*, 1995, 47, 636-646.

Strickland, et al., "Antisense RNA Directed Against the 3' Noncoding Region Prevents Dormant mRNA Activation in Mouse Oocytes", *Science*, 1988, 241, 680-684.

Akashi, et al., "Novel Stationary Phases for Affinity Chromatography. Nucleobase-Selective Recognition of Nucleosides and Nucleotides on Poly(9-vinyladenine)-Supported Silica Gel[1])'", *Chem. Letters*, 1988, 1093-1096.

Alberts, et al., "DNA-Cellulose Chromatography", *Meth. Enzymol.*, 1971, 21, 198-217.

Arndt-Jovin, et al., "Covalent Attachment of DNA to Agarose", *Eur. J. Biochem.*, 1975, 54, 411-418.

Blanks, et al., "An oligodeoxynucleotide affinity column for the isolation of sequence specific DNA binding proteins", *Nucleic Acids Res.*, 1988, 16, 10283-10299.

Blomberg, P., "Control of replication of plasmid R1: the duplex between the antisense RNA, CopA, and its target, CopT, is processed specifically in vivo and in vitro by Rnase III", *EMBO J.*, 1990, 9, 2331-2340.

Bunemann, et al., Immobilization of denatured DNA to macroporous supports: I. Efficiency of different coupling procedures, *Nucleic Acids Res.*, 1982, 10, 7163-7180.

Bunemann, H., "Immobilization of denatured DNA to macroporous supports: II. Steric and kinetic parameters of heterogeneous hybridization reactions", *Nucleic Acids Res.*, 1982, 10, 7181-7196.

Chodosh, et al., "A Single Polypeptide Possesses the Binding and Transcription Activities of the Adenovirus Major Late Transcription Factor", *Mol. Cell. Biol.*, 1986, 6, 4723-4733.

Crooke, et al., "Phmarmacokinetic Properties of Several Novel Oligonucleotide Analogs in mice", *J. Pharmacol. Exp. Therm.*, 1996, 277, 923-927.

Dake, et al., "Purification and Properties of the Major Nuclease from Mitochondria of *Saccharomyces cerevisiae*", *J. Biol. Chem.*, 1988, 263, 7691-7702.

Day, et al., "Immobilization of polynucleotides on magnetic particles", *Biochem. J.*, 1991, 278, 735-740.

Drmanac, et al., "DNA Sequence Determination by Hybridization: A Strategy for Efficient Large-Scale Sequencing", *Science*, 1993, 260, 1649-1652.

Duncan, et al., "Affinity Chromatography of a Sequence-Specific DNA Binding Protein Using Teflon-Linked Oligonucleotides", *Anal. Biochem.*, 1988, 169, 104-108.

Dunn, J.J. and Studier, F.W., "Effect of RNAase III Cleavage on Translation of Bacteriophage T7 Messenger RNAs", *J. Mol. Biol.*, 1975, 99, 487-499.

Fahy, et al., "Design and synthesis of polyacrylamide-based oligonucleotide supports for use in nucleic acid diagnostics", *Nucl. Acids Res.*, 1993, 21, 1819-1826.

Fishel, et al., "Z-DNA Affinity Chromatography", *Methods Enzymol.*, 1990, 184, 328-342.

Fodor, et al., "Light-Directed, Spatially Addressable Parallel Chemical Synthesis", *Science*, 1991, 251, 767-773.

Fusi, et al., "Ribonucleases from the extreme thermophilic archaebacterium, S. Solfataricus", *Eur. J. Biochem.*, 1993, 16, 305-310.

Gabrielsen, et al., "Magnetic DNA affinity purification of yeast transcription factor τ—a new purification principle for the ultrarapid isolation of near homogeneous factor", *Nucleic Acids Research*, 1989, 17, 6253-6267.

Gbenle, "*Trypanosoma brucei*: Calcium-Dependent Endoribonuclease is Associated with Inhibitor Protein",, *Exp. Parasitol.*, 1990, 71, 432-438.

Gbenle, "Simultaneous Isolation of Cytoplasmic Endoribonuclease and Exoribonucease of *Trypanosoma brucei*", *Mol. Biochem. Parasitol.*, 1985, 15, 37-47.

Gerdes, K., et al., "Mechanism of Killer Gene Activation. Antisense RNA-dependent Rnase III Cleavage Ensures Rapid Turn-over of the Stable-Hok, SrnB and PndA Effector Messenger RNAs", *J. Mol. Biol.*, 1992, 226, 637-649.

Gingeras, et al., "Hybridization properties of immobilized nucleic acids", *Nucl. Acids Res.*, 1987, 15, 5373-5391.

Goldkorn, T. And Prockop, D.J., "A simple and efficient enzymatic method for covalent attachment of DNA to cellulose. Application for hybridization-restriction analysis and for in vitro synthesis of DNA probes", *Nucleic Acids Res.*, 1986, 14, 9171-9191.

Goss, T.A. and Bard, M., "High-performance affinity chromatography of DNA", *J. Chromatogr.*, 1990, 508, 279-287.

Guo, et al., "Direct fluorescence analysis of genetic polymorphisms by hybridization with oligonucleotide arrays on glass supports", Nucl. Acids Res., 1994, 22, 5456-5465.

Kadonaga, J.T. and Tjian, R., "Affinity purification of sequence-specific DNA binding proteins", *Proc. Natl. Acad. Sci. USA*, 1986, 83, 5889-5893.

Kadonaga, J.T., "Purification of Sequence-Specific Binding Proteins b DNA Affinity Chromatography", *Methods in Enzymology*, 1991, 208, 10-23.

Kasher, et al., "Rapid Enrichment of HeLa Trancription Factors IIIB and IIIC by Using Affinity Chromatography Based on Avidin-Biotin Interactions", *Mol. And Cell. Biol.*, 1986, 6, 3117-3127.

Kawaguchi, et al., "Purification of DNA-binding transcription factors by their selective adsorption of the affinity atex particles", *Nucleic Acids Research*, 1989, 17, 6229-6240.

Kennedy, "Hydrophobic Chromatography", *Methods in Enzymology*, 1990, 182, 339-343.

Knecht, D., "Application of Antisense RNA to the Study of the Cytoskeleton: Background, Principles, and a Summary of Results Obtained with Myosin Heavy Chain", *Cell Motil. and Cytoskel.*, 1989, 14, 92-102.

Knochbin and Lawrence, "An antisense RNA involved in p53 mRNA maturation in murine erythroleukemia cells induced to differentiate", *EMBO J.*, 1989, 8, 4107-4114.

Krinke, L. And Wulff, D., "RNase III-dependent hybrolysis of λcII-O gene mRNA mediated by λ OOP antisense RNA", *Genes & Devel.*, 1990, 4, 2223-2233.

Krystal, et al., "N-*myc* mRNA Forms an RNA-RNA Duplex with Endogenous Antisense Transcripts", *Mol. And Cell. Biol.*, 1990, 10, 4180-4191.

Liao, "A pyrimidine-guanine sequence-specific ribonuclease from *Rana catesbeiana* (bullfrog) oocytes", *Nucl. Acids Res.*, 1992, 20, 1371-1377.

Lohrmann, et al., "New Solid Supports for DNA Synthesis" *DNA*, 1984, 3, 122.

Lund, et al., "Assessment of methods for covalent binding of nucleic acids to magnetic beads, Dynabeads™, and the characteristics of the bound nucleic acids in hybridization reactions", *Nucl. Acids Res.*, 1988, 16, 10861-10880.

Maniak, M. And Nellen, W., "Evidence for a feedback regulated back-up promoter which controls permanent expression of a *Dictyostelium* gene", *Nucl. Acids Res.*, 1990, 18, 5375-5380.

Matson, et al., "Biopolymer Synthesis on Polypropylene Supports", *Anal. Biochem.*, 1994, 217, 306-310.

Maskos, U. And Southern, E.M., "Oligonucleotide hybridisations on glass supports: a novel linker for oligonucleotide synthesis and hybridisation properties of oligonucleotides synthesised in situ", *Nucl. Acids. Res.*, 1992, 20, 1679-1684.

Meegan, J.M. and Marcus, P.I., "Double-Stranded Ribonuclease Coinduced with Interferon", *Science*, 1989, 244, 1089-1091.

Narhi, et al., "Hydrophobic Interaction Chromatography in Alkaline pH", *Anal. Biochem.*, 1989, 182, 266-270.

Nellen, W., C., "What makes an mRNA anti-sense-itive?", *Curr. Opin. Cell. Biol.*, 1993, 18, 419-424.

Nellen, W., et al., "Mechanisms of gene regulation by endogenous and artificially introduced antisense RNA", *Biochem., Soc. Trans.*, 1992, 20, 750-754.

Nitta, et al., "Purification and Some Properties of Ribonuclease from *Xenopus laevis* Eggs", *Biol. Pharm. Bull.* (Jpn.), 1993, 16, 353-356.

Noguchi, et al., "Characterization of an Antisense Inr Element in the eIF-2α Gene", *J. Biol. Chem.*, 1994, 269, 29161-29167.

Noyes, et al., "Nucleic Acid Hybridization Using DNA Covalently Coupled to Cellulose", *Cell*, 1975, 5, 301-310.

Pease, et al., "Light-generated oligonucleotide arrays for rapid DNA sequence analysis",*Proc. Natl. Acad. Sci. USA*, 1994, 91, 5022-5026.

Pon, et al., "Derivatization of Controlled Pore Glass Beads for Solid Phase Oligonucleotide Synthesis", *BioTech.*, 1988, 6, 768-773.

Prokipcak, et al., "Purification and Properties of a Protein that Binds to the C-terminal Coding Region of Human c-myc mRNA", *J. Biol. Chem.*, 1994, 269, 9261-2969.

Saito, H. And Richardson, C., "Processing of mRNA by Ribonuclease III Regulates Expression of Gene 1.2 of Bacteriophage T7", 1981, *Cell*, 27, 533-542.

Schott, "Template-Chromatographie An Stationar Gebundenen Oligonukleotiden", *J. Chromatogr.*, 1975, 115, 461-476.

Seliger, H., "Handelsubliche Polymere als Trager in der Oligonucleotidsynthese, 1", *Die Makromolekulart Chemie*, 1975, 176, 1611-1627.

Seliger, H., and Aumann, G., "Trager-Oigonucleotidsynthese an unvernetzten Copolymeren aus Vinylalkohol und N-Vinylpyrrolidon", *Die Makromolekulare Chemie.*, 1975, 176, 609-627.

Seliger,H. And Aumann, G., "Oligonucleotide Synthesis on a Polymer Support Soluble in Water and Pyridine", *Tetrahedron Letters*, 1973, No. 31, 2911-2914.

Siddell, S.G., "RNA Hybridization to DNA Coupled with Cyanogen-Bromide-Activated Sephadex", *Eur. J. Biochem.*, 1978, 92, 621-629.

Smith, et al., "The synthesis of oigonucleotides containing an aliphatic amino group at the 5' terminus: synthesis of fluorescent DNA primers for use in DNA sequence analysis", *Nucl. Acids Res.*, 1985, 13, 2399-2412.

Stoldt, P. And Zillig, W., "Antisense RNA mediates transcriptional procesing in an archaebacterium, indicating a novel kind of RNase activity", *Mol. Microbiol.*, 1993, 7, 875-882.

Syvanen, et al., "Quantification of polymerase chain reaction products by affinity-based hybrid collection", *Nucl. Acids Res.*, 1988, 16, 11327-11338.

Szyf, et al., "Growth Regulation of Mouse DNA Methyltransferase Gene Expression", *J. Biol. Chem.*, 1991, 266, 10027-10030.

McBride, L.J. and Caruthers, M.H., "An Investigation of Several Deoxynucleoside Phosphoramidites Useful for Synthesizing Deoxyoligonucleotides", *Tetrahedron Letters*, 1983, 24, 245-248.

Van Ness, et al., "A versatile solid support system for oligodeoxynucleotide probe-based hybridization assays", *Nucleic Acids Research*, 1991, 19, 3345-3350.

Volk, et al., "An antisense transcript from the *Xenopus laevis* bFGF gene coding for an evolutionariy conserved 24 kd protein", *EMBO J.*, 1989, 8, 2983-2988.

Wetlaufer, et al., "Surfactant-Mediated Protein Hydrophobic-Interaction Chromatography", *J. Chromatography*, 1986, 359, 55-60.

Wu, et al., "Purification and Properties of *Drosophila* Heat Shock Activator Protein", *Science*, 1987, 238, 1247-1253.

Wu, et al., "High Resolution Separation and Analysis of Biological Macromolecules", *Methods in Enzymology*, 1996, 270, 27-47.

Yashima, et al., "High-performance affinity chromatography of oligonucleotides on nucleic acid analogue immobilized silica gel columns", *J. Chromatog.*, 1992, 603, 111-119.

Yasuda, et al., "Purification and characterization of a ribonuclease from human spleen", *Eur. J. Biochem.*, 1990, 191, 523-529.

Zarytova, et al., "Affinity Chromatography of DNA Fragments and P-Modified Oligonucleotides", *Analyt. Biochem.*, 1990, 188, 214-218.

Zuckermann, et al., "Efficient methods for attachment of thiol specific probes to the 3'-ends of synthetic oligodeoxyribonucleotides", *Nucleic Acids Research*, 1987, 15, 5305-5321.

Hyrup, B. And Nielsen, P., "Peptide Nucleic Acids (PNA): Synthesis, Properties and Potential Applications", *Bioorganic & Med. Chem*, 1996, 4, 5-23.

Branch, A., "A Good Antisense is Hard to Find," TIBS (1998) 23:45-50.

Agarwal, S., "Antisense Oligonucleotides: Towards Clinical Trials," TIBTECH (1996) 14:376-388.

Elela, et al., "RNase III Cleaves Eukaryotic Periribosomal RNA at a U3 snoRNP-Dependent Site," Cell (1996) 85:115-124.

Goodchild, et al., "Conjugates of oligonucleotides and modified oligonucleotides: a review of their synthesis and properties," Bioconjugate Chem. (1990) 1:165-187.

Metelev, et al, "Study of antisense oligonucleotide phosphorothioates containing segments of oligodeoxynucleotides and 2'-methyloligoribonucleotides," Bioorg. Med. Chem. Lett. (1994) 4:2929-2934.

Monia, et al., "Antitumor activity of a phosphorothioate antisense oligodeoxynucleotide targeted against c-raf kinase," Nuc. Med. (1996) 2:668-675.

Ohtsuki, et al., "Isolation and purification of double-stranded ribonuclease from calf thymus," J. Biol. Chem. (1977) 252:483-491.

Strickland, et al., "Antisense RNA directed against the 3' noncoding region prevents dormant mRNA activation in mouse oocytes," Science (1988) 241:680-684.

Agarwal, et al., "Synthesis and Anti-HIV Activity of Oligoribonucleotides and Their Phosphorothioate Analogs," Ann. N.Y. Acad. Sci. (1992) 2-10.

Shibihara, et al., "Inhibition of human immunodeficiency virus (HIV-1) replication by synthetic oligo-RNA derivatives," Nucleic Acids Res. (1989) 17(1):239-152.

Alahari, *J. Pharmacology and Experimental Therapeutics*, 1998, 286, 419-428.

Beigelman, *J. Biol Chem*, 1995, 270, 25702-25708.

Berger, *Nucleic Acids Research*, 1998, 26, 2473-2480.

Bevilacqua, *Biochemistry*, 1996, 35, 9983-9994.

Boutla, *Current Biology*, 2001, 11, 1776-1780.

Cook, *Anti-Cancer Drug Design*, 1991, 6, 585-607.

Damha, *J. Am. Chem. Soc.*, 120:12976-12977.

Elbashir, *Embo J.*, 2001, 20, 6877-6888.

Hammond, *Nature*, 200, 2, 110-119.

Kimura-Harada, *FEBS Lett.*, 1971, 13, 335-338;.

Koizumi, *Nucleic Acids Research*, 1989, 17, 7059-7071.

Kuimelis, *Nucleic Acids Res*. 1994,22, 1429-1436.

Lesnik, *Biochemistry*, 1995, 34,10807-10815.

Parrish, *Molecular Cell*, 2000, 6, 1077-1087.

Porta, *Biotechnology*, 1995, 13, 161-164.

Shuman, *J. Biol Chem*, 1993, 268, 18943-18950.

Tosquellas, *Nucleic Acids Research*, 1998, 26, 2069-2074.

Tracewell, *Toxicology and Applied Pharmacology*, 1995, 135, 179-184.

Tudchl, *Molecular Interventions*, 2002, 2, 158-167.

Veronese, II Farmaco, 1999, 54, 497-516.

Wilds, *Nucleic Acids Res.*, 2000, 28, 3625-3635.

Wu, *J. Biol. Chem*, 1998, 273, 2532-2542.

Yu, *RNA*, 1997, 324-331.

Yu, *Bioorganic and Medicinal Chemistry*, 1996, 4, 1685-1692.

* cited by examiner

FIGURE 1

H-RAS TARGETED ANTISENSE OLIGOS:

| | | |
|---|---|---|
| FULL 2' methoxy | C C A C A C C G A C G G C G C C C | (SEQ ID NO: 2) |
| 3 BASE RNA GAP | ☐☐☐☐☐☐☐●●●☐☐☐☐☐☐☐ | |
| 5 BASE RNA GAP | ☐☐☐☐☐☐●●●●●☐☐☐☐☐☐ | |
| 7 BASE RNA GAP | ☐☐☐☐☐●●●●●●●☐☐☐☐☐ | |
| 9 BASE RNA GAP | ☐☐☐☐●●●●●●●●●☐☐☐☐ | |
| FULL RNA | ●●●●●●●●●●●●●●●●● | |

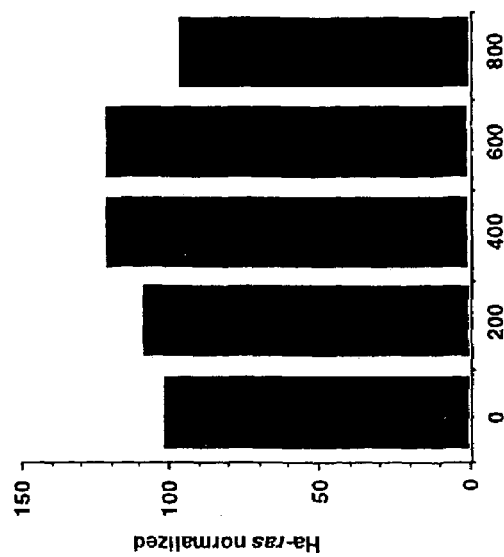
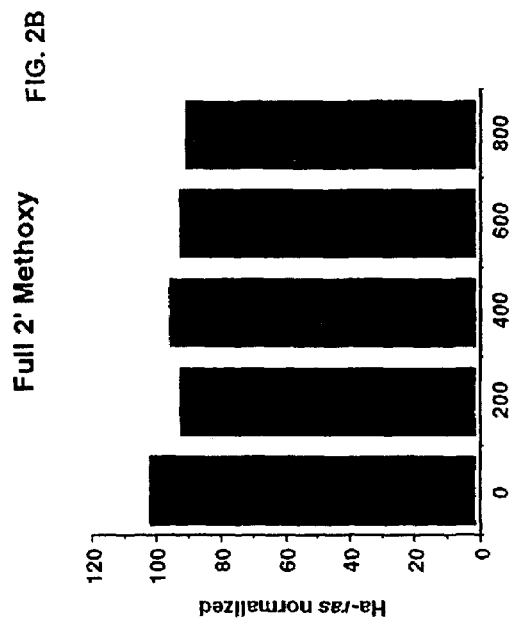
FIG. 2A
FIG. 2B
FIG. 2C
FIG. 2D

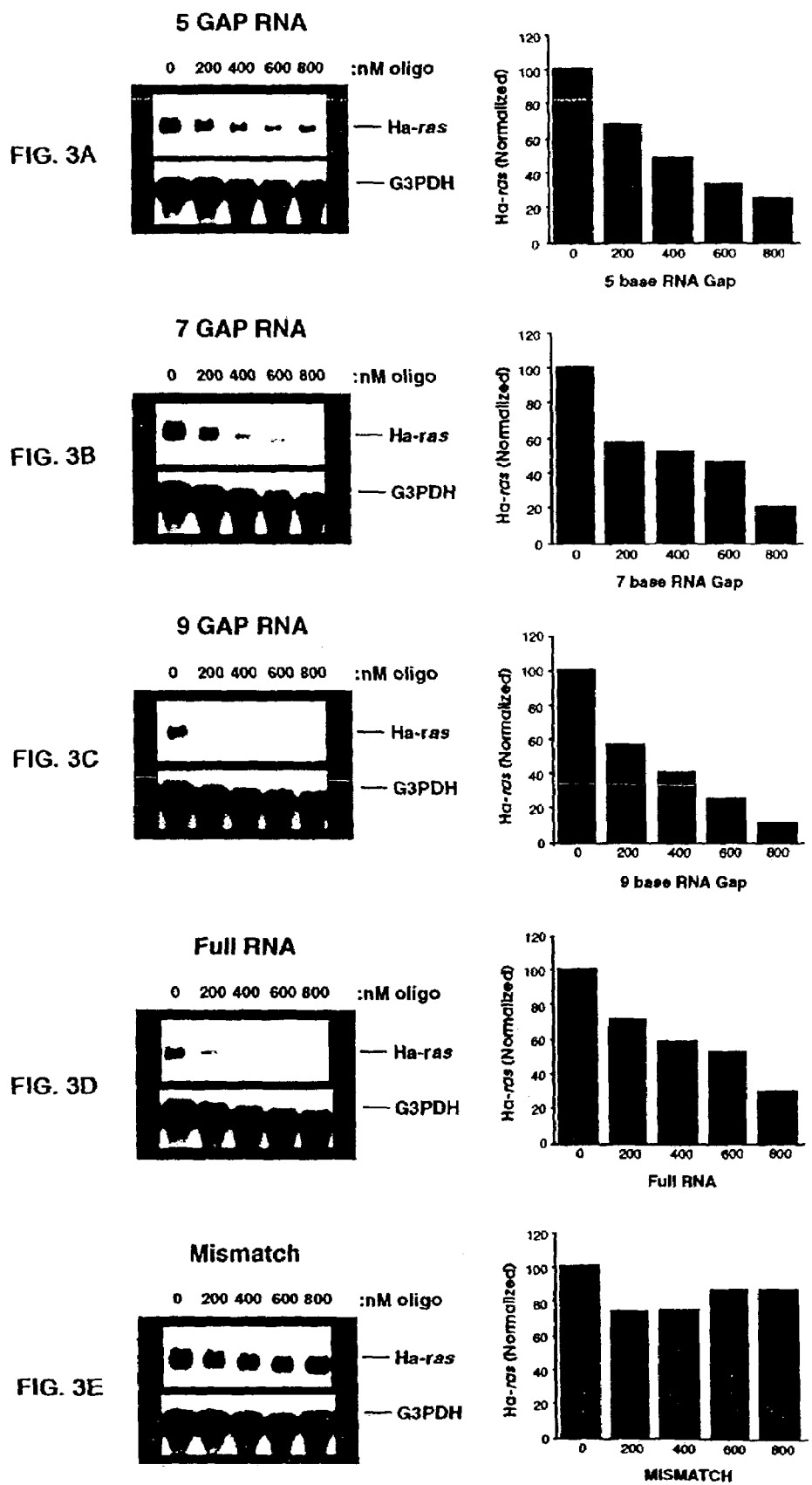

OLIGORIBONUCLEOTIDES AND RIBONUCLEASES FOR CLEAVING RNA

CROSS REFERENCED TO RELATED APPLICATIONS

This application is a divisional application of Ser. No. 09/479,783 filed Jan. 7, 2000, which is a divisional of Ser. No. 08/870,608 filed Jun. 6, 1997, now U.S. Pat. No. 6,107,094 which is a continuation-in-Part of Ser. No. 08/659,440 filed Jun. 6, 1996 now U.S. Pat. No. 5,898,031.

FIELD OF THE INVENTION

This invention is directed to the synthesis and use of oligomeric compounds, including oligoribonucleotides and oligoribonucleosides, useful for strand cleavage of target RNA strands. Included in the invention are oligoribonucleotides having modified sugars, bases or phosphate backbones and oligoribonucleosides having standard sugars and bases or modified sugars and bases linked together via non-phosphate backbones. Further included in the invention are chimeric oligoribonucleotides and oligoribonucleosides having mixed backbones, either phosphate or non-phosphate. Also included in the invention are mammalian ribonucleases, i.e., enzymes that degrade RNA. Such a ribonuclease is referred to herein as a dsRNase, wherein "ds" indicates the RNase's specificity for certain double-stranded RNA substrates. The oligoribonucleotides, oligoribonucleosides, ribonucleases and ribonuclease substrates of the invention are useful for therapeutics, diagnostics and as research reagents.

Several publications describe the interaction of Rnase H and oligonucleotides. A recently publication is: Crooke, et. al., *Biochem. J.,* 1995, 312, 599-608. Other earlier papers are: (1) Dagle et al., *Nucleic Acids Research,* 1990, 18, 4751; (2) Dagle et al., *Antisense Research And Development,* 1991, 1, 11; (3) Eder et al., *J. Biol. Chem.,* 1991, 266, 6472; and (4) Dagle et al., *Nucleic Acids Research,* 1991, 19, 1805. According to these publications, DNA oligonucleotides having both unmodified phosphodiester internucleoside linkages and modified phosphorothioate internucleoside linkages are substrates for cellular RNase H. Since they are substrates, they activate the cleavage of target RNA by RNase H. However, these authors further noted that in Xenopus embryos, both phosphodiester linkages and phosphorothioate linkages are also subject to exonuclease degradation. Nuclease degradation is detrimental since it rapidly depletes the oligonucleotide.

As described in references (1), (2) and (4), to stabilize oligonucleotides against nuclease degradation while still providing for RNase H activation, 2'-deoxy oligonucleotides having a short section of phosphodiester linked nucleosides positioned between sections of phosphoramidate, alkyl phosphonate or phosphotriester linkages were constructed. While the phosphoramidate-containing oligonucleotides were stabilized against exonucleases, in reference (4) the authors noted that each phosphoramidate linkage resulted in a loss of 1.6° C. in the measured $T_m$ value of the phosphoramidate-containing oligonucleotides. Such a decrease in the $T_m$ value is indicative of a decrease in hybridization between the oligonucleotide and its target strand.

Other authors have commented on the effect such a loss of hybridization between an oligonucleotide and its target strand can have. Saison-Behmoaras et al. (*EMBO Journal,* 1991, 10, 1111) observed that even though an oligonucleotide could be a substrate for Rnase H, cleavage efficiency by Rnase H was low because of weak hybridization to the MRNA. The authors

BACKGROUND OF THE INVENTION

Oligonucleotides are known to hybridize to single-stranded DNA or RNA molecules. Hybridization is the sequence-specific base pair hydrogen bonding of nucleobases of the oligonucleotides to nucleobases of target DNA or RNA. Such nucleobase pairs are said to be complementary to one another.

The complementarity of oligonucleotides has been used for inhibition of a number of cellular targets. Such complementary oligonucleotides are commonly described as being antisense oligonucleotides. Various reviews describing the results of these studies have been published including Progress In Antisense Oligonucleotide Therapeutics, Crooke, S. T. and Bennett, C. F., *Annu. Rev. Pharmacol. Toxicol.,* 1996, 36, 107-129. These oligonucleotides have proven to be very powerful research tools and diagnostic agents. Further, certain oligonucleotides that have been shown to be efficacious are currently in human clinical trials.

To date most oligonucleotides studied have been oligodeoxynucleotides. Antisense oligodeoxynucleotides are believed to cause a reduction in target RNA levels principally through the action of RNase H, an endonuclease that cleaves the RNA strand of DNA:RNA duplexes. This enzyme, thought to play a role in DNA replication, has been shown to be capable of cleaving the RNA component of the DNA:RNA duplexes in cell free systems as well as in *Xenopus oocytes*. Rnase H is very sensitive to structural alterations in antisense oligonucleotides. This sensitivity is such that prior attempts to increase the potency of oligonucleotides by increasing affinity, stability, lipophilicity and other characteristics by chemical modifications of the oligonucleotide have often resulted in oligonucleotides that are no longer substrates for Rnase H. In addition, Rnase H activity is quite variable. Thus a given disease state may not be a candidate for antisense therapy only because the target tissue has insufficient Rnase H activity. Therefore it is clear that effective terminating mechanisms in addition to Rnase H are of great value to the development of therapeutic and other agents. also noted that the inclusion of an acridine substitution at the 3' end of the oligonucleotide protected the oligonucleotide from exonucleases.

U.S. Pat. No. 5,013,830, issued May 7, 1991, discloses mixed oligomers comprising an RNA oligomer, or a derivative thereof, conjugated to a DNA oligomer via a phosphodiester linkage. The RNA oligomers also bear 2'-O-alkyl substituents. However, being phosphodiesters, the oligomers are susceptible to nuclease cleavage.

European Patent application 339,842, published Nov. 2, 1989, discloses 2'-O-substituted phosphorothioate oligonucleotides, including 2'-O-methylribooligonucleotide phosphorothioate derivatives. The above-mentioned application also discloses 2'-O-methyl phosphodiester oligonucleotides which lack nuclease resistance.

U.S. Pat. No. 5,149,797, issued Sep. 22, 1992, discloses mixed phosphate backbone oligonucleotides which include an internal portion of deoxynucleotides linked by phosphodiester linkages, and flanked on each side by a portion of modified DNA or RNA sequences. The flanking sequences include methyl phosphonate, phosphoromorpholidate, phosphoropiperazidate or phosphoramidate linkages.

U.S. Pat. No. 5,256,775, issued Oct. 26, 1993, describes mixed oligonucleotides that incorporate phosphoramidate linkages and phosphorothioate or phosphorodithioate linkages.

U.S. Pat. No. 5,403,711, issued Apr. 4, 1995, describes RNA:DNA probes targeted to DNA. The probes are labeled and are used in a system that includes RNase H. The RNase H enzyme cleaves those probes that bind to DNA targets. The probes can include modified phosphate groups. Mentioned are phosphotriester, hydrogen phosphonates, alkyl or aryl phosphonates, alkyl or aryl phosphoramidates, phosphorothioates or phosphoroselenates.

In contrast to the pharmacological inhibition of gene expression via the RNase H enzyme, it is becoming clear that organisms from bacteria to humans use endogenous antisense RNA transcripts to alter the stability of some target mRNAS and regulate gene expression, see Nellen, W., and Lichtenstein, C., *Curr. Opin. Cell. Biol.*, 1993, 18, 419-424 and Nellen, W., et al, *Biochem. Soc. Trans.* 1992, 20, 750-754. Perhaps one of the best examples comes from certain bacteria where an antisense RNA regulates the expression of mok MRNA, which is required for the translation of the cytotoxic hok protein. Thus as the antisense level drops, mok mRNA levels and consequently hok protein levels rise and the cells die, see Gerdes, K. et al., *J. Mol. Biol.*, 1992, 226, 637-649. Other systems regulated by such mechanisms in bacteria include the RNA I-RNA II hybrid of the ColE1 plasmid, see Haeuptle, M. T., Frank, R., and Dobberstein, B., *Nucleic Acids Res.* 1986, 14, 1427, Knecht, D., *Cell Motil. Cytoskel.*, 1989, 14, 92-102; and Maniak, M., and Nellen, W., *Nucleic Acids Res.*, 1990, 18, 5375-5380; OOP-cII RNA regulation in bacteriophage Lambda, see Krinke, L., and Wulff, D. L. (1990) *Genes Dev.*, 1990, 4, 2223-2233; and the copA-copT hybrids in *E. coli*. See Blomberg, P., Wagner, E. G., and Nordstrom, K., *EMBO J.*, 1990, 9, 2331-2340. In *E. coli* the RNA:RNA duplexes formed have been shown to be substrates for regulated degradation by the endoribonuclease RNase III. Duplex dependent degradation has also been observed in the archaebacterium, *Halobacterium salinarium*, where the antisense transcript reduces expression of the early (T1) transcript of the phage gene phiH, see Stolt, P., and Zillig, W., *Mol. Microbiol.*, 1993, 7, 875-882. In several eukaryotic organisms endogenous antisense transcripts have also been observed. These include p53, see Khochbin and Lawrence, *EMBO*, 1989, 8, 4107-4114; basic fibroblast growth factor, see Volk et al, *EMBO*, 1989, 8, 69, 2983-2988; N-myc, see Krystal, G. W., Armstrong, B. C., and Battey, J. F., *Mol. Cell. Biol.*, 1990, 10, 4180-4191; eIF-2α, see Noguchi et al., *J. Biol. Chem.*, 1994, 269, 29161-29167. The conservation of endogenously expressed antisense transcripts across evolutionary lines suggests that their biological roles and molecular mechanisms of action may be similar.

In bacteria, RNase III is the double stranded endoribonuclease (dsRNase) activity responsible for the degradation of some antisense:sense RNA duplexes. RNase III carries out site-specific cleavage of dsRNA-containing structures, see Saito, H. and Richardson, C. C., *Cell*, 1981, 27, 533-540. The RNase III also plays an important role in mRNA processing and in the processing of rRNA precursors into 16S, 23S and 5S ribosomal RNAs, see Dunn, J. J. and Studier, F. W. *J. Mol. Biol.*, 1975, 99, 487. In eukaryotes, a yeast gene (RNT1) has recently been cloned that codes for a protein that has homology to *E. coli* RNase III and shows dsRNase activity in ribosomal RNA processing, see Elela, S. A., Igel, H. and Ares, M. *Cell,* 1996, 85, 115-124. Avian cells treated with interferon produce and secrete a soluble nuclease capable of degrading dsRNA, see Meegan, J. and Marcus, P. I., *Science*, 1989, 244, 1089-1091. However such a secreted dsRNA activity is not a likely candidate to be involved in cytoplasmic degradation of antisense:sense RNA duplexes. Despite these findings almost nothing is known about human or mammalian dsRNAse activities. While it has been recognized that regulation (via any mechanism) of a target RNA strand would be useful, to date only two mechanisms for eliciting such an effect are known. These are hybridization arrest and use of an oligodeoxynucleotide to effect RNase H cleavage of the RNA target. Accordingly, there remains a continuing long-felt need for methods and compounds for regulation of target RNA. Such regulation of target RNA would be useful for therapeutic purposes both in vivo and ex vivo and, as well as, for diagnostic reagents and as research reagents including reagents for the study of both cellular and in vitro events.

SUMMARY OF THE INVENTION

In accordance with this invention there are provided oligomeric compounds formed from a linear sequence of linked ribonucleoside subunits that are specifically hybridizable to a preselected RNA target. The oligomeric compounds have at least a first segment and a second segment. The first segment incorporates at least one ribonucleoside subunit that is modified to improve at least one of its pharmacokinetic properties, its binding characteristics to target RNA or to modify its charge. The second segment includes at least four consecutive ribofuranosyl nucleoside subunits. The subunits of the oligomeric compounds are connected together in a linear sequence by internucleoside linkages that are stabilized from degradation as compared to phosphodiester linkages.

In certain preferred embodiments of the invention, the compounds will include a third segment having properties corresponding to the properties of the first segment. It is preferred to position the second segment between the first and third segments such that they form a continuous, linear sequences of linked nucleoside units. In preferred compounds the number of such linked nucleoside subunits will range from about eight to about fifty with a more preferred range being from about twelve to about thirty linked nucleoside subunits.

Modification of pharmacokinetic properties includes any one or more of the modification of binding, absorption, distribution or clearance properties of the compound. Modification of binding characteristics includes modification of the affinity or specificity of said compound to its target RNA. Modification of the charge of said compound includes modifying the net charge of the compound as compared to an unmodified compound. Normally modification of charge will decrease the overall net negative charge of a phosphorus linked oligomeric compound to provide the compound with less negative charge, a neutral charge or a net positive charge.

Further in accordance with this invention, there are provided oligomeric compounds formed from linear sequences of linked ribonucleoside subunits that are specifically hybridizable to a preselected RNA target. The oligomeric compounds have at least a first segment and a second segment. The first segment incorporates at least one ribonucleoside subunit that is functionalized to provide greater affinity to the target RNA. The second segment includes at least four ribofuranosyl nucleoside subunits. The subunits of the oligomeric compounds are connected together in a linear sequence by internucleoside linkages that are modified to stabilize the linkages from degradation as compared to phosphodiester linkages.

In certain preferred oligomeric compounds of the invention, the first or first and third segments of oligomeric compounds are formed of nucleoside subunits that include 2'-substituent groups thereon. In preferred embodiments, the 2'-substituent group includes fluoro, $C_1$-$C_{20}$ alkoxy, $C_1$-$C_9$ aminoalkoxy, allyloxy, imidazolylalkoxy and polyethylene glycol. Preferred alkoxy substituents include methoxy, ethoxy and propoxy. A preferred aminoalkoxy substituent is aminopropoxy. A preferred imidazolylalkoxy substituent is imidazolylpropoxy. A preferred polyethylene glycol substituent is —O-ethyl-O-methyl, i.e., methoxyethoxy or —O—CH$_2$—CH$_2$—O—CH$_3$.

In further preferred oligomeric compounds of the invention, the oligomeric compounds are formed of nucleoside subunits that are modified by including certain selected nucleobases thereon. In preferred embodiments, the selected nucleobases include 2,6-diaminopurine, N2-alkylpurines, N2-aminoalkylpurines, 7-deaza-7-substituted purines, 5-substituted pyrimidines, and 2-substituted pyrimidines.

Other preferred oligomeric compounds of the invention include oligoribonucleotides having nucleoside subunits connected by phosphorus linkages including phosphorothioate, 3'-(or -5')deoxy-3'-(or -5') thio-phosphorothioate, phosphoro-dithioate, phosphoroselenates, 3'-(or -5')deoxy phosphinates, borano phosphates, 3'-(or -5')deoxy-3'-(or 5'-) amino phosphor-amidates, hydrogen phosphonates, borano phosphate esters, phosphoramidates, alkyl or aryl phosphonates and phospho-triester linkages. A selected group of oligoribonucleotide linkages for use in linking the nucleosides of the second segment include phosphorothioate, phosphinates and phosphor-amidates, all of which are charged species.

Further preferred oligomeric compounds of the invention may also include oligoribonucleosides having nucleoside subunits connected by carbonate, carbamate, silyl, sulfur, sulfonate, sulfonamide, formacetal, thioformacetal, oxime, methyleneimino, methylenemethylimino, methylenehydrazo, methylenedimethylhydrazo and methyleneoxymethylimino linkages.

Further preferred oligomeric compounds of the invention include having nucleoside subunits connected by alternating phosphorus and non-phosphorous linkages. Such non-phosphorous linkages include carbonate, carbamate, silyl, sulfur, sulfonate, sulfonamide, formacetal, thioformacetal, oxime, methyleneimino, methylenemethylimino, methylenehydrazo, methylenedimethylhydrazo and methyleneoxymethylimino linkages while the phosphorous linkages include phosphodiester, phosphorothioate, 3'-(or -5')deoxy-3'-(or -5') thio-phosphoro-thioate, phosphorodithioate, phosphoroselenates, 3'-(or -5')deoxy phosphinates, borano phosphates, 3'-(or -5')deoxy-3'-(or 5'-)amino phosphoramidates, hydrogen phosphonates, borano phosphate esters, phosphoramidates, alkyl or aryl phosphonates and phosphotriester linkages.

Further preferred oligomeric compounds of the invention include oligoribonucleotides, oligoribonucleosides or mixtures of oligoribonucleotides and oligoribonucleosides having a plurality of linked nucleoside subunits that are linked in a sequences that is complementary strand of target RNA and wherein the sequence of the compound is divided into a first subsequence or segment and a second subsequence or segment. The first subsequence comprises linked nucleoside subunits bearing 2'-O-substituted-pentofuranosyl sugar moieties and the second subsequence comprises linked nucleoside subunits bearing 2'-hydroxyl-pentofuranosyl sugar moieties. Preferably, said second subsequence has from four to twelve or more nucleoside subunits, and more preferably, has five to about nine nucleoside subunits. In further preferred embodiments there exists a third subsequence, the nucleoside subunits of which are selected from those which are selectable for the first subsequence. It is preferred that the second subsequence be positioned between the first and the third subsequences. Such oligomeric compounds of the invention are also referred to as "chimeras," "chimeric" or "gapped" oligoribonucleotides or oligoribonucleosides.

In further preferred oligomeric compounds of the invention, nucleoside subunits bearing substituents that are modified to improve at least one of: pharmacokinetic binding, absorption, distribution or clearance properties of the compound: affinity or specificity of said compound to said target RNA: or modification of the charge of said compound, compared to an unmodified compound; are located at one or both of the 3' or the 5' termini of the oligomeric compounds. In certain preferred compounds there are from one to about eight nucleoside subunits that are substituted with such substituent groups.

The nucleoside subunits are joined together in a linear sequence to form the oligomeric compounds of the invention. Each nucleoside subunit includes a base fragment and a sugar fragment. The base fragment comprises a heterocyclic base, alternately hereinafter referred to as a nucleobase. The bases or nucleobases are covalently bonded to the sugar fragment. The sugar fragments may include a 2'-substituted sugar moiety, a 2'-hydroxyl sugar moiety or a sugar surrogate moiety.

Preferred nucleobases of the invention include purines and pyrimidines such as adenine, guanine, cytosine, uridine, and thymine, as well as other synthetic and natural nucleobases such as xanthine, hypoxanthine, 2-aminoadenine, 6-methyl and other alkyl derivatives of adenine and guanine, 2-propyl and other alkyl derivatives of adenine and guanine, 5-halouracil and cytosine, 5-propynyl uracil and cytosine, 6-azo uracil, cytosine and thymine, 5-uracil (pseudouracil), 4-thiouracil, 8-halo, amino, thiol, thioalkyl, hydroxyl and other 8-substituted adenines and guanines, 5-trifluoromethyl and other 5-substituted uracils and cytosines, and 7-methylguanine. Further purines and pyrimidines include those disclosed in U.S. Pat. Nos. 3,687,808, 5,484,908, 5,459,255, 5,457,191 and 5,614,617 (corresponding to U.S. patent application Ser. No. 07/971,978), and those disclosed in the *Concise Encyclopedia Of Polymer Science And Engineering*, pages 858-859, Kroschwitz, J. I., ed. John Wiley & Sons, 1990, and those disclosed by Englisch et al., *Angewandte Chemie, International Edition*, 1991, 30, 613.

Preferred sugar fragments are pentoribofuranosyl sugar moieties, i.e, the "natural" sugar moiety of messenger ribonucleic acids. Other sugar-like or sugar surrogate compounds suitable for use in the oligoribonucleotides or oligoribonucleosides of the invention include cyclobutyl nucleoside surrogates as described in U.S. Pat. No. 5,359,044, pyrrolidine nucleoside surrogates as described in U.S. Pat. No. 5,519,134, morpholino nucleoside surrogates as described in U.S. Pat. Nos. 5,142,047 and 5,235,033, and in related patent disclosures, and PNA (peptide nucleic acid) nucleoside surrogates.

In further preferred embodiments of the invention there are provided synthetic oligomeric compounds that are specifically hybridizable with a preselected RNA target and where the compounds include a first segment including at least one surrogate nucleoside subunit and a second segment comprising at least four ribofuranosyl nucleoside subunits located in a consecutive sequence and having 2'-hydroxyl moieties thereon. Further the nucleoside subunits of the oligomeric compound are connected by internucleoside linkages that are stable to degradation as compared to phosphodiester bonds.

In other preferred embodiments of the invention, there are provided synthetic oligomeric compounds that are specifically hybridizable with a preselected RNA target and that include a first segment having at least one ribofuranosyl nucleoside subunit that is not a DNA or RNA "major" building block nucleoside and a second segment that includes at least four consecutive ribofuranosyl nucleoside subunits having 2'-hydroxyl moieties thereon. The nucleoside subunits of the compounds are connected by internucleoside linkages which are modified to stabilize the linkages from degradation as compared to phosphodiester linkages. Nucleoside subunits that are not DNA or RNA major building block nucleosides as that term is used in connection with this invention, are members of the group consisting of adenosine, 2'-deoxyadenosine, guanosine, 2'-deoxyguanosine, cytidine, 2'-deoxycytidine, uridine and 2'-deoxythymidine. As such, this group excludes "minor" nucleosides that may be found in tRNA or in other nucleic acids.

The invention also provides methods of for specifically cleaving preselected RNA. These methods include contacting the RNA with a compound that includes at least twelve ribofuranosyl nucleosides subunits joined in a sequence which is specifically hybridizable with the preselected RNA. The nucleoside subunits are joined by internucleoside bonds that are stable to degradation as compared to phosphodiester bonds. The compound has at least one segment that includes at least one modified nucleoside subunit, which modified nucleoside subunit is modified to improve at least one of pharmacokinetic binding, absorption, distribution or clearance properties of the compound; affinity or specificity of the compound to target RNA; or modification of the charge of the compound, compared to an unmodified compound. The compound additionally includes a further segment having at least four ribonucleoside subunits.

The invention also provides methods for treating an organism having a disease characterized by the undesired production of a protein. These methods include contacting the organism with an oligomeric compound of the invention having a sequence of nucleoside subunits capable of specifically hybridizing with a complementary strand of ribonucleic acid with at least one of the nucleoside subunits being functionalized to modify one of more properties of the oligomeric compounds compared to native RNA. The compound further includes a plurality of the nucleoside subunits having 2'-hydroxyl-pentofuranosyl sugar moieties.

Further in accordance with the present invention, there are provided compositions including a pharmaceutically effective amount of an oligomeric compound having a sequence of nucleoside subunits capable of specifically hybridizing with a complementary strand of RNA and wherein at least one of the nucleoside subunits is modified to improve at least one of pharmacokinetic binding, absorption, distribution or clearance properties of the compound; affinity or specificity of said compound to said target RNA; or modification of the charge of said compound, compared to an unmodified compound. In such compounds, a plurality of the nucleoside subunits have 2'-hydroxyl-pentofuranosyl sugar moieties. The compositions further include a pharmaceutically acceptable diluent or carrier.

The present invention also provides mammalian ribonucleases, isolatable from human T24 cells, other cell lines, and rat tissues, that degrade RNA in an oligoribonucleotide:RNA duplex. Such a ribonuclease is referred to herein as a dsRNase, wherein "ds" indicates the RNase's specificity for certain double-stranded RNA substrates. Useful substrates for such dsRNases are also herein provided, as well as affinity matrices comprising such substrates.

Methods are also provided for in vitro modification of a sequence-specific target RNA including contacting a test solution containing a dsRNase enzyme, i.e., a double stranded RNase enzyme, and said target RNA with an oligomeric compound. The oligomeric compound has a sequence of nucleoside subunits capable of specifically hybridizing to a complementary strand of the nucleic acid, where at least one of the nucleoside subunits is functionalized to increase the binding affinity or binding specificity of the oligoribonucleotide to the complementary strand of nucleic acid, and where a plurality of the nucleoside subunits have 2'-hydroxyl-pentofuranosyl sugar moieties.

There are also provided methods of concurrently enhancing hybridization and/or dsRNase enzyme activation in an organism that includes contacting the organism with an oligomeric compound having a sequence of nucleoside subunits capable of specifically hybridizing to a complementary strand of target RNA. At least one of the nucleoside subunits is modified to improve at least one of pharmacokinetic binding, absorption, distribution or clearance properties of the compound; affinity or specificity of said compound to said target RNA; or modification of the charge of said compound, compared to an unmodified compound. Again, a plurality of the nucleoside subunits have 2'-hydroxy-pentofuranosyl sugar moieties.

The invention further provides diagnostic methods for detecting the presence or absence of abnormal RNA molecules, or abnormal or inappropriate expression of normal RNA molecules in organisms or cells. The invention further provides research reagents for modulating enzyme activity including dsRNase activity in in vitro solutions.

BRIEF DESCRIPTION OF THE DRAWINGS

FIG. 1 schematically depicts certain illustrative chimeric oligomeric compounds of the invention wherein open squares represent 2'-methoxy modified ribonucleotides, filled circles represent 2'-hydroxyl ribonucleotides and phosphorothioate linkages are utilized through the compounds shown in the figure.

FIG. 2 depicts Ha-ras mRNA levels in cells treated with full 2'-methoxy or chimeric RNA gapmer oligonucleotides. Northern blot analyses for Ha-ras mRNA levels in T24 cells treated with the indicated doses of full 2'-methoxy oligonucleotide (panel 2A) or 3 gap oligoribonucleotide (panel 2C) for 24 hrs. are shown. The upper band is the signal for Ha-ras, this signal was normalized to that obtained for G3PDH (lower band), relative Ha-ras levels were determined and are presented graphically (panels 2C-2D). Neither oligonucleotide treatment reduced Ha-ras mRNA levels.

FIG. 3 shows Northern blot analyses of T24 cell treated as in FIG. 2 except with chimeric RNA gapmer oligonucleotides containing either a 5, 7 or 9 ribonucleotide gap or a full ribonucleotide molecule (left panels 3A, 3B, 3C and 3D, respectively); cells were also treated with a control oligoribonucleotide that contains four mismatched base pairs to the Ha-ras mRNA sequence (left panel 3E). Ha-ras signals were normalized to that of G3PDH and relative Ha-ras levels are shown graphically (right panels).

DETAILED DESCRIPTION OF PREFERRED EMBODIMENTS

Figure 4:
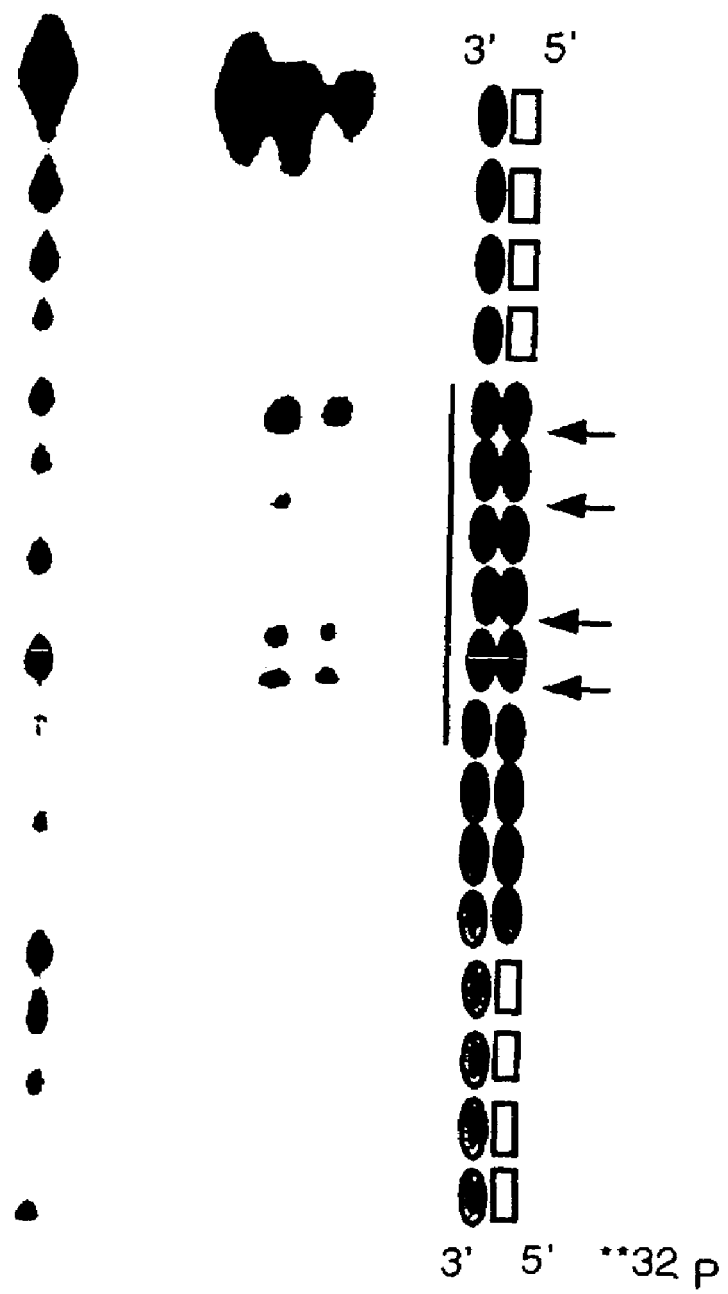
In FIG. 4, the effect of T24 cytosolic extracts and RNase H on duplexes in vitro are shown. A 17 base pair duplex consisting of the Ha-ras targeted 9 RNA gapmer oligonucleotide annealed to a $^{32}$P-labeled RNA complement was incubated with 3 ug of T24 cytosolic protein fraction for the indicated times at 37° C., the reaction was stopped and products were resolved on a denaturing polacrylamide gel. Digestion products (arrows) indicate that cleavage of the duplex is restricted to the RNA:RNA region (see schematic of duplex, far right).

While not wishing to be bound by theory, it is now believed that by the use of certain chemically modified oligomeric compounds, one can exploit certain enzymatic activities in eukaryotic cells, including human cells, resulting from the unexpected interaction of these compounds with a target RNA strand to form double-stranded RNA like structures that are cleaved by certain enzymes. Heretofore, such activity has not recognized nor exploited in eukaryotic systems. It has now been found that the oligomeric compounds of the invention have certain RNA like features that allow them to form a double stranded structure with a targeted RNA region and this double stranded structure is subsequently degraded by eukaryotic dsRNases, i.e. double-stranded RNase enzymes, in a cell or test solution. Using T24 human bladder carcinoma cells as an illustrative eukaryotic cellular system, it has been demonstrated that this activity is present at comparable levels in both the nuclear and cytoplasmic fractions.

In certain illustrative procedures provided herein to illustrate this invention, in common with some other known nuclease activities, it has been found that this activity leaves 5' phosphate and 3' hydroxyl groups after cleavage of the RNA substrate. This generation of 5' phosphate, 3' hydroxyl termini is a feature in common with several other nucleases that recognize double-stranded nucleic acid molecules, including RNase HI and II that cleave the RNA component of a DNA:RNA duplex in $E.$ $coli.$, RNase III which catalyses the hydrolysis of high molecular weight double stranded RNA and mediates degradation of sense-antisense duplexes, and RNase V1.

Many components of mRNA degradation systems have been conserved between prokaryotes and eukaryotes. It has now been found that like prokaryotic organisms, in which RNase III carries out the degradation of sense-antisense hybrids to regulate expression of some genes, human cells have conserved an activity capable of performing a similar role. In addition to other uses including therapeutic and diagnostic uses, by virtue of this activity the compounds of this invention can be used as research reagents to assist in understanding how human cells use endogenously expressed antisense transcripts to modulate gene expression.

The vast majority of antisense oligonucleotides used experimentally or currently being tested in the clinic in humans are modified oligodeoxynucleotides. It has been demonstrated that the heteroduplex formed between such oligodeoxynucleotide antisense compounds and their target RNA is recognized by an intracellular nuclease, RNase H, that cleaves only the RNA strand of this duplex. Although RNase H mediated degradation of target RNA has proven a useful mechanism, it has certain limitations. RNase H is highly sensitive to structural modifications made to the, antisense oligonucleotides and thus most of the modifications designed to improve the therapeutic properties such as increased affinity, increased nuclease resistance and greater cellular permeability have resulted in oligonucleotides that do not support cleavage by RNase H. Another limitation to RNase H as a terminating mechanism of antisense action is the fact that the oligonucleotides must be DNA 'like', and in being DNA 'like', such oligonucleotides have inherently low affinity for their target RNA. Strategies designed to circumvent this low affinity include the design of "gapmer" oligonucleotides that are composed of a stretch of high affinity chemically modified oligonucleotides on the 5' and 3' ends (the wings) with a stretch of unmodified deoxyoligonucleotides in the center (the gap). DNA gapmers, i.e., oligodeoxynucleotides gapmers, have significantly higher affinities for their target than oligodeoxynucleotides, however, depending on the size of the DNA gap, RNase H activity has been shown to be compromised.

In using RNase H as a termination mechanism via RNA degradation, the cellular localization and tissue distribution of RNase H must also be considered. RNase H activity is primarily localized to the nucleus although it has been detected in the cytoplasm at lower levels. Most of a given mRNA is found in the cytoplasm of cells, therefore the ideal activity to be exploited as a terminating mechanism would be one with high levels in both the nucleus and the cytoplasm. RNase H activity also is highly variable from cell line to cell line or between tissues, thus a given disease state may not be a good candidate for RNA degradation only because the target tissue has insufficient RNase H activity. It is clear that alternative terminating mechanisms for degrading target RNA are highly desirable.

Among other uses, the activity that has now been recognized can now be exploited as an alternative terminating mechanism to RNase H for antisense therapeutics. It has been found that in using RNA-like oligonucleotides that have high affinity for their target and thus higher potency than DNA-like oligonucleotides, activity can be expressed in human cells. The presence of the activity in both the cytoplasm and the nucleus allows the compounds of the invention to be used to inhibit many RNA processing events from nuclear premRNA splicing and transport to degradation of mature transcript in the cytoplasm.

To illustrate this invention and to compare it to other known antisense mechanisms, e.g. RNase H, the dsRNAse activity induced by the compounds of the invention has been examined by targeting it to codon 12 of Ha-ras. As described in U.S. Pat. No. 5,297,248, corresponding to Ser. No. 08/297,248, and its related application International Publication Number WO 92/22651, published Dec. 23, 1992, both commonly assigned with this application, the entire contents of which are herein incorporated by reference, the ras oncogenes are members of a gene family that encode related proteins that are localized to the inner face of the plasma membrane and have been shown to be highly conserved at the amino acid level, to bind GTP with high affinity and specificity, and to possess GTPase activity. Although the cellular function of ras gene products is unknown, their biochemical properties, along with their significant sequence homology with a class of signal-transducing proteins, known as GTP binding proteins, or G proteins, suggest that ras gene products play a fundamental role in basic cellular regulatory functions related to the transduction of extracellular signals across plasma membranes.

Three ras genes, designated H-ras, K-ras, and N-ras, have been identified in the mammalian genome. Mammalian ras genes acquire transformation-inducing properties by single point mutations within their coding sequences. Mutations in naturally occurring ras oncogenes have been localized to codons 12, 13, and 61. The most commonly detected activating ras mutation found in human tumors is in codon 12 of the H-ras gene in which a base change from GGC to GTC results in a glycine-to-valine substitution in the GTPase regulatory domain of the ras protein product. This single amino acid change is thought to abolish normal control of ras protein function, thereby converting a normally regulated cell protein to one that is continuously active. It is believed that such deregulation of normal ras protein function is responsible for the transformation from normal to malignant growth.

While for illustrative purposes, the compounds of the invention are targeted to ras RNA, it is of course recognized that a host of other RNAs also are suitable as the target RNA. Thus the compounds of the invention can be used to modulate the expression of any suitable target RNA that is naturally present in cells or any target RNA in vitro.

The ras target site utilized for illustrative purposes is one the most RNase H sensitive oligonucleotide sites that has been identified in the literature. The selective inhibition of mutated genes such as the ras oncogene necessitates hybridization of a regulatory compound in the coding region of the mRNA. This requires either a high affinity interaction between such a compound and ras mRNA to prevent displacement of the compound by the polysome, or rapid degradation of the target mRNA by a given terminating mechanism. Again while not wishing to be bound by theory, the RNA like compounds of the invention, have both inherently high affinity and are able to take advantage of the cellular dsRNAse activity.

In accordance with the objects of this invention, novel oligomeric compounds that bind to a target RNA strand and that are substrates for dsRNase enzymes are provided. The oligomeric compounds of the invention include oligoribonucleotides, oligoribonucleosides and other oligomeric compounds having a linear sequence of linked ribonucleoside subunits incorporated therein. Such other oligomeric compounds will include chimeric structures formed between PNA (peptide nucleic acid) segments and linked ribonucleosides. Thus for the purposes of this specification, the term "oligomeric compound" is meant to be inclusive of the terms oligoribonucleotides and oligoribonucleosides, either used singly or in combination, as well as other oligomeric compounds including chimeric compounds formed between PNA segments (and other surrogate nucleoside components) and linked ribonucleoside segments. As used in this specification and the claims attached hereto, in one sense the term oligomeric compound is used to represent oligoribonucleotides, in a further sense to represent oligoribonucleosides, in even a further sense to represent mixtures of oligoribonucleotides and oligoribonucleosides and in other instances to indicated further chimeric compounds such as the above identified PNA chimeric compounds.

The oligoribonucleotides and oligoribonucleosides of the invention are assembled from a plurality of nucleoside subunits. In certain preferred oligoribonucleotide or oligoribonucleosides of the invention at least one of the nucleoside subunits bear a substituent group that increases the binding affinity of the oligoribonucleotide or oligoribonucleoside for a complementary strand of nucleic acid. Additionally, at least some of the nucleoside subunits comprise 2'-hydroxyl-pentofuranosyl sugar moieties.

For cellular use, for an oligonucleotide to be particularly useful, the oligonucleotide must be reasonably stable to nucleases in order to survive in cells for a time period sufficient for it to interact with target nucleic acids of the cells. Therefore, in certain embodiments of the invention, specific nucleoside subunits or internucleoside linkages are functionalized or selected to increase the nuclease resistance of the oligoribonucleotide or oligoribonucleoside. However, for non-cellular uses, such as use of oligomeric compounds of the invention as research reagents and as diagnostic agents, such nuclease stability may not be necessary.

In determining the extent of binding affinity of a first nucleic acid to a complementary nucleic acid, the relative ability of the first nucleic acid to bind to the complementary nucleic acid may be compared by determining the melting temperature of a particular hybridization complex. The melting temperature ($T_m$), a characteristic physical property of double stranded nucleotides, denotes the temperature (in degrees centigrade) at which 50% helical (hybridized) versus coil (unhybridized) forms are present. $T_m$ is measured by using the UV spectrum to determine the formation and breakdown (melting) of the hybridization complex. Base stacking which occurs during hybridization is accompanied by a reduction in UV absorption (hypochromicity). Consequently, a reduction in UV absorption indicates a higher $T_m$. The higher the $T_m$, the greater the strength of the bonds between the strands.

It has been found in the present invention that the binding affinity of oligoribonucleotides and oligoribonucleosides of the present invention can be increased by incorporating substituent groups in the nucleoside subunits of these compounds. Preferred substituent groups are 2' substituent groups, i.e. substituent groups located at the 2' position of the pentofuranosyl sugar moieties of the nucleoside subunits of the compounds of the present invention. Presently preferred substituent groups include fluoro, alkoxy, amino-alkoxy, allyloxy, imidazolylalkoxy and polyethylene glycol. Alkoxy and aminoalkoxy groups generally include lower alkyl groups, particularly $C_1$-$C_9$ alkyl. Polyethylene glycols are of the structure (O—$CH_2$—$CH_2$)$_n$—O-alkyl. A particularly preferred substituent group is a polyethylene glycol substituent of the formula (—O—$CH_2$—$CH_2$)$_n$—O-alkyl, wherein n=1 and alkyl=$CH_3$. This modification has been shown to increase both affinity of a oligonucleotide for its target and nuclease resistance of an oligonucleotide.

A further particularly useful 2'-substituted group for increasing the binding affinity is the 2'-fluoro group. In a published study (*Synthesis and Biophysical Studies of 2'-dRIBO-F Modified Oligonucleotides*, Conference On Nucleic Acid Therapeutics, Clearwater, Fla., Jan. 13, 1991) an increase in binding affinity of 1.6° C. per substituted nucleoside subunit was reported for a 15-mer phosphodiester oligonucleotide having 2'-fluoro substituent groups on five of the nucleoside subunits of the oligonucleotide. When 11 of the nucleoside subunits of the oligonucleotide bore 2'-fluoro substituent groups, the binding affinity increased to 1.8° C. per substituted nucleoside subunit. In this study, the 15-mer phosphodiester oligonucleotide was derivatized to the corresponding phosphorothioate analog. When the 15-mer phosphodiester oligonucleotide was compared to its phosphorothioate analog, the phosphorothioate analog had a binding affinity of only about 66% of that of the 15-mer phosphodiester oligonucleotide. Stated otherwise, binding affinity was lost in derivatizing the oligonucleotide to its phosphorothioate analog. However, when 2'-fluoro substituents were located on 11 of the nucleosides subunits of the 15-mer phosphorothioate oligonucleotide, the binding affinity of the 2'-substituent groups more than overcame the decrease noted by derivatizing the 15-mer oligonucleotide to its phosphorothioate analog. In this compound, i.e. the 15-mer phosphorothioate oligonucleotide having 11 nucleoside subunits substituted with 2'-fluoro substituent groups, the binding affinity was increased to 2.5° C. per substituent group.

For use in preparing the nucleoside structural subunits of the compounds of the invention, suitable nucleobases for incorporation in these nucleoside subunits include purines and pyrimidines such as adenine, guanine, cytosine, uridine, and thymine, as well as other synthetic and natural nucleobases such as xanthine, hypoxanthine, 2-aminoadenine, 6-methyl and other alkyl derivatives of adenine and guanine, 2-propyl and other alkyl derivatives of adenine and guanine, 5-halouracil and cytosine, 5-propynyl uracil and cytosine, 6-azo uracil, cytosine and thymine, 5-uracil (pseudouracil), 4-thiouracil, 8-halo, amino, thiol, thioalkyl, hydroxyl and other 8-substituted adenines and guanines, 5-trifluoromethyl and other 5-substituted uracils and cytosines, 7-methylguanine. Further purines and pyrimidines include those disclosed in U.S. Pat. No. 3,687,808, those disclosed in the *Concise Encyclopedia Of Polymer Science And Engineering*, pages 858-859, Kroschwitz, J. I., ed. John Wiley & Sons, 1990, and those disclosed by Englisch et al., *Angewandte Chemie, International Edition*, 1991, 30, 613. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. Other modified pyrimidine and purine bases are also expected to increase the binding affinity of oligomeric compounds to a complementary strand of nucleic acid.

Preferred oligoribonucleotides and oligoribonucleosides in accordance with this invention preferably comprise from about 5 to about 50 nucleoside subunits. In the context of this invention it is understood that this encompasses non-naturally occurring oligomers as hereinbefore described, having 5 to 50 nucleoside subunits. It is more preferred that the oligoribonucleotides and oligoribonucleosides of the present invention comprise from about 15 to about 25 nucleoside subunits. As will be appreciated, a "nucleoside subunit" is a nucleobase and sugar or sugar surrogate combination suitably bound to adjacent subunits through phosphorus linkages in oligoribonucleotides and through non-phosphorus linkages in oligoribonucleosides. In this context, the term "nucleoside subunit" is used interchangeably with the term "nucleoside unit" or "nucleoside."

The oligoribonucleotides of the invention have their nucleoside subunits connected by phosphorus linkages including phosphodiester, phosphorothioate, 3'-(or -5') deoxy-3'-(or -5')thio-phosphorothioate, phosphorodithioate, phosphoro-selenates, 3'-(or -5')deoxy phosphinates, borano phosphates, 3'-(or -5')deoxy-3'-(or 5'-)amino phosphoramidates, hydrogen phosphonates, borano phosphate esters, phosphoramidates, alkyl or aryl phosphonates and phosphotriester phosphorus linkages. Whereas the oligoribonucleosides of the invention have their nucleoside subunits connected by carbonate, carbamate, silyl, sulfur, sulfonate, sulfonamide, formacetal, thioformacetyl, oxime, methyleneimino, methylenemethylimino, methylenehydrazo, methylenedimethylhydrazo and methyleneoxymethylimino linkages.

In order to elicit a dsRNase response within the total overall sequence length of the oligomeric compounds of the invention there will be a segment or subsequence of greater than three, but preferably, four, five or more consecutively linked 2'-hydroxyl-pentofuranosyl-containing nucleoside subunits. It is presently preferred to incorporate the 2'-hydroxyl-pentofuranosyl-containing nucleoside subsequence in the oligomeric compound such that further subsequences or segments of oligomeric compound are located on either side of the 2'-hydroxyl-pentofuranosyl-containing nucleoside subsequence. In such a construction, the 2'-hydroxyl-pentofuranosyl containing nucleoside subsequence is also referred to as the "central" or "gap" region or segment and the other nucleoside subsequences or segments are referred to as "flanking" or "wing" regions or segments. Thus the "gap" region is flanked on either side by "wings." Other constructions are also possible, including locating the 2'-hydroxyl-pentofuranosyl containing nucleoside subsequence at either the 3' or the 5' terminus of the oligomeric compound of the invention. These other constructions can be considered as "open" gapped structures, i.e., the gap region is open on the end (either 3' or 5' end) of the oligomeric compound.

The oligoribonucleotides and oligoribonucleosides used in accordance with this invention may be conveniently and routinely made through the well-known technique of solid phase synthesis, see for example "Oligonucleotide synthesis, a practical approach", Ed. M. J. Gait, IRL Press, 1984; "Oligonucleotides and Analogues, A Practical Approach", Ed. F. Eckstein, IRL Press, 1991 (especially Chapter 1, Modern machine-aided methods of oligodeoxyribonucleotide synthesis, Chapter 2, Oligoribonucleotide synthesis, Chapter 3, 2'-O-Methyloligoribonucleotides: synthesis and applications, Chapter 4, Phosphorothioate oligonucleotides, Chapter 5, Synthesis of oligonucleotide phosphorodithioates, Chapter 6, Synthesis of oligo-2'-deoxyribonucleoside methylphosphonates, and. Chapter 7, Oligodeoxynucleotides containing modified bases. Other particularly useful synthetic procedures, reagents, blocking groups and reaction conditions are described in Martin, P., *Helv. Chim. Acta*, 1995, 78, 486-504; Beaucage, S. L. and Iyer, R. P., *Tetrahedron*, 1992, 48, 2223-2311 and Beaucage, S. L. and Iyer, R. P., *Tetrahedron*, 1993, 49, 6123-6194, or references referred to therein.

Equipment for oligonucleotide and oligonucleoside synthesis is sold by several vendors including Applied Biosystems. Various amidite reagents are also commercially available, including 2'-O-methyl amidites and 2'-O-hydroxyl amidites. Any other means for such synthesis may also be employed. The actual synthesis of the oligonucleotides is well within the talents of those skilled in the art. It is also well known to use similar techniques to prepare other oligonucleotides such as the phosphorothioates and alkylated derivatives. It is also well known to use similar techniques and commercially available modified amidites and controlled-pore glass (CPG) products such as biotin, fluorescein, acridine or psoralen-modified amidites and/or CPG (available from Glen Research, Sterling Va.) to synthesize fluorescently labeled, biotinylated or other conjugated oligonucleotides.

In a further embodiment, the present invention is drawn to a mammalian ribonuclease isolatable from human T24 cells, and other cell lines, that degrades RNA in an antisense oligoribonucleotide:RNA duplex. The ribonuclease is referred to herein as a dsRNase, wherein "ds" indicates the RNase's specificity for double-stranded RNA substrates. Antisense oligodeoxynucleotides containing 2'-methoxy modified sugar moieties bind to their cellular mRNA targets with high affinity but the resulting ["DNA-like"]:[RNA] duplexes are not substrates for nucleolytic degradation in T24 cells. As detailed in the Examples, 2'-methoxy phosphorothioate antisense oligonucleotides targeting codon 12 of Ha-Ras mRNA were modified by substituting 2'-methoxy nucleotides with a stretch of ribonucleotides in the center of the oligonucleotide to form 2'-methoxy/ribo/2'-methoxy chimeric or "gapmer" oligonucleotides, with the phosphorothioate linkage maintained throughout the molecules. These "RNA-like" gapmer oligonucleotides bind to their cellular mRNA target with an affinity comparable to that of the full 2'-methoxy oligodeoxynucleotide, but, unlike the ["DNA-like"]:[RNA] duplexes, the resultant ["RNA-like"]:[RNA] duplexes are substrates for nucleolytic degradation in T24 cells. Degradation of the [antisense "RNA-like" gapmer oligonucleotide]: [Ha-Ras mRNA] duplex is dependent on the number of ribonucleotides incorporated into the antisense molecule. A 17 base pair 9 RNA gapmer oligonucleotide:RNA duplex is not a substrate for RNase H cleavage, but is a substrate for cleavage by an the dsRNase of the invention in T24 cellular lysates. Furthermore, the cleavage sites seen with T24 cellular lysates are localized to the RNA:RNA portion of the duplex and are not seen in the 2'-methoxy:RNA portion of the duplex. Cleavage of the duplex by the dsRNase of the invention produces 5'-phosphate and 3'-hydroxyl termini.

Compounds of the invention can be utilized as diagnostics, therapeutics and as research reagents and kits. They can be utilized in pharmaceutical compositions by adding an effective amount of a compound of the invention to a suitable pharmaceutically acceptable diluent or carrier. They further can be used for treating organisms having a disease characterized by the undesired production of a protein. The organism can be contacted with a compound of the invention having a sequence that is capable of specifically hybridizing with a strand of target nucleic acid that codes for the undesirable protein.

The formulation of therapeutic compositions and their subsequent administration is believed to be within the skill of those in the art. In general, for therapeutics, a patient in need of such therapy is administered a compound in accordance with the invention, commonly in a pharmaceutically acceptable carrier, in doses ranging from 0.01 µg to 100 g per kg of body weight depending on the age of the patient and the severity of the disease state being treated. Further, the treatment regimen may last for a period of time which will vary depending upon the nature of the particular disease, its severity and the overall condition of the patient, and may extend from once daily to once every 20 years. Following treatment, the patient is monitored for changes in his/her condition and for alleviation of the symptoms of the disease state. The dosage of the compound may either be increased in the event the patient does not respond significantly to current dosage levels, or the dose may be decreased if an alleviation of the symptoms of the disease state is observed, or if the disease state has been ablated.

In some cases it may be more effective to treat a patient with a compound of the invention in conjunction with other traditional therapeutic modalities. For example, a patient being treated for a viral disease may be administered a compound of the invention in conjunction with a known antiviral agent, or a patient with atherosclerosis may be treated with a compound of the invention following angioplasty to prevent reocclusion of the treated arteries.

Following successful treatment, it may be desirable to have the patient undergo maintenance therapy to prevent the recurrence of the disease state, wherein the compound of the invention is administered in maintenance doses, ranging from 0.01 µg to 100 g per kg of body weight, once or more daily, to once every 20 years.

The pharmaceutical compositions of the present invention may be administered in a number of ways depending upon whether local or systemic treatment is desired and upon the area to be treated. Administration may be topical (including ophthalmic, vaginal, rectal, intranasal, transdermal), oral or parenteral. Parenteral administration includes intravenous drip, subcutaneous, intraperitoneal or intramuscular injection, or intrathecal or intraventricular administration.

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions for oral administration include powders or granules, suspensions or solutions in water or non-aqueous media, capsules, sachets or tablets. Thickeners, flavoring agents, diluents, emulsifiers, dispersing aids or binders may be desirable.

Compositions for intrathecal or intraventricular administration may include sterile aqueous solutions which may also contain buffers, diluents and other suitable additives.

Formulations for parenteral administration may include sterile aqueous solutions which may also contain buffers, diluents and other suitable additives.

Dosing is dependent on severity and responsiveness of the disease condition to be treated, with the course of treatment lasting from several days to several months, or until a cure is effected or a diminution of disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual compounds, and can generally be estimated based on $EC_{50}$s found to be effective in in vitro and in vivo animal models. In general, dosage is from 0.01 µg to 100 g per kg of body weight, and may be given once or more daily, weekly, monthly or yearly, or even once every 2 to 20 years.

Such treatment can be practiced in a variety of organisms ranging from unicellular prokaryotic and eukaryotic organisms to multicellular eukaryotic organisms. Any organism that utilizes DNA-RNA transcription or RNA-protein translation as a fundamental part of its hereditary, metabolic or cellular machinery is susceptible to such diagnostic, therapeutic and/or prophylactic treatment. Seemingly diverse organisms such as bacteria, yeast, protozoa, algae, plant and higher animal forms, including warm-blooded animals, can be treated in this manner. Further, since each of the cells of multicellular eukaryotes also includes both DNA-RNA transcription and RNA-protein translation as an integral part of their cellular activity, such therapeutics and/or diagnostics can also be practiced on such cellular populations. Furthermore, many of the organelles, e.g. mitochondria and chloroplasts, of eukaryotic cells also include transcription and translation mechanisms. As such, single cells, cellular populations or organelles also can be included within the definition of organisms that are capable of being treated with the therapeutic or diagnostic compounds of the invention. As used herein, therapeutics is meant to include eradication of a disease state, killing of an organism, e.g. bacterial, protozoan or other infection, or control of aberrant or undesirable cellular growth or expression.

In the context of this invention, "target RNA" shall mean any RNA that can hybridize with a complementary nucleic acid like compound. Further in the context of this invention, "hybridization" shall mean hydrogen bonding, which may be Watson-Crick, Hoogsteen or reversed Hoogsteen hydrogen bonding, between complementary nucleobases. "Complementary" as used herein, refers to the capacity for precise pairing between two nucleobases. For example, adenine and thymine are complementary nucleobases which pair through the formation of hydrogen bonds. "Complementary" and "specifically hybridizable," as used herein, refer to precise pairing or sequence complementarity between a first and a second nucleic acid-like oligomers containing nucleoside subunits. For example, if a nucleobase at a certain position of the first nucleic acid is capable of hydrogen bonding with a nucleobase at the same position of the second nucleic acid, then the first nucleic acid and the second nucleic acid are considered to be complementary to each other at that position. The first and second nucleic acids are complementary to each other when a sufficient number of corresponding positions in each molecule are occupied by nucleobases which can hydrogen bond with each other. Thus, "specifically hybridizable" and "complementary" are terms which are used to indicate a sufficient degree of complementarity such that stable and specific binding occurs between a compound of the invention and a target RNA molecule. It is understood that an oligomeric compound of the invention need not be 100% complementary to its target RNA sequence to be specifically hybridizable. An oligomeric compound is specifically hybridizable when binding of the oligomeric compound to the target RNA molecule interferes with the normal function of the target RNA to cause a loss of utility, and there is a sufficient degree of complementarity to avoid non-specific binding of the oligomeric compound to non-target sequences under conditions in which specific binding is desired, i.e. under physiological conditions in the case of in vivo assays or therapeutic treatment, or in the case of in vitro assays, under conditions in which the assays are performed.

The following examples and procedures illustrate the present invention and are not intended to limit the same. In illustrating the invention, Example 1 identifies certain commercial nucleoside amidites and other additional nucleoside amidites that are useful for the preparation of certain illustrative oligoribonucleotide or oligoribonucleoside compounds of the invention. Examples 2 through 5 illustrate the preparation of further nucleoside amidites use in preparing other illustrative oligoribonucleotide or oligoribonucleoside compounds of the invention. Example 6 illustrates the preparation of oligoribonucleotide compounds of the invention. Example 7 illustrates the preparation of oligoribonucleoside compounds of the invention. Examples 8 through 16 illustrate the preparation of chimeric oligomeric compounds of the invention including certain "gapmers," i.e., compounds having "gap" and "wing" constructions. Examples 17 through 18 illustrate certain useful aspects of the compounds of the invention. Examples 19 through 28 illustrate the identification, characterization and purification of the double-stranded ribonucleases (dsRNases) of the invention. Example 29 illustrates affinity columns incorporating the dsRNase substrates of the invention.

In the illustrative examples, several different types of "gapmers" are exemplified. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. In the illustrative examples, for all chimeric oligoribonucleotides and oligoribonucleosides, unless otherwise indicated, 2'-O-methyl nucleosides are utilized in the "wing" segments and 2'-OH nucleosides are utilized in the "gap" segments of the respective oligoribonucleotides or oligoribonucleosides.

For the purposes of the illustrative examples the following short hand conventions are used. Structure set forth in brackets, i. e. [ ], are nucleoside abbreviations, while structures set forth following a slash mark, i.e. /, are linkers used to connect the nucleosides, i.e. backbone structures that link the nucleosides together in either oligoribonucleotide or oligoribonucleoside compounds.

Using this nomenclature, the following abbreviations are used for phosphate linkages between nucleosides: PO for phosphodiester; PS for phosphorothioate, P2S for phosphorodithioate, PSe for phosphoroselenates, PMe for methyl phosphonate, POMe for methyl phosphotriester, PN for phosphoramidate, 3'NPN for 3'-deoxy-3'-amino phosphoramidate, PI for phosphinate, MePS for alkylphosphonothioate, BP for borano phosphate are used. For non-phosphate linkages between nucleosides the abbreviations used are: MMI for methylenemethylimino, MDH for methylenedimethylhydrazo, FA for formacetal, TFA for thioformacetal, ETO for ethylene oxide and amide-3 for methylenecarbonylamino. 2'-OH is utilized as an abbreviation for unmodified ribo sugars, i.e. pentoribofuranosyl sugars. For modified nucleosides the abbreviations used are: 2'-O-alkyl for general alkyl groups at the 2' position of a pentoribofuranosyl moiety with specific alkyl being noted as 2'-O-Me, 2'-O-Et, 2'-O—Pr and 2'-O-EtOMe for methyl, ethyl, propyl and methoxyethyl, respectively; 2'-F for a fluoro moiety at the 2' position of a pentoribofuranosyl moiety, Mod-Purine for a purine nucleobase substitution as, for example, per the disclosure of U.S. Pat. No. 5,459,255 or; and Mod-Pyr for a pyrimidine nucleobase substitution as, for example, per the disclosure of U.S. Pat. No. 5,484,908; SS for a sugar surrogate as, for example, per the disclosure of U.S. Pat. No. 5,359,044.

EXAMPLE 1

Amidites for oligonucleotide/oligonucleoside Synthesis

2'-O-Methyl nucleoside amidites and 2'-OH (blocked as 2'-t-butyldimethylsilyl derivative) nucleoside amidites are available from Glen Research, Sterling, Va. Other 2'-O-alkyl substituted nucleoside amidites are prepared as is described in U.S. Pat. Nos. 5,506,351, 5,466,786 or 5,514,786, herein incorporated by reference. Cyclobutyl sugar surrogate compounds are prepared as is described in U.S. Pat. No. 5,359,044, herein incorporated by reference. Pyrrolidine sugar surrogate are prepared as is described in U.S. Pat. No. 5,519,134, herein incorporated by reference. Morpholino sugar surrogates are prepared as is described in U.S. Pat. Nos. 5,142,047 and 5,235,033, herein incorporated by reference, and other related patent disclosures. N-2 substituted purine nucleoside amidites are prepared as is described in U.S. Pat. No. 5,459,255, herein incorporated by reference. 3-Deaza purine nucleoside amidites are prepared as is described in U.S. Pat. No. 5,457,191, herein incorporated by reference. 5,6-Substituted pyrimidine nucleoside amidites are prepared as is described in U.S. Pat. No. 5,614,617 herein incorporated by reference. 5-Propynyl pyrimidine nucleoside amidites are prepared as is described in U.S. Pat. No. 5,484,908, herein incorporated by reference.

EXAMPLE 2

2'-O-(Methoxyethyl) nucleoside amidites

2'-O-Ethyl-O-methyl substituted nucleoside amidites are prepared as follows in Examples 2-a through 2-h or alternately, as per the methods of Martin, P., *Helvetica Chimica Acta*, 1995, 78, 486-504.

EXAMPLE 2-a 2,2'-Anhydro[1-(β-D-arabinofuranosyl)-5-methyluridine]

5-Methyluridine (ribosylthymine, commercially available through Yamasa, Choshi, Japan) (72.0 g, 0.279 M), diphenylcarbonate (90.0 g, 0.420 M) and sodium bicarbonate (2.0 g, 0.024 M) were added to DMF (300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured into fresh ether (2.5 L) to yield a stiff gum. The ether was decanted and the gum was dried in a vacuum oven (60° C. at 1 mm Hg for 24 h) to give a solid which was crushed to a light tan powder (57 g, 85% crude yield). The NMR spectrum was consistent with the structure, contaminated with phenol as its sodium salt (ca. 5%). The material was used as is for further reactions (or it can be purified further by column chromatography using a gradient of methanol in ethyl acetate (10-25%) to give a white solid, mp 222-4° C.).

EXAMPLE 2-b

2'-O-Methoxyethyl-5-methyluridine 2,2'-Anhydro-5-methyluridine (195 g, 0.81 M), tris(2-methoxyethyl)borate (231 g, 0.98 M) and 2-methoxyethanol (1.2 L) were added to a 2 L stainless steel pressure vessel and placed in a pre-heated oil bath at 160° C. After heating for 48 hours at 155-160° C., the vessel was opened and the solution evaporated to dryness and triturated with MeOH (200 mL). The residue was suspended in hot acetone (1 L). The insoluble salts were filtered, washed with acetone (150 mL) and the filtrate evaporated. The residue (280 g) was dissolved in $CH_3CN$ (600 mL) and evaporated. A silica gel column (3 kg) was packed in $CH_2Cl_2$/acetone/MeOH (20:5:3) containing 0.5% $Et_3NH$. The residue was dissolved in $CH_2Cl_2$ (250 mL) and adsorbed onto silica (150 g) prior to loading onto the column. The product was eluted with the packing solvent to give 160 g (63%) of product. Additional material was obtained by reworking impure fractions.

EXAMPLE 2-c

2'-O-Methoxyethyl-5'-O-dimethoxytrityl-5-methyluridine

2'-O-Methoxyethyl-5-methyluridine (160 g, 0.506 M) was co-evaporated with pyridine (250 mL) and the dried residue dissolved in pyridine (1.3 L). A first aliquot of dimethoxytrityl chloride (94.3 g, 0.278 M) was added and the mixture stirred at room temperature for one hour. A second aliquot of dimethoxytrityl chloride (94.3 g, 0.278 M) was added and the reaction stirred for an additional one hour. Methanol (170 mL) was then added to stop the reaction. HPLC showed the presence of approximately 70% product. The solvent was evaporated and triturated with $CH_3CN$ (200 mL). The residue was dissolved in $CHCl_3$ (1.5 L) and extracted with 2×500 mL of saturated $NaHCO_3$ and 2×500 mL of saturated NaCl. The organic phase was dried over $Na_2SO_4$, filtered and evaporated. 275 g of residue was obtained. The residue was purified on a 3.5 kg silica gel column, packed and eluted with EtOAc/Hexane/Acetone (5:5:1) containing 0.5% $Et_3NH$. The pure fractions were evaporated to give 164 g of product. Approximately 20 g additional was obtained from the impure fractions to give a total yield of 183 g (57%).

EXAMPLE 2-d

3'-O-Acetyl-2'-O-methoxyethyl-5'-O-dimethoxytrityl-5-methyluridine

2'-O-Methoxyethyl-5'-O-dimethoxytrityl-5-methyluridine (106 g, 0.167 M), DMF/pyridine (750 mL of a 3:1 mixture prepared from 562 mL of DMF and 188 mL of pyridine) and acetic anhydride (24.38 mL, 0.258 M) were combined and stirred at room temperature for 24 hours. The reaction was monitored by tlc by first quenching the tlc sample with the addition of MeOH. Upon completion of the reaction, as judged by tlc, MeOH (50 mL) was added and the mixture evaporated at 35° C. The residue was dissolved in $CHCl_3$ (800 mL) and extracted with 2×200 mL of saturated sodium bicarbonate and 2×200 mL of saturated NaCl. The water layers were back extracted with 200 mL of $CHCl_3$. The combined organics were dried with sodium sulfate and evaporate to give 122 g of residue (approx. 90% product). The residue was purified on a 3.5 kg silica gel column and eluted using EtOAc/Hexane (4:1). Pure product fractions were evaporated to yield 96 g (84%). An additional 1.5 g was recovered from later fractions.

EXAMPLE 2-e

3'-O-Acetyl-2'-O-methoxyethyl-5'-O-dimethoxytrityl-5-methyl-4-triazoleuridine

A first solution was prepared by dissolving 3'-O-acetyl-2'-O-methoxyethyl-5'-O-dimethoxytrityl-5-methyluridine (96 g, 0.144 M) in $CH_3CN$ (700 mL) and set aside. Triethylamine (189 mL, 1.44 M) was added to a solution of triazole (90 g, 1.3 M) in $CH_3CN$ (1 L), cooled to −5° C. and stirred for 0.5 h using an overhead stirrer. $POCl_3$ was added dropwise, over a 30 minute period, to the stirred solution maintained at 0-10° C., and the resulting mixture stirred for an additional 2 hours. The first solution was added dropwise, over a 45 minute period, to the later solution. The resulting reaction mixture was stored overnight in a cold room. Salts were filtered from the reaction mixture and the solution was evaporated. The residue was dissolved in EtOAc (1 L) and the insoluble solids were removed by filtration. The filtrate was washed with 1×300 mL of NaHCO$_3$ and 2×300 mL of saturated NaCl, dried over sodium sulfate and evaporated. The residue was triturated with EtOAc to give the title compound.

EXAMPLE 2-f

2'-O-Methoxyethyl-5'-O-dimethoxytrityl-5-methyl-cytidine

A solution of 3'-O-acetyl-2'-O-methoxyethyl-5'-O-dimethoxytrityl-5-methyl-4-triazoleuridine (103 g, 0.141 M) in dioxane (500 mL) and NH$_4$OH (30 mL) was stirred at room temperature for 2 hours. The dioxane solution was evaporated and the residue azeotroped with MeOH (2×200 mL). The residue was dissolved in MeOH (300 mL) and transferred to a 2 liter stainless steel pressure vessel. MeOH (400 mL) saturated with NH$_3$ gas was added and the vessel heated to 100° C. for 2 hours (tlc showed complete conversion). The vessel contents were evaporated to dryness and the residue was dissolved in EtOAc (500 mL) and washed once with saturated NaCl (200 mL). The organics were dried over sodium sulfate and the solvent was evaporated to give 85 g (95%) of the title compound.

EXAMPLE 2-g $N^4$-Benzoyl-2'-O-methoxyethyl-5'-O-dimethoxytrityl-5-methylcytidine 2'-O-Methoxyethyl-5'-O-dimethoxytrityl-5-methylcytidine (85 g, 0.134 M) was dissolved in DMF (800 mL) and benzoic anhydride (37.2 g, 0.165 M) was added with stirring. After stirring for 3 hours, tlc showed the reaction to be approximately 95% complete. The solvent was evaporated and the residue azeotroped with MeOH (200 mL). The residue was dissolved in CHCl$_3$ (700 mL) and extracted with saturated NaHCO$_3$ (2×300 mL) and saturated NaCl (2×300 mL), dried over MgSO$_4$ and evaporated to give a residue (96 g). The residue was chromatographed on a 1.5 kg silica column using EtOAc/Hexane (1:1) containing 0.5% Et$_3$NH as the eluting solvent. The pure product fractions were evaporated to give 90 g (90%) of the title compound.

EXAMPLE 2-h $N^4$-Benzoyl-2'-O-methoxyethyl-5'-O-dimethoxytrityl-5-methylcytidine-3'-amidite $N^4$-Benzoyl-2'-O-methoxyethyl-5'-O-dimethoxytrityl-5-methylcytidine (74 g, 0.10 M) was dissolved in CH$_2$Cl$_2$ (1 L). Tetrazole diisopropylamine (7.1 g) and 2-cyanoethoxy-tetra-(isopropyl)phosphite (40.5 mL, 0.123 M) were added with stirring, under a nitrogen atmosphere. The resulting mixture was stirred for 20 hours at room temperature (tlc showed the reaction to be 95% complete). The reaction mixture was extracted with saturated NaHCO$_3$ (1×300 mL) and saturated NaCl (3×300 mL). The aqueous washes were back-extracted with CH$_2$Cl$_2$ (300 mL), and the extracts were combined, dried over MgSO$_4$ and concentrated. The residue obtained was chromatographed on a 1.5 kg silica column using EtOAc\Hexane (3:1) as the eluting solvent. The pure fractions were combined to give 90.6 g (87%) of the title compound.

EXAMPLE 3

Preparation of Long Chain, i.e. (C$_{20}$), Substituted nucleoside amidites

Synthesis of nucleoside amidites having long chains, e.g. C$_{20}$, substituents at their 2' position is shown in Examples 3-a through 3-c.

EXAMPLE 3-a

Synthesis of 2,6-Diamino-9-(2-O-octadecyl-β-D-ribofuranosyl)purine 2,6-Diamino-9-(β-D-ribofuranosyl)purine (50 g, 180 mmol) and sodium hydride (7 g) in DMF (1 L) were heated to boiling for 2 hr. Iodooctadecane (100 g) was added at 150° C. and the reaction mixture allowed to cool to RT. The reaction mixture was stirred for 11 days at RT. The solvent was evaporated and the residue purified by silica gel chromatography. The product was eluted with 5% MeOH/CH$_2$Cl$_2$. The appropriate fractions were evaporated to yield the product (11 g). $^1$H NMR (DMSO-d$_6$) δ 0.84 (t, 3, CH$_2$); 1.22 (m, 32, O—CH$_2$—CH$_2$—(CH$_2$)$_{16}$); 1.86 (m, 2, O—CH$_2$CH$_2$); 3.25 (m, 2, O —CH$_2$); 3.93 (d, 1, 4'H), 4.25 (m, 1, 3'H); 4.38 (t, 1, 2'H); 5.08 (d, 1, 3'-OH); 5.48 (t, 1, 5'-OH); 5.75 (s, 2, 6-NH$_2$); 5.84 (d, 1, 1'-H); 6.8 (s, 2, 2-NH$_2$); and 7.95 (s, 1, 8-H)

EXAMPLE 3-b

Synthesis of 2'-O-Octadecylguanosine 2,6-Diamino-9-(2-O-octadecyl-β-D-ribofuranosyl) purine (10 g) in 0.1 M sodium phosphate buffer (50 mL, pH 7.4), 0.1 M tris buffer (1000 mL, pH 7.4) and DMSO (1000 mL) was treated with adenosine deaminase (1.5 g) at RT. At day 3, day 5 and day 7 an additional aliquot (500 mg, 880 mg and 200 mg, respectively) of adenosine deaminase was added. The reaction was stirred for a total of 9 day and purification by silica gel chromatography yielded the product (2 g). An analytical sample was recrystallized from MeOH $^1$H NMR (DMSO-d$_6$) δ 0.84 (t, 3, CH$_3$), 1.22 [s, 32, O—CH$_2$—CH$_2$—(CH$_2$)$_{16}$], 5.07 (m, 2, 3'-OH and 5'-OH); 5.78 (d, 1, 1'-H); 6.43 (s, 2, NH$_2$), 7.97 (s, 1, 8-H) and 10.64 (S, 1, NH$_2$). Anal. Calcd. for C$_{28}$H$_{49}$N$_5$O$_5$: C, 62.80; H, 9.16; N, 12.95. Found: C, 62.54; H, 9.18; N, 12.95.

EXAMPLE 3-c

Synthesis of $N^2$-Isobutyryl-2'-O-octadecylguanosine

2'-O-Octadecylguanosine (1.9 g) in pyridine (150 mL) was cooled in an ice bath, and treated with trimethylsilyl chloride (2 g, 5 eq) and isobutyryl chloride (2 g, 5 eq). The reaction mixture was stirred for 4 hours, during which time it was allowed to warm to room temperature. The solution was cooled, water added (10 mL) and stirred for an additional 30 minutes. Concentrated ammonium hydroxide (10 mL) was added and the solution concentrated in vacuo. The residue was purified by silica gel chromatography (eluted with 3% MeOH/EtOAc) to yield 1.2 g of product. $^1$H NMR (DMSO-d$_6$) δ 0.85 (t, 3, CH$_3$), 1.15 (m, 38, O—CH$_2$CH$_2$(CH$_2$)$_{16}$, CH(CH$_3$)$_2$), 2.77 (m, 1, CH(CH$_3$)$_2$), 4.25 (m, 2, 2'-H and 3'-H); 5.08 (t, 1, 5'-OH), 5.12 (d, 1, 3'-OH), 5.87 (d, 1, 1'-H), 8.27 (s, 1, 8-H), 11.68 (s, 1, NH$_2$) and 12.08 (s, 1, NH$_2$). Anal. Calcd. for C$_{32}$H$_{55}$N$_5$O$_6$: C, 63.47; H, 9.09; N, 11.57. Found: C, 63.53; H, 9.20; N, 11.52. Prior to incorporating this product into an oligonucleotide, it was converted to $N^2$-Isobutyryl-5'-dimethoxytrityl-2'-O-octadecyl-guanosine and then to a phosphoramidite according to the procedures described in International Publication Number WO 94/02501, published Feb. 3, 1994.

EXAMPLE 4

2'-Fluoro nucleoside amidites

2'-fluoro substituted nucleoside amidites are prepared as follows in Examples 4-a through 4-d or alternately as per the method of Kawasaki et. al., *J. Med. Chem.*, 1993, 36, 831-841.

EXAMPLE 4-a i. $N^6$-Benzoyl-9-β-D-arabinofuranosyladenine.

9-β-D-arabinofuranosyladenine (1.07 g, 4.00 mmol) was dissolved in anhydrous pyridine (20 mL) and anhydrous dimethylformamide (20 mL) under an argon atmosphere. The solution was cooled to 0° C. and chlorotrimethylsilane (3.88 mL, 30.6 mmol) was added slowly to the reaction mixture via a syringe. After stirring the reaction mixture at 0° C. for 30 minutes, benzoyl chloride (2.32 mL, 20 mmol) was added slowly. The reaction mixture was allowed to warm to 20° C. and stirred for 2 hours. After cooling the reaction mixture to 0° C., cold water (8 mL) was added and the mixture was stirred for 15 minutes. Concentrated ammonium hydroxide (8 mL) was slowly added to the reaction mixture to give a final concentration of 2 M of ammonia. After stirring the cold reaction mixture for 30 minutes, the solvent was evaporated in vacuo (60 torr) at 20° C. followed by evaporation in vacuo (1 torr) at 40° C. to give an oil. This oil was triturated with diethyl ether (50 mL) to give a solid which was filtered and washed with diethyl ether three times. This crude solid was triturated in methanol (100 mL) at reflux temperature three times and the solvent was evaporated to yield $N^6$-Benzoyl-9-β-D-arabino-furanosyladenine as a solid (1.50 g, 100%).

ii. $N^6$-Benzoyl-9-[3',5'-di-O-tetrahydropyran-2-yl)-β-D-arabino furanosyl]adenine $N^6$-Benzoyl-9-β-D-arabinofuranosyladenine (2.62 g, 7.06 mmol) was dissolved in anhydrous dimethylformamide (150 mL) under argon and p-toluenesulfonic acid monohydrate (1.32 g, 6.92 mmol) was added. This solution was cooled to 0° C. and dihydropyran (1.26 mL, 13.8 mmol) was added via a syringe. The reaction mixture was allowed to warm to 20° C. Over a period of 5 hours a total of 10 equivalents of dihydropyran were added in 2 equivalent amounts in the fashion described. The reaction mixture was cooled to 0° C. and saturated aqueous sodium bicarbonate was added slowly to a pH of 8, then water was added to a volume of 750 mL. The aqueous mixture was extracted with methylene chloride (4×200 mL), and the organic phases were combined and dried over magnesium sulfate. The solids were filtered and the solvent was evaporated in vacuo (60 torr) at 30° C. to give a small volume of liquid which was evaporated in vacuo (1 torr) at 40° C. to give an oil. This oil was coevaporated with p-xylene in vacuo at 40° C. to give an oil which was dissolved in methylene chloride (100 mL). Hexane (200 mL) was added to the solution and the lower-boiling solvent was evaporated in vacuo at 30° C. to leave a white solid suspended in hexane. This solid was filtered and washed with hexane (3×10 mL) then purified by column chromatography using silica gel and methylene chloride-methanol (93:7) as the eluent. The first fraction yielded the title compound 3 as a white foam (3.19 g, 83%) and a second fraction gave a white foam (0.81 g) which was characterized as the 5'-monotetrahydropyranyl derivative of $N^6$-Benzoyl-9-β-D-arabinofuranosyladenine.

iii. $N^6$-Benzoyl-9-[2'-O-trifluoromethylsulfonyl-3',5'-di-O-tetrahydropyran-2-yl)-β-D-arabinofuranosyl]adenine $N^6$-Benzoyl-9-[3',5'-di-O-tetrahydropyran-2-yl)-β-D-arabinofuranosyl]adenine (2.65 g, 4.91 mmol) was dissolved in anhydrous pyridine (20 mL) and the solvent was evaporated in vacuo (1 mm Hg) at 40° C. The resulting oil was dissolved in anhydrous methylene chloride (130 mL) under argon anhydrous pyridine (3.34 mL, 41.3 mmol) and N,N-dimethylaminopyridine (1.95 g, 16.0 mmol) were added. The reaction mixture was cooled to 0° C. and trifluoromethanesulfonic anhydride (1.36 mL, 8.05 mmol) was added slowly via a syringe. After stirring the reaction mixture at 0° C. for 1 hour, it was poured into cold saturated aqueous sodium bicarbonate (140 mL). The mixture was shaken and the organic phase was separated and kept at 0° C. The aqueous phase was extracted with methylene chloride (2×140 mL). The organic extracts which were diligently kept cold were combined and dried over magnesium sulfate. The solvent was evaporated in vacuo (60 torr) at 20° C. then evaporated in vacuo (1 torr) at 20° C. to give $N^6$-Benzoyl-9-[2'-O-trifluoromethylsulfonyl-3',5'-di-O-tetrahydropyran-2-yl)-β-D-arabinofuranosyl]adenine as a crude oil which was not purified further.

iv. N-Benzoyl-9-[2'-fluoro-3',5'-di-O-tetrahydropyran-2-yl)-β-D-arabinofuranosyl]adenine.

$N^6$-Benzoyl-9-[2'-O-trifluoromethylsulfonyl-3',5'-di-O-tetrahydropyran-2-yl)-β-D-arabinofuranosyl]adenine (4.9 mmol) as a crude oil was dissolved in anhydrous tetrahydrofuran (120 mL) and this solution was cooled to 0° C. under argon. Tetrabutylammonium fluoride as the hydrate (12.8 g, 49.1 mmol) was dissolved in anhydrous tetrahydrofuran (50 mL) and half of this volume was slowly added via a syringe to the cold reaction mixture. After stirring at 0° C. for 1 hour, the remainder of the reagent was added slowly. The reaction mixture was stirred at 0° C. for an additional 1 hour, then the solvent was evaporated in vacuo (60 torr) at 20° C. to give an oil. This oil was dissolved in methylene chloride (250 mL) and washed with brine three times. The organic phase was separated and dried over magnesium sulfate. The solids were filtered and the solvent was evaporated to give an oil. The crude product was purified by column chromatography using silica gel in a sintered-glass funnel and ethyl acetate was used as the eluent. $N^6$-Benzoyl-9-[2'-fluoro-3',5'-di-O-tetrahydropyran-2-yl) -β-D-arabinofuranosyl]adenine was obtained as an oil (2.03 g, 76%).

v. $N^6$-Benzoyl-9-(2'-fluoro-β-D-ribofuranosyl)adenine.

$N^6$-Benzoyl-9-[2'-fluoro-3',5'-di-O-tetrahydropyran-2-yl)-β-D-arabinofuranosyl]adenine (1.31 g, 2.42 mmol) was dissolved in methanol (60 mL), and Dowex 50W×2-100 (4 $cm^3$, 2.4 m. eq) was added to the reaction mixture. The reaction mixture was stirred at 20° C. for 1 hour then cooled to 0° C. Triethylamine (5 mL) was then slowly added to the cold reaction mixture to a pH of 12. The resin was filtered and washed with 30% triethylamine in methanol until the wash no longer contained UV absorbing material. Toluene (50 mL)

was added to the washes and the solvent was evaporated at 24° C. in vacuo (60 torr, then 1 torr) to give a residue. This residue was partially dissolved in methylene chloride (30 mL) and the solvent was transferred to a separatory funnel. The remainder of the residue was dissolved in hot (60° C.) water and after cooling the solvent it was also added to the separatory funnel. The biphasic system was extracted, and the organic phase was separated and extracted with water (3×100 mL). The combined aqueous extracts were evaporated in vacuo (60 torr, then 1 torr Hg) at 40° C. to give an oil which was evaporated with anhydrous pyridine (50 mL). This oil was further dried in vacuo (1 torr Hg) at 20° C. in the presence of phosphorous pentoxide. overnight to give $N^6$-benzoyl-9-(2'-fluoro-b-D-ribofuranosyl)adenine as a yellow foam (1.08 g, 100%) which contained minor impurities.

vi. $N^6$-Benzoyl-9-[2'-fluoro-5'-O-(4,4'-dimethoxy-trityl)-β-D-ribofuranosyl]adenine.

$N^6$-Benzoyl-9-(2'-fluoro-b-D-ribofuranosyl)adenine (1.08 g, 2.89 mmol) which contained minor impurities was dissolved in anhydrous pyridine (20 mL) under argon and dry triethylamine (0.52 mL, 3.76 mmol) was added followed by addition of 4,4'-dimethoxytrityl chloride (1.13 g, 3.32 mmol). After 4 hours of stirring at 20° C. the reaction mixture was transferred to a separatory funnel and diethyl ether (40 mL) was added to give a white suspension. This mixture was washed with water three times (3×10 mL), the organic phase was separated and dried over magnesium sulfate. Triethylamine (1 mL) was added to the solution and the solvent was evaporated in vacuo (60 torr Hg) at 20° C. to give an oil which was evaporated with toluene (20 mL) containing triethylamine (1 mL). This crude product was purified by column chromatography using silica gel and ethyl acetate-triethylamine (99:1) followed by ethyl acetate-methanol-triethylamine (80:19:1) to give the product in two fractions. The fractions were evaporated in vacuo (60 torr, then 1 torr Hg) at 20° C. to give a foam which was further dried in vacuo (1 torr Hg) at 20° C. in the presence of sodium hydroxide to give $N^6$Benzoyl-9-[2'-fluoro-5'-O-(4,4'-dimethoxytrityl)-β-D-ribofuranosyl]adenine as a foam (1.02 g, 52%).

vii. $N^6$-Benzoyl-[2'-fluoro-5'-O-(4,4'-dimethoxy trityl)]-adenosine-3'-O-N,N-diisopropyl-β-cyanoethyl phosphoramidite.

$N^6$-Benzoyl-9-[2'-fluoro-5'-O-(4,4'-dimethoxytrityl)-β-D-ribofuranosyl]adenine (1.26 g, 1.89 mmol) was dissolved in anhydrous dichloromethane (13 mL) under argon, diisopropylethylamine (0.82 mL, 4.66 mmol) was added, and the reaction mixture was cooled to 0° C. Chloro(diisopropylamino)-β-cyanoethoxyphosphine (0.88 mL, 4.03 mmol) was added to the reaction mixture which was allowed to warm to 20° C. and stirred for 3 hours. Ethylacetate (80 mL) and triethylamine (1 mL) were added and this solution was washed with brine (3×25 mL). The organic phase was separated and dried over magnesium sulfate. After filtration of the solids the solvent was evaporated in vacuo at 20° C. to give an oil which was purified by column chromatography using silica gel and hexanes-ethyl acetate-triethyl-amine (50:49:1) as the eluent. Evaporation of the fractions in vacuo at 20° C. gave a foam which was evaporated with anhydrous pyridine (20 mL) in vacuo (1 torr) at 26° C. and further dried in vacuo (1 torr Hg) at 20° C. in the presence of sodium hydroxide for 24 h to give $N^6$-Benzoyl-[2'-deoxy-2'-fluoro-5'-O-(4,4'-dimethoxytrityl)]-adenosine-3'-O-(N,N-diisopropyl-β-cyanoethylphosphoramidite as a foam (1.05 g, 63%)

EXAMPLE 4-b

2'-Deoxy-2'-fluoro-5'-O-(4,4'-dimethoxytrityl)-uridine3'O(N,N-diisopropyl-β-cyanoethyl-phosphoramidite).

2,2'-Cyclouridine is treated with a solution of 70% hydrogen fluoride/pyridine in dioxane at 120° C. for ten hours to provide after solvent removal a 75% yield of 2'-deoxy-2'-fluorouridine. The 5'-DMT and 3'-cyanoethoxydiisopropyl-phosphoramidite derivitized nucleoside is obtained by standard literature procedures [Gait, Ed., *Oligonucleotide Synthesis. A Practical Approach*, IRL Press, Washington, D.C. (1984)], or according to the procedure of Example 4-a.

EXAMPLE 4-c

2'-Deoxy-2'-fluoro-S'-O(4,4'-dimethoxytrityl)-cytidine-3'-O-(N,N-diisopropyl-β-cyanoethyl phosphoramidite).

2'-Deoxy-2'-fluorouridine (2.51 g, 10.3 mmol) was converted to corresponding cytidine analog via the method of C. B. Reese, et al., *J. Chem. Soc. Perkin Trans I*, pp. 1171-1176 (1982), by acetylation with acetic anhydride (3.1 mL, 32.7 mmol) in anhydrous pyridine (26 mL) at room temperature. The reaction was quenched with methanol, the solvent was evaporated in vacuo (1 torr) to give an oil which was coevaporated with ethanol and toluene. 3',5'-O-diacetyl-2'-deoxy-2'-fluorouridine was crystallized from ethanol to afford colorless crystals (2.38 g, 81%).

N-4-(1,2,4-triazol-1-yl)-3',5'-O-diacetyl-2'-deoxy-2'-fluorouridine was obtained in a 70% yield (2.37 g) by reaction of 3',5'-O-diacetyl-2'-deoxy-2'-fluorouridine (2.75 g, 9.61 mmol) with 1,2,4-triazole (5.97 g, 86.5 mmol), phosphorus oxychloride (1.73 mL, 18.4 mmol), and triethylamine (11.5 mL, 82.7 mmol) in anhydrous acetonitrile at room temperature. After 90 min the reaction mixture was cooled to ice temperature and triethylamine (7.98 ml, 56.9 mmol) was added followed by addition of water (4.0 ml). The solvent was evaporated in vacuo (1 torr) to give an oil which was dissolved in methylene chloride and washed with saturated aqueous sodium bicarbonate. The aqueous phase was extracted with methylene chloride twice (2×100 mL) and the organic extracts dried with magnesium sulfate. Evaporation of the solvent afforded an oil from which the product N-4-(1,2,4-triazol-1-yl)-3',5'-O-diacetyl-2'-deoxy-2'-fluorouridine was obtained by crystallization from ethanol.

2'-deoxy-2'-fluorocytidine was afforded by treatment of protected triazol-l-yl derivative with concentrated ammonium hydroxide (4.26 mL, 81.2 mmol) in dioxane at room temperature for 6 hours. After evaporation of the solvent the oil was stirred in half-saturated (at ice temperature) ammonia in methanol for 16 hours. The solvent was evaporated and 2'-deoxy-2'-fluoro-cytidine crystallized from ethyl-acetate-methanol (v/v, 75:25) to give colorless crystals (1.24 g, 75%).

N-4-benzoyl-2'-deoxy-2'-fluorocytidine was prepared by selective benzoylation with benzoic anhydride in anhydrous dimethylformamide, V. Bhat, et al. *Nucleosides Nucleotides*, Vol. 8, pp. 179-183 (1989). The 5'-O-(4,4'-dimethoxytrityl)-3'-O-(N,N-diisopropyl-β-cyanoethyl-phosphoramidite) was prepared in accordance with Example 4-a.

EXAMPLE 4-d i. 9-(3',5'-[1,1,3,3-Tetraisopropyldisilox-1,3-diyl]-β-D-arabinofuranosyl)guanine.

The 3' and 5' positions of guanosine were protected by the addition of a TPDS (1,1,3,3-tetraisopropyldisilox-1,3-diyl) protecting group as per the procedure of Robins et al. [*Can. J. Chem.*, 61, 1911 (1983)]. To a stirred solution of DMSO (160 mL) and acetic anhydride (20 mL) was added the TPDS guanosine (21 g, 0.040 mol). The reaction was stirred at room temperature for 36 hours and then cooled to 0° C. Cold ethanol (400 mL, 95%) was added and the reaction mixture further cooled to −78° C. in a dry ice/acetone bath. NaBH$_4$ (2.0 g, 1.32 mol. eq.) was added. The reaction mixture was allowed to warm up to −2° C., stirred for 30 minutes and again cooled to −78° C. This was repeated twice. After the addition of NaBH$_4$ was complete, the reaction was stirred at 0° c. for 30 minutes and then at room temperature for 1 hour. The reaction was taken up in ethyl acetate (1 L) and washed twice with a saturated solution of NaCl. The organic layer was dried over MgSO$_4$ and evaporated under reduced pressure. The residue was coevaporated twice with toluene and purified by silica gel chromatography using CH$_2$Cl$_2$-MeOH (9:1) as the eluent. Pure product (6.02 g) precipitated from the appropriate column fractions during evaporation of these fractions, and an additional 11.49 g of product was obtained as a residue upon evaporation of the fractions.

ii. N$^2$-Isobutyryl-9-(2'-O-isobutyryl-3',5'-[1,1,3,3-tetraisopropyldisilox-1,3-diyl]-β-D-arabinofuranosyl)guanine.

9-(3',5'-[1,1,3,3-Tetraisopropyldisilox-1,3-diyl]-β-D-arabinofuranosyl)guanine (6.5 g, 0.01248 mol) was dissolved in anhydrous pyridine (156 mL) under argon. DMAP (9.15 g) was added. Isobutyric anhydride (6.12 mL) was slowly added and the reaction mixture stirred at room temperature overnight. The reaction mixture was poured into cold saturated NaHCO$_3$ (156 mL) and stirred for 10 minutes. The aqueous solution was extracted three times with ethyl acetate (156 mL). The organic phase was washed three times with saturated NaHCO$_3$ and evaporated to dryness. The residue was coevaporated with toluene and purified by silica gel column chromatography using CH$_2$Cl$_2$-acetone (85:15) to yield 5.67 g of product.

iii. N$^2$-Isobutyryl-9-(2'-O-isobutyryl-β-D-arabinofuranosyl)-guanine.

N$^2$-Isobutyryl-9-(2'-isobutyryl-3',5'-[1,1,3,3-tetra-isopropyldisilox-1,3-diyl]-β-D-arabinofuranosyl)guanine (9.83 g, 0.01476 mol) was dissolved in anhydrous THF (87.4 mL) at room temperature under argon. 1 M (nBu)$_4$N$^+$F$^-$ in THF (29.52 mL, 2 eq.) was added and the reaction mixture stirred for 30 minutes. The reaction mixture was evaporated at room temperature and the residue purified by silica gel column chromatography using EtOAc-MeOH (85:15) to yield 4.98 g (80%) of product.

iv. N$^2$-Isobutyryl-9-(2'-O-isobutyryl-3',5'-di-O-[tetrahydropyran-2-yl]-β-D-arabinofuranosyl)guanine N$^2$-Isobutyryl-9-(2'-isobutyryl-β-D-arabinofuranosyl)-guanine. (4.9 g) was dissolved in anhydrous 1,4-dioxane (98 mL) at room temperature under argon. p-Toluenesulphonic acid monohydrate (0.97 g) was added followed by 3,4-dihydro-2H-pyran (DHP, 9.34 mL, 8.8 eq.). The reaction mixture was stirred for 2 hours, then cooled to 0° C. and saturated NaHCO$_3$ (125 mL) was added to quench the reaction. The reaction mixture was extracted three times with 125 mL portions of CH$_2$Cl$_2$ and the organic phase dried over MgSO$_4$. The organic phase was evaporated and the residue dissolved in minimum volume of CH$_2$Cl$_2$, but in an amount sufficient to yield a clear liquid not a syrup, and then dripped into hexane (100 times the volume of CH$_2$Cl$_2$). The precipitate was filtered to yield 5.59 (81.5%) of product.

v. N$^2$-Isobutyryl-9-(3',5'-di-O-[tetrahydropyran-2-yl]-β-D-arabinofuranosyl)guanine.

N$^2$-Isobutyryl-9-(2'-isobutyryl-3',5'-di-O-[tetrahydropyran-2-yl]-β-D-arabinofuranosyl)guanine (5.58 g) was dissolved in pyridine-MeOH—H$_2$O (65:30:15, 52 mL) at room temperature. The solution was cooled to 0° C. and 52 mL of 2 N NaOH in EtOH-MeOH (95:5) was added slowly, followed by stirring for 2 hours at 0° C. Glacial acetic acid was added to pH 6, and saturated NaHCO$_3$ was added to pH 7. The reaction mixture was evaporated under reduced pressure and the residue coevaporated with toluene. The residue was then dissolved in EtOAc (150 mL) and washed 3× with saturated NaHCO$_3$. The organic phase was evaporated and the residue purified by silica gel column chromatography using EtOAc-MeOH (95:5) as the eluent, yielding 3.85 g (78.3%) of product.

vi. N$^2$-Isobutyryl-9-(3',5'-di-O-[tetrahydropyran-2-yl)]-2'-O-trifluoromethylsulfonyl-β-D-arabinofuranosyl)guanine.

N$^2$-Isobutyryl-9-(3',5'-di-O-[tetrahydropyran-2-yl]-β-D-arabinofuranosyl)guanine (3.84 g) was dissolved in anhydrous CH$_2$Cl$_2$ (79 mL), anhydrous pyridine (5 mL) and DMAP (2.93 g) at room temperature under argon. The solution was cooled to 0° C. and trifluoromethanesulfonic anhydride (1.99 mL) was slowly added with stirring. The reaction mixture was stirred at room temperature for 1 hour then poured into 100 mL of saturated NaHCO$_3$. The aqueous phase was extracted three times with cold CH$_2$Cl$_2$. The organic phase was dried over MgSO$_4$, evaporated and coevaporated with anhydrous MeCN to yield a crude product.

vii. N$^2$-Isobutyryl-9-(2'-deoxy-2'-fluoro-3',5-di-O-[tetrahydropyran-2-yl]-2'-O-trifluoromethylsulfonyl-β-D-ribofuranosyl)guanine.

Crude N$^2$-isobutyryl-9-(3',5'-di-O-[tetrahydropyran-2-yl]-2'-O-trifluoromethylsulfonyl-β-D-arabinofuranosyl)guanine was dissolved in anhydrous THF (113 mL) under argon at 0° C. 1 M (nBu)$_4$N$^+$F$^-$ (dried by coevaporation with pyridine) in THF (36.95 mL) was added with stirring. After 1 hour, a further aliquot of (nBu)$_4$N$^+$F$^-$ in THF (36.95 mL) was added. The reaction mixture was stirred at 0° C. for 5 hours and stored overnight at −30° C. The reaction mixture was evaporated under reduced pressure and the residue dissolved in CH$_2$Cl$_2$ (160 mL) and extracted five times with deionized water. The organic phase was dried over MgSO$_4$ and evaporated. The residue was purified by silica gel column chromatography using EtOAc-MeOH (95:5) to yield 5.25 g of product.

viii. $N^2$-Isobutyryl-9-(2'-deoxy-2'-fluoro-β-D-ribofuranosyl)-guanine.

$N^2$-isobutyryl-9-(2'-deoxy-2'-fluoro-3',5'-di-O-[tetrahydropyran-2-yl]-β-D-ribofuranosyl)guanine (3.85 g) was dissolved in MeOH (80 mL) at room temperature. Pre-washed Dowex 50W resin (12.32 cm³) was added and the reaction mixture stirred at room temperature for 1 hour. The resin was filtered and the filtrate evaporated to dryness. The resin was washed with pyridine-triethylamine-$H_2O$ (1:3:3) until filtrate was clear. This filtrate was evaporated to obtain an oil. The residues from both filtrates were combined in $H_2O$ (200 mL) and washed with $CH_2Cl_2$ (3×100 mL). The aqueous phase was evaporated to dryness and the residue recrystallized from hot MeOH to yield 0.299 g of product as a white powder. The remaining MeOH solution was purified by silica gel column chromatography to further yield 0.783 g of product by elution with EtOH-MeOH (4:1).

ix. $N^2$-Isobutyryl-9-(2'-deoxy-2'-fluoro-5'-O-[4,4-dimethoxy-trityl]-β-D-ribofuranosyl)guanine $N^2$-isobutyryl-9-(2'-deoxy-2'-fluoro-β-D-ribo-furanosyl) guanine (1.09 g) was dissolved in pyridine (20 mL) and triethylamine (0.56 mL) at room temperature under argon. 4,4'-Dimethoxytrityl chloride (1.20 g, 1.15 molar eq.) was added and the reaction mixture stirred at room temperature for 5 hours. The mixture was transferred to a separatory funnel and extracted with diethyl ether (100 mL). The organic phase was washed with saturated $NaHCO_3$ (3×70 mL), and the aqueous phase back-extracted three times with diethyl ether. The combined organic phases were dried over $MgSO_4$ and triethylamine (4 mL) was added to maintain the solution at basic pH. The solvent was evaporated and the residue purified by silica gel column chromatography using EtOAc-triethylamine (100:1) and then EtOAc-MeOH-triethylamine (95:5:1) as eluents yielding 1.03 g of product.

x. $N^2$-Isobutyryl-9-(2'-deoxy-2'-fluoro-5'-O-[4,4-dimethoxy-trityl]-guanosine-3'-O-N,N-diisopropyl-β-D-cyanoethyl phosphoramidite.

$N^2$-isobutyryl-9-(2'-deoxy-2'-fluoro-5'-O-[4,4'-dimethoxytrityl])-β-D-ribofuranosyl)guanine (0.587 g) was dissolved in anhydrous $CH_2Cl_2$ (31 mL) and diisopropylethylamine (0.4 mL) at room temperature under argon. The solution was cooled to 0° C. and chloro(diisopropylamino)-β-cyanoethoxy-phosphine (0.42 mL) was slowly added. The reaction mixture was allowed to warm to room temperature and stirred for 3.5 hours. $CH_2Cl_2$-triethylamine (100:1, 35 mL) was added and the mixture washed with saturated $NaHCO_3$ (6 mL). The organic phase was dried over $MgSO_4$ and evaporated under reduced pressure. The residue was purified by silica gel column chromatography using hexane-EtOAc-triethylamine (75:25:1) for 2 column volumes, then hexane-EtOAc-triethylamine (25:75:1), and finally EtOAc-triethylamine. The product-containing fractions were pooled and the solvent evaporated under reduced pressure. The resulting oil was coevaporated twice with MeCN and dried under reduced pressure. The resulting white solid was dissolved in $CH_2Cl_2$ (3 mL) and dripped into stirring hexane (300 mL). The resulting precipitate was filtered and dried under reduced pressure to yield 0.673 g (88%) of product.

EXAMPLE 5

Nucleoside amidites having substitution on their sugar and their base fragments are shown in Examples 5-a through 5-k.

EXAMPLE 5-a

Other Nucleoside Amidites i. 1-(2-Fluoro-β-D-erythro-pentofuranosyl)-5-methyluridine 2,2'-Anhydro-[1-(β-D-arabinofuranosyl)-5-methyluridine] (71 g, 0.32 mmol) (from Example 2-a) and dioxane (700 mL) are placed in a 2 liter stainless steel bomb and HF/pyridine (100 g, 70%) was added. The mixture was heated for 16 hours at 120-125° C. and then cooled in an ice bath. The bomb was opened and the mixture was poured onto 3 liters of ice. To this mixture was added cautiously sodium hydrogen carbonate (300 g) and saturated sodium bicarbonate solution (400 mL). The mixture was filtered and the filter cake was washed with water (2×100 mL) and methanol (2×500 mL). The water and methanol washes were concentrated to dryness in vacuo. Methanol (200 mL) and coarse silica gel (80 g) were added to the residue and the mixture was concentrated to dryness in vacuo. The resulting material was concentrated onto the silica gel and purified by silica gel column chromatography using a gradient of ethyl acetate and methanol (100:0 to 85:15). Pooling and concentration of the product fractions gave 36.9 g (51%, 2 step yield) of the title compound.

Also isolated from this reaction was 1-(2-phenyl-β-D-erythro-pentofuranosyl)-5-methyluridine (10.3 g). This material is formed from the phenol and its sodium salt from the anhydro reaction above when the bomb reaction is carried out on impure material. When The anhydro material is purified this product is not formed. The formed 1-(2-phenyl-β-D-erythro-pentofuranosyl)-5-methyluridine was converted into its DMT/phosphoramidite using the same reaction conditions as for the 2'-Fluoro material.

ii. 1-(5-O-Dimethoxytrityl-2-fluoro-β-D-erythro-pentofuranosyl)-5-methyluridine 1-(2-fluoro-β-D-erythro-pentofuranosyl)-5-methyl-uridine (31.15 g, 0.12 mol) was suspended in pyridine (150 mL) and dimethoxytrityl chloride (44.62 g, 0.12 mol) was added. The mixture was stirred in a closed flask for 2 hours and then methanol (30 mL) was added. The mixture was concentrated in vacuo and the resulting residue was partitioned between saturated bicarbonate solution (500 mL) and ethyl acetate (3×500 ml). The ethyl acetate fractions were pooled and dried over magnesium sulfate, filtered and concentrated in vacuo to a thick oil. The oil was dissolved in dichloromethane (100 mL), applied to a silica gel column and eluted with ethyl acetate:hexane:triethylamine, 60/39/1 increasing to 75/24/1. The product fractions were pooled and concentrated in vacuo to give 59.9 g (89%) of the title compound as a foam.

iii. 1-(5-O-Dimethoxytrityl-2-fluoro-3-O-N,N-diisopropylamino-2-cyanoethylphosphite-β-D-erythro-pentofuranosyl)-5-methyluridine 1-(5-O-Dimethoxytrityl-2-fluoro-β-D-erythro-pentofuranosyl)-5-methyluridine (59.8 g, 0.106 mol) was dissolved in dichloromethane and 2-cyanoethyl N,N,N',N'-tetraisopropyl-phosphorodiamidite (46.9 mL, 0.148 mol) and diisopropylamine tetrazolide (5.46 g, 0.3 eq.) was added. The mixture was stirred for 16 hours. The mixture was washed with saturated sodium bicarbonate (1 L) and the bicarbonate solution was back extracted with dichloromethane (500 mL). The combined organic layers were washed with brine (1 L) and the brine was back extracted with dichloromethane (100 mL).

The combined organic layers were dried over sodium sulfate, filtered, and concentrated to a vol of about 200 mL. The resulting material was purified by silica gel column chromatography using hexane/ethyl acetate/triethyl amine 60/40/1. The product fractions were concentrated in vacuo, dissolved in acetonitrile (500 ml), filtered, concentrated in vacuo, and dried to a foam. The foam was chopped and dried for 24 hour to a constant weight to give 68.2 g (84%) of the title compound. 1H NMR: (CDCl$_3$) δ 0.9-1.4 (m, 14 H, 4×CH$_3$, 2×CH), 2.3-2.4 (t, 1 H, CH$_2$CN), 2.6-2.7 (t, 1 H, CH$_2$CN), 3.3-3.8 (m, 13 H, 2×CH$_3$OAr, 5' CH$_2$, CH$_2$OP, C-5 CH$_3$), 4.2-4.3 (m, 1 H, 4'), 4.35-5.0 (m, 1 H, 3'), 4.9-5.2 (m, 1 H, 2'), 6.0-6.1 (dd, 1 H, 1'), 6.8-7.4 (m, 13 H, DMT), 7.5-7.6 (d, 1 H, C-6), 8.8 (bs, 1 H, NH). $^{31}$P NMR (CDCl$_3$); 151.468, 151.609, 151.790, 151.904.

iv. 1-(3',5'-di-O-acetyl-2-fluoro-β-D-erythro-pentofuranosyl)-5-methyluridine 1-(2-fluoro-β-D-erythro-pentofuranosyl)-5-methyl-uridine (22.4 g, 92 mmol, 85% purity), prepared as per the procedure of Example 5-a-i., was azeotroped with pyridine (2×150 mL) and dissolved in pyridine (250 mL). Acetic anhydride (55 mL, 0.58 mol) was added and the mixture was stirred for 16 hours. Methanol (50 mL) was added and stirring was continued for 30 minutes. The mixture was evaporated to a syrup. The syrup was dissolved in a minimum amount of methanol and loaded onto a silica gel column. Hexane/ethyl acetate, 1:1, was used to elute the product fractions. Purification gave 19.0 g (74%) of the title compound.

EXAMPLE 5-b i. 4-Triazine-1-(3', 5'-di-O-acetyl-2-fluoro-β-D-erythro-pentofuranosyl)-5-methyluridine 1,2,4-Triazole (106 g, 1.53 mol) was dissolved in acetonitrile (150 mL) followed by triethylamine (257 mL, 1.84 mol). The mixture was cooled to between 0 and 10 oC. using an ice bath. POCl$_3$ (34.5 mL, 0.375 mol) was added slowly via addition funnel and the mixture was stirred for an additional 45 minutes. In a separate flask, 1-(3',5'-Di-O-acetyl-2-fluoro-β-D-erythro-pentofuranosyl)-5-methyluridine (56.9 g, 0.144 mol) was dissolved in acetonitrile (150 mL). The solution containing the 1-(3',5'-Di-O-acetyl-2-fluoro-β-D-erythro-pentofuranosyl)-5-methyluridine was added via cannula to the triazole solution slowly. The ice bath was removed and the reaction mixture was allowed to warm to room temperature for 1 hour. The acetonitrile was removed in vacuo and the residue was partitioned between saturated sodium bicarbonate solution (400 mL) and dichloromethane (4×400 mL). The organic layers were combined and concentrated in vacuo. The resulting residue was dissolved in ethyl acetate (200 mL) and started to precipitate a solid. Hexanes (300 mL) was added and additional solid precipitated. The solid was collected by filtration and washed with hexanes (2×200 mL) and dried in vacuo to give 63.5 g which was used as is without further purification.

ii. 5-methyl-1-(2-fluoro-β-D-erythro-pentofuranosyl)-cytosine

4-Triazine-1-(3',5'-di-O-acetyl-2-fluoro-β-D-erythro-pentofuranosyl)-thymine (75.5 g, 0.198 mol) was dissolved in ammonia (400 mL) in a stainless steel bomb and sealed overnight. The bomb was cooled and opened and the ammonia was evaporated. Methanol was added to transfer the material to a flask and about 10 volumes of ethyl ether was added. The mixture was stirred for 10 minutes and then filtered. The solid was washed with ethyl ether and dried to give 51.7 g (86%) of the title compound.

iii. 4-N-Benzoyl-5-methyl-1-(2-fluoro-β-D-erythro-pento-furanosyl)cytosine

5-Methyl-1-(2-fluoro-β-D-erythro-pentofuranosyl)-cytosine (54.6 g, 0.21 mol) was suspended in pyridine (700 mL) and benzoic anhydride (70 g, 0.309 mol) was added. The mixture was stirred for 48 hours at room temperature. The pyridine was removed by evaporation and methanol (800 mL) was added and the mixture was stirred. A precipitate formed which was filtered, washed with methanol (4×500 mL), washed with ether (3×100 mL), and dried in a vacuum oven at 45° C. to give 40.5 g of the title compound. The filtrate was concentrated in vacuo and treated with saturated methanolic ammonia in a bomb overnight at room temperature. The mixture was concentrated in vacuo and the resulting oil was purified by silica gel column chromatography. The recycled starting material was again treated as above to give an additional 4.9 g of the title compound to give a combined 45.4 g (61%) of the title compound.

iv. 4-N-Benzoyl-5-methyl-1-(2-fluoro-5-O-dimethoxytrityl-β-D-erythro-pentofuranosyl)cytosine 4-N-Benzoyl-5-methyl-1-(2-fluoro-β-D-erythro-pentofuranosyl)-cytosine (45.3 g, 0.124 mol) was dissolved in 250 ml dry pyridine and dimethoxytrityl chloride (46.4 g, 0.137 mol) was added. The reaction mixture was stirred at room temperature for 90 minutes and methanol (20 mL) was added. The mixture was concentrated in vacuo and partitioned between ethyl acetate (2×1 L) and saturated sodium bicarbonate (1 L). The ethyl acetate layers were combined, dried over magnesium sulfate and evaporated in vacuo. The resulting oil was dissolved in dichloromethane (200 mL) and purified by silica gel column chromatography using ethyl acetate/hexane/triethyl amine 50:50:1. The product fractions were pooled concentrated in vacuo dried to give 63.6 g (76.6%) of the title compound.

v. 4-N-Benzoyl-5-methyl-1-(2-fluoro-3-O-N,N-di-isopropyl-amino-2-cyanoethylphosphite-5-O-dimethoxytrityl-β-D-erythro-pentofuranosyl)cytosine 4-N-Benzoyl-5-methyl-1-(2-fluoro-5-O-dimethoxy-trityl-β-D-erythro-pentofuranosyl)-cytosine (61.8 g, 92.8 mmol) was stirred with dichloromethane (300 mL), 2-cyanoethyl N,N,N',N'-tetraisopropylphosphorodiamidite (40.9 mL, 0.130 mol) and diisopropylamine tetrazolide (4.76 g, 0.3 eq.) at room temperature for 17 hours. The mixture was washed with saturated sodium bicarbonate (1 L) and the bicarbonate solution was back extracted with dichloromethane (500 mL). The combined organic layers were washed with brine (1 L) and the brine was back extracted with dichloromethane (100 mL). The combined organic layers were dried over sodium sulfate, filtered, and concentrated to a vol of about 200 mL. Tht resulting material was purified by silica gel column chromatography using hexane/ethyl acetate/triethyl amine 60/40/1. The product fractions were concentrated in vacuo, dissolved in acetonitrile (500 ml), filtered, concentrated in vacuo, and dried to a foam. The foam was chopped and dried for 24 hours to a constant weight to give 72.4 g (90%) of the title compound. 1H NMR: (CDCl$_3$) δ 1.17-1.3 (m, 12 H, 4×CH$_3$), 1.5-1.6 (m, 2 H, 2×CH), 2.3-2.4 (t, 1 H, CH$_2$CN), 2.6-2.7 (t, 1 H, CH$_2$CN), 3.3-3.9 (m, 13 H, 2×CH$_3$OAr, 5' CH$_2$, CH$_2$OP, C-5 CH$_3$), 4.2-4.3 (m, 1 H, 4'), 4.3-4.7 (m, 1 H, 3'), 5.0-5.2 (m, 1 H, 2'), 6.0-6.2 (dd, 1 H, 1'), 6.8-6.9 (m, 4 H, DMT), 7.2-7.6 (m, 13 H, DMT, Bz), 7.82-7.86 (d, 1 H, C-6), 8.2-8.3 (d, 2 H, Bz). $^{31}$P NMR (CDCl$_3$); bs, 151.706; bs, 151.941.

EXAMPLE 5-c i. 1-(2,3-di-O-Butyltin-β-D-erythro-pentofuranosyl)-5-methyluridine

5-Methyluridine (7.8 g, 30.2 mmol) and dibutyltin oxide (7.7 g, 30.9 mmol) were suspended in methanol (150 mL) and heated to reflux for 16 hours. The reaction mixture was cooled to room temperature, filtered, and the solid washed with methanol (2×150 mL). The resulting solid was dried to give 12.2 g (80.3%) of the title compound. This material was used without further purification in subsequent reactions. NMR was consistent with structure.

ii. 1-(2-O-Propyl-β-D-erythro-pentofuranosyl)-5-methyluridine 1-(2,3-di-O-butyltin-β-D-erythro-pentofuranosyl)-5-methyluridine (5.0 g, 10.2 mmol) and iodopropane (14.7 g, 72.3 mmol) were stirred in DMF at 100° C. for 2 days. The reaction mixture was cooled to room temperature and filtered and concentrated. The residual DMF was coevaporated with acetonitrile. After drying the residue there was obtained 2.40 g (78%) of the title compound and the 3'-O-propyl isomer as a crude mixture. This material was used without further purification in subsequent reactions.

iii. 1-(2-O-Propyl-5-O-Dimethoxytrityl-β-D-erythro-pentofuranosyl)-5-methyluridine 1-(2-O-Propyl-β-D-erythro-pentofuranosyl)-5-methyluridine and the 3'-O-propyl isomer as a crude mixture (2.4 g, 8.4 mmol) was coevaporated with pyridine (2×40 mL) and dissolved in pyridine (60 mL). The solution was stirred at room temperature under argon for 15 minutes and dimethoxytrityl chloride (4.27 g, 12.6 mmol) was added. The mixture was checked periodically by tlc and at 3 hours was completed. Methanol (10 mL) was added and the mixture was stirred for 10 minutes. The reaction mixture was concentrated in vacuo and the resulting residue purified by silica gel column chromatography using 60:40 hexane/ethyl acetate with 1% triethylamine used throughout. The pooling and concentration of appropriate fractions gave 1.32 g (26%) of the title compound.

iv. 1-(2-O-Propyl-3-O-N,N-Diisopropylamino-2-cyanoethyl-phosphite-5-O-Dimethoxytrityl-β-D-erythro-Pentofuranosyl)-5-methyluridine 1-(2-O-Propyl-5-O-dimethoxytrityl-β-D-erythro-pentofuranosyl)-5-methyluridine (50.0 g, 86 mmol), 2-cyanoethyl-N,N,N',N'-tetra-isopropylphosphorodiamidite (38 mL, 120 mmol), and diisopropylamine tetrazolide (4.45 g, 25.8 mmol) were dissolved in dichloromethane (500 mL) and stirred at room temperature for 40 hours. The reaction mixture was washed with saturated sodium bicarbonate solution (2×400 mL) and brine (1×400 mL). The aqueous layers were back extracted with dichloromethane. The dichloromethane layers were combined, dried over sodium sulfate, filtered, and concentrated in vacuo. The resultant residue was purified by silica gel column chromatography using ethyl acetate/hexane 40:60 and 1 triethylamine. The appropriate fractions were pooled, concentrated, and dried under high vacuum to give 43 g (67%).

v. 1-(2-O-Propyl-3-O-acetyl-5-O-dimethoxytrityl-β-D-erythro-pentofuranosyl)-5-methyluridine 1-(2-O-Propyl-5-dimethoxytrityl-β-D-erythro-pentofuranosyl)-5-methyluridine (10.0 g, 16.6 mmol) was dissolved in pyridine (50 mL) and acetic anhydride (4.7 ml, 52.7 mmol) was added. The reaction mixture was stirred for 18 hours and excess acetic anhydride was neutralized with methanol (10 mL). The mixture was concentrated in vacuo and the resulting residue dissolved in ethyl acetate (150 mL). The ethyl acetate was washed with saturated NaHCO$_3$ (150 mL) and the saturated NaHCO$_3$ wash was back extracted with ethyl acetate (50 mL). The ethyl acetate layers were combined and concentrated in vacuo to yield a white foam 11.3 g. The crude yield was greater than 100% and the NMR was consistent with the expected structure of the title compound. This material was used without further purification in subsequent reactions.

EXAMPLE 5-d i. 1-(2-O-Propyl-3-O-acetyl-5-O-dimethoxytrityl-β-D-erythro-pentofuranosyl)-4-triazolo-5-methylpyrimidine Triazole (10.5 g, 152 mmol) was dissolved in acetonitrile (120 ml) and triethylamine (23 mL) with stirring under anhydrous conditions. The resulting solution was cooled in a dry ice acetone bath and phosphorous oxychloride (3.9 mL, 41 mmol) was added slowly over a period of 5 minutes. The mixture was stirred for an additional 10 minutes becoming a thin slurry indicative of product formation. 1-(2-O-Propyl-3-O-acetyl-5-O-dimethoxytrityl-β-D-erythro-pentofuranosyl)-5-methyluridine (11.2 g, 165 mmol) was dissolved in acetonitrile (150 mL) and added to the slurry above, maintaining dry ice acetone bath temperatures. The reaction mixture was stirred for 30 minutes and then allowed to warm to room temperature and stirred for an additional 2 hours. The mixture was placed in a freezer at 0° C. for 18 hours and then removed and allowed to warm to room temperature. Tlc in ethyl acetate/hexane 1:1 of the mixture showed complete conversion of the starting material. The reaction mixture was concentrated in vacuo and redissolved in ethyl acetate (300 mL) and extracted with saturated sodium bicarbonate solution (2×400 mL) and brine (400 mL). The aqueous layers were back extracted with ethyl acetate (200 mL). The ethyl acetate layers were combined, dried over sodium sulfate, and concentrated in vacuo. The crude yield was 11.3 g (95%). The NMR was consistent with the expected structure of the title compound. This material was used without further purification in subsequent reactions.

ii. 1-(2-O-Propyl-5-O-dimethoxytrityl-β-D-erythro-pentofuranosyl)-5-methylcytidine 1-(2-O-Propyl-3-O-acetyl-5-O-dimethoxytrityl-β-D-erythro-pentofuranosyl)-4-triazolo-5-methylpyrimidine (11.2 g, 16.1 mmol) was dissolved in liquid ammonia (50 mL) in a 100 mL bomb at dry ice acetone temperatures. The bomb was allowed to warm to room temperature for 18 hours and then recooled to dry ice acetone temperatures. The bomb contents were transferred to a beaker and methanol (50 mL) was added. The mixture was allowed to evaporate to near dryness. Ethyl acetate (300 mL) was added and some solid was filtered off prior to washing with saturated sodium bicarbonate solution (2×250 mL). The ethyl acetate layers were dried over sodium sulfate, filtered, combined with the solid previously filtered off, and concentrated in vacuo to give 10.1 g of material. The crude yield was greater than 100% and the NMR was consistent with the expected structure of the title compound. This material was used without further purification in subsequent reactions.

iii. 1-(2-O-Propyl-5-O-dimethoxytrityl-β-D-erythro-pento-furanosyl)-4-N-benzoyl-5-methylcytidine 1-(2-O-Propyl-5-O-dimethoxytrityl-β-D-erythro-pentofuranosyl)-5-methylcytidine (7.28 g, 10.1 mmol) and benzoic anhydride (4.5 g, 20 mmol) were dissolved in DMF (60 mL) and stirred at room temperature for 18 hours. The reaction mixture was concentrated in vacuo and redissolved in ethyl acetate (300 mL). The ethyl acetate solution was washed with saturated sodium bicarbonate solution (2×400 mL), dried over sodium sulfate, filtered, and concentrated in vacuo. The residue was purified by silica gel column chromatography using ethyl acetate/hexane 1:2 and 1% triethylamine. The appropriate fractions were pooled, concentrated, and dried under high vacuum to give 5.1 g (59% for 4 steps starting with the 1-(2-O-propyl-dimethoxytrityl-β-D-erythro-pentofuranosyl)-5-methyluridine).

iv. 1-(2-O-Propyl-3-O-N,N-diisopropylamino-2-cyanoethyl-phosphite-5-O-dimethoxytrityl-β-D-erythro-pentofuranosyl)-4-N-benzoyl-5-methylcytidine 1-(2-O-Propyl-5-O-dimethoxytrityl-β-D-erythro-pentofuranosyl)-4-N-benzoyl-5-methylcytidine (5.0 g, 7 mmol), 2-cyanoethyl-N,N,N',N'-tetra-isopropylphosphorodiamidite (3.6 mL, 11.3 mmol), and diisopropylaminotetrazolide (0.42 g, 2.4 mmol) were dissolved in dichloromethane (80 mL) and stirred at room temperature for 40 hours. The reaction mixture was washed with saturated sodium bicarbonate solution (2×40 mL) and brine (1×40 mL). The aqueous layers were back extracted with dichloromethane. The dichloromethane layers were combined, dried over sodium sulfate, filtered, and concentrated in vacuo. The resultant residue was purified by silica gel column chromatography using ethyl acetate/hexane 40:60 and 1% triethylamine. The appropriate fractions were pooled, concentrated, and dried under high vacuum to give 7.3 g (98%).

EXAMPLE 5-e i. 2'-O-Methyl-5-methyluridine

Procedure 1:

Crude 2,2'-anhydro-5-methyluridine (10.0 g, 0.0416 mol) (Example 2-a) was dissolved in methanol (80 mL) in a stainless steel bomb (100 mL capacity). Trimethyl borate (5.6 mL, 0.049 mol) was added (Note 1). The bomb was sealed and placed in an oil bath at 150° C. which generated a pressure of about 5 atm. After 40 h, the bomb was cooled in ice, opened and the contents concentrated under reduced pressure to a tan foam, 12 g. NMR of the crude was consistent with the product contaminated with impurities in the starting material and a trace of thymine and starting material (Note 2). The crude product was used as is for the next step.

The trialkyl borates can be conveniently generated by adding solutions (eg 1 M in THF) of borane to the desired alcohol and allowing the resulting hydrogen gas to evolve.) The nucleoside can be purified at this point by column chromatography using a gradient of methanol in ethyl acetate (0-10%) and crystallizing the product from absolute ethanol to give white needles, mp 192-193° (mp 197-198°). Literature reference for the melting point of this compound is contained in E. Ootsuka, H. Inoue, Japanese Patent 89-85456, Apr. 4, 1989.

Procedure 2:

Pure 2,2'-anhydro-5-methyluridine (1.0 g, 4.16 mmol) and trimethylborate (0.56 mL, 4.9 mmol) was dissolved in methanol (20 mL) in a stainless steel bomb (100 mL). The bomb was placed in an oil bath at 150° C. After 80 h, TLC indicating the reaction to be mostly complete. The solvent was removed yielding a white foam. NMR indicated product to starting material ratio of 93:7 with no other impurities noted. The residue was purified by silica gel column chromatography using a methanol gradient in ethyl acetate (0-10%) yielding 850 mg (75%) of pure product and 250 mg of still contaminated product. An analytically pure sample was prepared for NMR. $^1$H NMR (DMSO-$d_6$): δ 1.79 (s, 3H, 5-CH$_3$), 3.35 (s, 3H, OCH$_3$), 3.5-3.7 (m, 2H, H-5'), 3.7-3.9 (m, 2H, H-3',4'), 4.15 (m, 1H, H-2'), 5.17 (m, 2H, 3',5'-OH), 5.87 (d, J=5 Hz, 1H, H-1'), 7.80 (s, 1H, H-6), 11.37 (br s, 1H, N—H). Anal. Calcd for $C_{11}H_{16}N_2O_6$ (272.26): C, 48.52; H, 5.92; N, 10.29. Found: C, 48.56; H, 5.88; N, 10.22.

Procedure 3:

The same as described for procedure 2 except 30 mg of sodium bicarbonate was added to the reaction (to match the sodium content of the crude anhydro) which allowed the reaction to be complete in 24 h. Ammonium chloride (50 mg) was added to neutralize the base and the solution was stripped to dryness. NMR of the crude indicated three minor nucleoside impurities (total about 6%). After a similar column and then crystallizing the residue from methanol/ethyl acetate, there remained 850 mg of first crop material and 120 mg of second crop material both with 2-3% of unknown nucleoside impurities for a still contaminated yield of 85%.

ii. 5'-O-Dimethoxytriphenylmethyl-2'-O-methyl-5-methyl-uridine

Crude 2'-O-methyl-5-methyl uridine (12 g) was coevaporated in pyridine (2×50 mL) and dissolved in dry pyridine (50 mL). Dimethoxytriphenylmethyl chloride (18.1 g, 0.054 mol) was added. the flask was stoppered and allowed to stand for 45 min at room temperature. Methanol (10 mL) was added to quench the reaction and the solution was concentrated under reduced pressure to an oil. The residue was partitioned between ethyl acetate (2×400 mL) and saturated sodium bicarbonate solution (500 mL). The organic layers were combined, dried (sodium sulfate), filtered and concentrated to a yellow foam. The foam was dissolved in methylene chloride (60 mL) and put onto a silica gel column (300 g) and eluted with ethyl acetate-hexanes-triethylamine, 60:40:1. The product containing fractions were combined, concentrated and coevaporated with dry acetonitrile (2×50 mL). The resulting residue was dried at 1 mm Hg for 24 h to a crisp white foam, 17.0 g (60.4% in three steps from 5-methyluridine).

EXAMPLE 5-f i. 2,3,5-Tri-O-benzoyl-2-thio-5-methyluridine

In a 250 ml 3 neck round bottomed flask 1-O-acetyl-2,3,5-tri-O-benzoyl ribose (0.500 g, 1 mmol) and 5-methyl-2-thiouracil (0.156 g, 1.1 mmol) was dried under vacuum overnight. These components were dissolved in 10 mL of dry acetonitrile and heated to 80° C. To this warm solution was added N-O-bis(trimethylsilyl)acetamide (0.509 g, 2.5 mmol) and the reaction stirred for 1 hr at 80° C. The reaction mixture was removed from the heat and allowed to cool to room temperature, and trimethyl silyl triflate (0.334 g, 1.5 mmol) was added dropwise. The reaction mixture was then heated to 50° C. and stirred for 4 hours. The reaction mixture was checked by TLC using ethyl acetate/hexane 1:1, which showed the reaction had gone to completion. The solution was cooled to room temperature and partitioned between 50 mL of dichloromethane and 50 mL of saturated sodium bicarbonate solution. The aqueous phase was extracted two more times with dichloromethane and the organic layers combined, dried with magnesium sulfate and concentrated to a pale yellow foam. This foam was used without further purification.

ii. 2-Thio-5-methyluridine

The crude 2,3,5-tri-O-benzoyl-2-thio-5-methyl uridine (20 g, 37 mmoles) was dissolved in 500 mL of methanol. To this solution was added sodium methoxide (2.0 g, 37 mmoles) and the reaction stirred for 2 hours. The reaction was checked by TLC using ethyl acetate/hexane 1:1 and ethyl acetate/methanol 9:1, which showed the reaction had gone to completion. Dowex 50 H$^+$ resin was added until the solution was neutral by pH paper and the resin filtered. The resin was then washed with 100 ml of additional methanol and the combined filtrates were concentrated to give the title compound 8.5 g, (84%) as a pale yellow foam.

EXAMPLE 5-g

2'-O-Methyl-5-methyl-2-thiouridine

To a stirred solution of 5-methyl-2-thiouridine (0.500 g, 1.8 mmol) in DMF (10 ml) is added dibutyltin oxide (0.500 g, 2.0 mmol), tetrabutyl ammonium iodide (0.738 g, 2 mmol), and methyl iodide (1.022 g, 7.2 mmol). The reaction flask is sealed and heated at 50° C. for 16 hours. The mixture is cooled and another portion of methyl iodide is added (1.022 g, 7.2 mmol) and the reaction heated for an additional 16 hours. At the end of this time, the reaction mixture is cooled to room temperature and diluted with methylene chloride and chromatographed using a methylene chloride/methanol gradient. The appropriate fractions are collected and concentrated to give 2'-O-methyl-5-methyl-2-thiouridine.

EXAMPLE 5-h

2'-O-Propyl-5-methyl-2-thiouridine

The title compound is prepared as per the procedures of Example 5-g by substituting propyl iodide (1.22 g, 7.2 mmoles) in place of methyl iodide.

Example 5-i i. 2'-O-phthalimidopropyl-5-methyl-2-thiouridine

The title compound was prepared as per the procedures of Example 5-g by substituting bromo-propyl phthalimide (0.67 g, 2.5 mmoles) in place of methyl iodide, with an additional (0.300 g) added on the second day.

ii. 5'-O-Dimethoxytrityl-2'-O-propylamine-5-methyl-2-thiouridine

2'-O-Phthalimidopropyl-5-methyl-2-thiouridine (2.6 g, 3.6 mmol) was dissolved in dry pyridine and co-evaporated twice. The resulting foam was dissolved in 25 mL of dry pyridine and dimethoxy-trityl chloride (1.8 g, 5.5 mmol) was added followed by 4,4-dimethylaminopyridine (0.050 g, 0.4 mmol). The reaction was allowed to stir overnight at room temperature. To the reaction mixture was added 1 mL of methanol. The solution was partitioned between 75 mL of saturated sodium bicarbonate and 50 mL of chloroform. The aqueous layer was extracted with two additional portions of chloroform and the organic layers combined and dried with magnesium sulfate. After removal of the drying agent via filtration the filtrate was concentrated to an orange oil and purified by silica gel column chromatography using methanol/chloroform gradient with 0.5% pyridine added to neutralize the silica gel.

iii. 5'-O-Dimethoxytrityl-2'-O-propylamine-5-methyl-2S-toluoyl-2-thiouridine 5'-O-Dimethoxytrityl-2'-O-propylamine-5-methyl-2-thiouridine (1 g, 1.6 mmol) was dissolved in DMF and cooled to 0° C. To this solution was added triethyl amine (0.300 g, 3 m.mol) followed by toluoyl chloride (0.300 g, 1.92 mmol) dropwise over 5 minutes. The reaction was then allowed to warm to room temperature and stirred overnight, when complete the reaction was quenched with methanol and concentrated to an oil. The oil was then partitioned between 250 mL of a solution of saturated sodium bicarbonate/chloroform 1:1. The aqueous layer was extracted with two additional, 75 mL portions of chloroform, and the organic layers were dried and concentrated to an oil. The protected nucleoside was purified by silica gel column chromatography using a hexane/ethyl acetate gradient. The desired product was collected as a mixture of N-3 toluoyl and S-2 Toluoyl compounds. This mixture was used as is for the phosphyt-ilation procedure.

iv. 5'-O-Dimethoxytrityl-2'-O-propylamine-3'-O-[(N, N-diisopropylamino)-2-cyanoethoxyphosphite]-5-methyl-2-S-toluoyl-2-thiouridine To a solution of 5'-O-dimethoxytrityl-2'-O-propyl-amine-5-methyl-2-S-toluoyl-2-thiouridine (16.01 g, 22 mmol) and diisopropylethylamine (10 ml) in THF (200 ml), at 0° C., is added chloro-β-cyanoethoxy-N,N-diisopropylaminophosphine (5.6 ml, 25 mmol). The reaction mixture was stirred at room temperature for 20 hours. The reaction was concentrated and the residue purified by silica gel column chromatography. Elution with an ethyl acetate/hexane gradient while maintaining 1% triethylamine, pooling of appropriate fractions and evaporation will give the title compound.

EXAMPLE 5-j i. 2'-O-Aminopropyl-5-methyl-2-thiouridine

2'-O-Phthalimidopropyl-5-methyl-2-thiouridine (5.0 g, 15.8 mmol) is dissolved in 100 ml methanol in a 500 ml flask. Hydrazine (2.02 g, 63.2 mmol) is added and the mixture is heated to reflux (60-65° C.) with stirring for 14 hours. The solvent is evaporated in vacuo and the residue is dissolved in dichloromethane (150 ml) and extracted twice with an equal volume $NH_4OH$. The organic layer is evaporated to yield the crude product. NMR is used to assay product purity. The product is used in subsequent reactions without further purification.

ii. 2'-O-Trifluoroacetylaminopropyl-5-methyl-2-thiouridine

2'-O-Aminopropyl-5-methyl-2-thiouridine is dissolved in MeOH and 5 equivalents of triethylamine are added followed by 10 equivalents of ethyl trifluoroacetate. The title compound is isolated after purification.

iii. 2'-O-Trifluoroacetylaminopropyl-5'-O-dimethoxytrityl-5-methyl-2-thiouridine 2'-O-Trifluoroacetylaminopropyl-5-methyl-2-thiouridine (2.5 g, 3.6 mmol) is dissolved in dry pyridine and co-evaporated twice. The resulting yellow foam is dissolved in 25 mL of dry pyridine and dimethoxytrityl chloride (1.8 g, 5.5 mmol) is added followed by 4,4-dimethylaminopyridine (0.050 g, 0.4 mmol). The reaction is allowed to stir overnight at room temperature. To the reaction mixture is added 1 mL of methanol. The solution is partitioned between 75 mL of saturated sodium bicarbonate and 50 mL of chloroform. The aqueous layer is extracted with two additional portions of chloroform and the organic layers combined and dried with magnesium sulfate. After removal of the drying agent via filtration the filtrate is concentrated to an oil and purified by silica gel column chromatography using methanol/chloroform gradient with 0.5% pyridine added to neutralize the silica gel to give the title compound.

iv. 2'-O-Trifluoroacetylaminopropyl-3'-O-[(N,N-diisopropyl-amino)-2-cyanoethoxyphosphite]-5'-O-dimethoxytrityl-5-methyl-2-thiouridine The title compound is prepared as per the procedure of Example 5-i-iv. using the title compound from Example 5-j-iii.

EXAMPLE 5-k i. 5'-O-Dimethoxytrityl-2-thio-5-methyluridine

2-Thio-5-methyl uridine (1 g, 3.6 mmol) was dissolved in dry pyridine and co-evaporated twice. The resulting yellow foam was dissolved in 25 mL of dry pyridine and dimethoxytrityl chloride (1.8 g, 5.5 mmol) was added followed by 4,4-dimethylaminopyridine (0.050 g, 0.4 mmol). The reaction was allowed to stir overnight at room temperature. To the reaction mixture was added 1 mL of methanol. The solution was partitioned between 75 mL of saturated sodium bicarbonate and 50 mL of chloroform. The aqueous layer was extracted with two additional portions of chloroform and the organic layers combined and dried with magnesium sulfate. After removal of the drying agent via filtration the filtrate was concentrated to an orange oil and purified by silica gel column chromatography using methanol/chloroform gradient with 0.5% pyridine added to neutralize the silica gel.

ii. 5'-O-Dimethoxytrityl-3'-t-butyldimethylsilyl-5-methyl-2-thiouridine

5'-O-Dimethoxytrityl-2-thio-5-methyl uridine (1 g, 1.73 mmol) was co-evaporated twice with dry DMF and then dissolved in dry DMF and imidazole (0.141 g, 2.08 mmol) was added followed by (0.313 g, 2.08 mmol) of t-butyl-dimethylsilyl chloride. The reaction mixture was stirred overnight. The reaction was checked by TLC using ethyl acetate/hexane 1:1, which showed the reaction had gone to completion. The reaction mixture was then poured into 5% sodium bicarbonate and extracted 3 times with chloroform. The combined organic solution was dried with magnesium sulfate and concentrated to an oil. The resulting oil was purified by silica gel column chromatography using a methanol/chloroform gradient isolating separately the 2' and 3' silyl protected nucleoside.

iii. 5'-O-Dimethoxytrityl-3'-t-butyldimethylsilyl-2'-methanesulfonyl-5-methyl-2-thiouridine 5'-O-Dimethoxytrityl-3'-t-butyldimethylsilyl-5-methyl-2-thiouridine (1.0 g, 1.45 mmoles) was dissolved in pyridine and cooled to 0° C. To this solution was added methanesulfonyl chloride (0.183 g, 1.6 mmoles) dropwise. The reaction was then allowed to stir until complete by TLC. The reaction mixture is neutralized with methanol and concentrated to an oil. The title compound is used as is for further reactions.

iv. 5'-Dimethoxytrityl-3'-t-butyldimethylsilyl-2,2'-thio anhydro-5-methyl-2-thiouridine The mesylated nucleoside found in Example 5-k-iii is treated at room temperature with 5 equivalents of sodium methoxide and allowed to stir until complete formation of the thioanhydro product. The solution is then neutralized with Dowex 50W ($H^+$ form), the resin filtered off and the resulting solution concentrated to give the title compound.

v. 2'-Fluoro-3'-t-butyldimethylsilyl-5'-Dimethoxytrityl-5-methyl-2-thiouridine The thioanhydronucleoside found in Example 5-k-iv was dissolved in anhydrous dioxane. To this solution was added 6 equivalents of HF/Pyridine complex and the reaction stirred until complete by TLC. The reaction mixture is then poured over an equal volume of ice and calcium carbonate is added until neutral. The solids are filtered off and the filtrate is concentrated. The residue is purified by silica gel column chromatography to give the title compound.

vi. 2'-Fluoro-3'-O-[(N,N-diisopropylamino)-2-cyano-ethoxy-phosphite]-5'-dimethoxytrityl-5-methyl-2-thiouridine 2'-Fluoro-3'-t-butyldimethylsilyl-5'-dimethoxy-trityl-5-methyl-2-thiouridine is treated as per the procedure of Example 5-i-iv. to give the title compound.

EXAMPLE 6

Oligoribonucleotide Synthesis

Unsubstituted and substituted phosphodiester oligoribonucleotides, also identified herein as PO linked oligoribonucleotides, were synthesized on an automated DNA synthesizer (Applied Biosystems model 380B) using standard phosphoramidite chemistry with oxidation by iodine.

Phosphorothioate oligonucleotides, also identified herein as PS linked oligoribonucleotides, are synthesized as per the phosphodiester oligoribonucleotides except the standard oxidation bottle was replaced by 0.2 M solution of 3H-1,2-benzodithiole-3-one 1,1-dioxide in acetonitrile for the step wise thiation of the phosphite linkages. The thiation wait step was increased to 68 sec and was followed by the capping step. After cleavage from the CPG column and deblocking in concentrated ammonium hydroxide at 55° C. (18 hr), the oligonucleotides were purified by precipitating twice with 2.5 volumes of ethanol from a 0.5 M NaCl solution. Analytical gel electrophoresis was accomplished in 20% acrylamide, 8 M urea, 454 mM Tris-borate buffer, pH=7.0. Oligonucleotides and phosphorothioates were judged, based on polyacrylamide gel electrophoresis, to be greater than 80% full-length material.

Phosphinate oligoribonucleotides, also identified herein as PI linked oligoribonucleotides, are prepared as is described in U.S. Pat. No. 5,508,270, herein incorporated by reference.

Alkyl phosphonate oligoribonucleotides, also identified herein as PMe linked oligoribonucleotides, are prepared as is described in U.S. Pat. No. 4,469,863, herein incorporated by reference.

Phosphoramidite oligoribonucleotides, also identified herein as PN linked oligoribonucleotides, are prepared as is described in U.S. Pat. No., 5,256,775 or U.S. Pat. No. 5,366,878, herein incorporated by reference.

Alkylphosphonothioate oligoribonucleotides, also identified herein as MePS linked oligoribonucleotides, are prepared as is described in published PCT applications PCT/US94/00902 and PCT/US93/06976 (published as WO 94/17093 and WO 94/02499, respectively), herein incorporate by reference.

3'-Deoxy-3'-amino phosphoramidate oligoribonucleotide, also identified herein as 3'NPN linked oligoribonucleotides, are prepared as is described in U.S. Pat. No. 5,476,925, herein incorporated by reference.

Phosphotriester oligoribonucleotides, also identified herein as POMe linked oligoribonucleotides, are prepared as is described in U.S. Pat. No. 5,023,243, herein incorporated by reference.

Borano phosphate oligoribonucleotide, also identified herein as BP linked oligoribonucleotides, are prepared as is described in U.S. Pat. Nos. 5,130,302 and 5,177,198, both herein incorporated by reference.

EXAMPLE 7-a

Oligoribonucleoside Synthesis

Methylenemethylimino linked oligoribonucleosides, also identified herein as MMI linked oligoribonucleosides, methylenedimethylhydrazo linked oligoribonucleosides, also identified herein as MDH linked oligoribonucleosides, and methylenecarbonylamino linked oligonucleosides, also identified herein as amide-3 linked oligoribonucleosides, and methyleneaminocarbonyl linked oligonucleosides, also identified herein as amide-4 linked oligoribonucleosides as well as mixed backbone compounds having, as for instance, alternating MMI and PO or PS linkages are prepared as is described in U.S. Pat. Nos. 5,378,825, 5,386,023, 5,489,677 and in published PCT applications PCT/US92/04294 and PCT/US92/04305 (published as WO 92/20822 WO and 92/20823, respectively), herein incorporated by reference.

Formacetal and thioformacetal linked oligoribonucleosides, also identified herein as FA and TFA oligoribonucleosides, respectively, are prepared as is described in U.S. Pat. Nos. 5,264,562 and 5,264,564, herein incorporated by reference.

Ethylene oxide linked oligoribonucleosides, also herein identified as ETO linked oligoribonucleosides, are prepared as is described in U.S. Pat. No. 5,223,618, herein incorporated by reference.

EXAMPLE 7-b

PNA

Peptide Nucleic Acids (PNAs) are known per se and are prepared in accordance with any of the various procedures referred to in Peptide Nucleic Acids (PNA): Synthesis, Properties and Potential Applications, *Bioorganic & Medicinal Chemistry*, 1996, 4, 5-23. They may also be prepared in accordance with U.S. Pat. No. 5,539,083, corresponding to Ser. No. 08/200,742, filed Feb. 23, 1994, and assigned to the same assignee as this application. These references are herein incorporated by reference.

EXAMPLE 8

Chimeric phosphorothioate oligoribonucleotides, e.g. [2'-O-Me]/PS-[2'-OH]/PS.[-2'-O-Me]/PS oligoribonucleotide Chimeric oligoribonucleotides having 2'-O-alkyl phosphorothioate and 2'-OH phosphorothioate oligonucleotides segments were synthesized using an Applied Biosystems automated DNA synthesizer Model 380B, as above. Oligoribonucleotides were synthesized using the automated synthesizer and 5'-dimethoxytrityl-2'-tert-butyldimethylsilyl 3'-O-phosphoramidite for the RNA portion and 5'-dimethoxytrityl-2'-0-methyl-3'-O-phosphroamidite for 5' and 3' wings. The protecting groups on the exocyclic amines were, phenoxyacetyl for rA and rG, benzoyl for rC and 2'-O-methyl A and 2'-O-methyl C, and isobutyryl for 2'-O-methyl G. The standard synthesis cycle was modified by increasing the wait step after the delivery of tetrazole and base to 600 s repeated four times for RNA and twice for 2'-0-methyl. The fully protected oligoribonucleotide was cleaved from the support and the phosphate group was deprotected in 3:1 Ammonia/Ethanol at room temperature overnight then lyophilized to dryness. Treatment in methanolic ammonia for 24 hrs at room temperature was then done to deprotect all bases and sample was again lyophilized to dryness. The pellet was resuspended in 1M TBAF in THF for 24 hrs at room temperature to deprotect the 2' positions. The reaction is then quenched with 1M TEAA and the sample is then reduced to ½ volume by rotovac before being desalted on a G25 size exclusion column. The oligo recovered was then analyzed spectrophotometrically for yield and for purity by capillary electrophoresis and by mass spectrometer.

EXAMPLE 9

Chimeric "gapmer" oligoribonucleotides i. Chimeric methyl phosphonate oligoribonucleotide e.g., [2'-O-Me]/PMe.[2'-OH]/PMe.[-2'-O-Me]/PMe oligoribonucleotide In the manner of Example 8, using oligoribonucleotides of Example 6, a chimeric oligoribonucleotide having a methyl phosphonate backbone is prepared.

ii. Chimeric phosphoramidate oligoribonucleotide, e.g., [2'-O-Me]/PN.[2'-OH]/PN.[-2'-O-Me]/PN oligoribonucleotide.

In the manner of Example 8, using oligoribonucleotides of Example 6, a chimeric oligoribonucleotide having a phosphoramidate backbone is prepared.

iii. Chimeric phosphoramidate oligoribonucleotide, e.g., [2'-O-Me]/3'NPN.[2'-OH]/3'NPN.[-2'-O-Me]/3'NPN oligoribonucleotide In the manner of Example 8, using oligoribonucleotides of Example 6, a chimeric oligoribonucleotide having a 3'-deoxy-3'-amino phosphoramidate backbone is prepared.

iv. Chimeric phosphinate oligoribonucleotide, e.g., [2'-O-Me]/PI.[2'-OH]/PI.[-2'-O-Me]/PI oligoribonucleotide In the manner of Example 8, using oligoribonucleotides of Example 6, a chimeric oligoribonucleotide having a phosphinate backbone is prepared.

v. Chimeric alkylphosphonothioate oligoribonucleotide, e.g., [2'-O-Me]/MePS.[2'-OH]/MePS.[-2'-O-Me]/MePS oligoribonucleotide In the manner of Example 8, using oligoribonucleotides of Example 6, a chimeric oligoribonucleotide having a phosphonothioate backbone is prepared.

vi. Chimeric phosphorodithioate oligoribonucleotide, e.g., [2'-O-Me]/P2S.[2'-OH]/P2S.[-2'-O-Me]/P2S oligoribonucleotide In the manner of Example 8, using oligoribonucleotides of Example 6, a chimeric oligoribonucleotide having a phosphorodithioate backbone is prepared.

vii. Chimeric phosphoselenate oligoribonucleotide, e.g., [2'-O-Me]/PSe.[2'-OH]/PSe.[-2'-O-Me]/PSe oligoribonucleotide In the manner of Example 8, using oligoribonucleotides of Example 6, a chimeric oligoribonucleotide having a phosphoselenate backbone is prepared.

viii. Chimeric borano phosphate oligoribonucleotide, e.g., [2'-O-Me]/BP.[2'-OH]/BP.[-2'-O-Me]/BP oligoribonucleotide In the manner of Example 8, using oligoribonucleotides of Example 6, a chimeric oligoribonucleotide having a borano phosphate backbone is prepared.

ix. Chimeric methyl phosphotriester oligoribonucleotide, e.g., [2'-O-Me]/POME.[2'-OH]/POMe.[-2'-O-Me]/POMe oligoribonucleotide In the manner of Example 8, using oligoribonucleotides of Example 6, a chimeric oligoribonucleotide having a methyl phosphotriester backbone is prepared.

EXAMPLE 10

Chimeric Oligoribonucleosides i. Chimeric methylenemethyimino oligoribonucleoside, e.g. [2'-O-Me]/MMI.[2'-OH]/MMI.[-2'-O-Me]/MMI oligoribonucleoside In the manner of Example 8 using the chemistry of Example 7, a chimeric oligoribonucleoside having methylene-methylimino linkages throughout the oligoribonucleoside is prepared.

ii. Chimeric methylenedimethyhydrazo oligoribonucleoside, e.g. [2'-O-Me]/MDH.[2'-OH]/MDH.[-2'-O-Me]/MDH oligoribonucleoside In the manner of Example 8 using the chemistry of Example 7, a chimeric oligoribonucleoside having methylenedimethylhydrazo linkages throughout the oligoribonucleoside is prepared.

iii. Chimeric formacetal oligoribonucleoside, e.g. [2'-O-Me]/FA.[2'-OH]/FA.[-2'-O-Me]/FA oligoribonucleoside In the manner of Example 8 using the chemistry of Example 7, a chimeric oligoribonucleoside having formacetal linkages throughout the oligoribonucleoside is prepared.

iv. Chimeric thioformacetal oligoribonucleoside, e.g. [2'-O-Me]/TFA.[2'-OH]/TFA.[-2'-O-Me]/TFA oligoribonucleoside In the manner of Example 8 using the chemistry of Example 7, a chimeric oligoribonucleoside having thioformacetal linkages throughout the oligoribonucleoside is prepared.

v. Chimeric ethyleneoxide oligoribonucleoside, e.g. [2'-O-Me]/ETO.[2'-OH]/ETO.[-2'-O-Me]/ETO oligoribonucleoside In the manner of Example 8 using the chemistry of Example 7, a chimeric oligoribonucleoside having ethylene oxide linkages throughout the oligoribonucleoside is prepared.

vi. Chimeric methylenecarbonylamino oligoribonucleoside, e.g. [2'-O-Me]/amide-3.[2'-OH]/amide-3.[-2'-O-Me]/amide-3 oligoribonucleoside In the manner of Example 8 using the chemistry of Example 7, a chimeric oligoribonucleoside having amide-3 linkages throughout the oligoribonucleoside is prepared.

EXAMPLE 11

Chimeric oligoribonucleotides/oligoribonucleosides i. Methylenemethylimino/phosphorothioate chimera, e.g. [2'-0-Me]/PS.[2'-OH]/PS.[-2'-O-Me]/MMI oligoribonucleotide/oligoribonucleoside In the manner of Example 8 using the chemistry of Examples 6 and 7, a chimeric compound having both oligoribonucleotide and oligoribonucleoside segments is prepared. The chimeric compounds has methylenemethylimino linkages in one "wing" and phosphorothioate linkages in a central "gap" and in the other "wing."

ii. Chimeric Methyl phosphonate/methylenemethylimino/phosphorothioate oligoribonucleotide/oligoribonucleoside, e.g. [2'-O-Me]/PMe.[2'-OH]/PS.[-2'-O-Me]/MMI oligoribonucleotide/ oligoribonucleoside In the manner of Example 8 using the chemistry of Examples 6 and 7, a chimeric compound having both oligoribonucleotide and oligoribonucleoside portions is prepared. The chimeric compound has methylenemethylimino linkages in one "wing", a phosphorothioate linkages in a central "gap" and methyl phosphonate linkages in the other "wing."

iii. Chimeric methylenecarbonylamino/phosphorothioate/methylenecarbonylamino oligoribonucleotide/oligoribonucleoside, e.g. [2'-O-Me]/amide-3. [2'-OH]/PS.[-2'-O-Me]/amide-3 oligoribonucleotide/ oligoribonucleoside In the manner of Example 8 using the chemistry of Examples 6 and 7, a chimeric compound having both oligoribonucleotide and oligoribonucleoside segments is prepared. The chimeric compound has methylenecarbonylaimino linkages in both "wings" and phosphorothioate linkages in a central "gap."

iv. Chimeric methylenecarbonylamino/phosphorothioate/methylenemethylimino oligoribonucleotide/oligoribonucleoside, e.g. [2'-6-Me]/amide-3. [2'-OH]/PS.[-2'-O-Me]/MMI oligoribonucleotide/ oligoribonucleoside In the manner of Example 8 using the chemistry of Examples 6 and 7, a chimeric compound having both oligoribonucleotide and oligoribonucleoside segments is prepared. The chimeric compound has methylenecarbonylaimino linkages in one "wing" segment, phosphorothioate linkages in a central "gap" segment and methylenecarbonylamino linkages in the other "wing" segment.

v. Methylenemethylimino/phosphodiester/phosphorothioate chimera, e.g. [2'-O-Me]/MMI-PO.[2'-OH]/ PS.[-2'-O-Me]/MMI-PO oligoribonucleotide/oligoribonucleoside In the manner of Example 8 using the chemistry of Examples 6 and 7, a chimeric compound having both oligoribonucleotide and oligoribonucleoside segments is prepared. The chimeric compounds has alternating methylene-methylimino and phosphodiester linkages in its "wing" segments and phosphorothioate linkages in its central "gap" segment.

EXAMPLE 12

Chimeric "end" gapped phosphorothioate oligoribonucleotides i. "3'-End" gapped phosphorothioate chimera, e.g. [2'-O-Me]/PS.[2'-OH]/PS oligoribonucleotide In the manner of Example 8 a chimeric compound having an "open gap" segment at its 3' terminus," a "wing" segment at its 5' terminus and phosphorothioate linkages through out is prepared.

ii. "5'-End" gapped phosphorothioate chimera, e.g. [2'-OH]/PS.[2'-O-Me]/PS oligoribonucleotide In the manner of Example 8 a chimeric compound having an "open gap" segment at its 5' terminus," a "wing" segment at its 3' terminus and phosphorothioate linkages through out is prepared.

iii. "3'-End" gapped phosphorothioate chimera, e.g. [2'-F]/PS.[2'-OH]/PS oligoribonucleotide In the manner of Example 8, a chimeric compound having an "open gap" at its 3' terminus", 2'-fluoro nucleosides in its 5' "wing" segment, 2'-OH nucleosides in its open "gap" segment and phosphorothioate linkages through out is prepared.

EXAMPLE 13

Chimeric oligoribonucleotides with Uniform Backbone Linkages and Variable nucleoside Subunits i. Chimeric 2'-O-ethyl oligoribonucleotide, e.g., [2'-O-Et]/PS.[2'-OH]/PS.[2'-O-Et]/PS oligoribonucleotide In the manner of Example 8 a chimeric compound having 2'-O-ethyl nucleosides in its "wing" segments, 2'-OH nucleosides in its "gap" segment and phosphorothioate linkages throughout is prepared.

ii. Chimeric 2'-O-propyl oligoribonucleotide, e.g., [2'-O-Pr]/PS.[2'-OH]/PS.[2'-O-Pr]/PS oligoribonucleotide In the manner of Example 8 a chimeric compound having 2'-O-propyl nucleosides in its "wing" segments, 2'-OH nucleosides in its "gap" segment and phosphorothioate linkages throughout is prepared.

iii. [2'-O-F]/PS.[2'-OH]/PS.[2'-O-F]/PS oligoribonucleotide

In the manner of Example 8 a chimeric compound having 2'-fluoro nucleosides in its "wings" segments, 2'-OH nucleosides in its "gap" segment and phosphorothioate linkages throughout is prepared.

iv. [2'-O-EtOMe]/PS.[2'-OH]/PS.[2'-O-EtOMe]/PS oligoribonucleotide

In the manner of Example 8 a chimeric compound having 2'-O-methoxyethyl nucleosides in its "wings" segments, 2'-OH nucleosides in its "gap" segment and phosphorothioate linkages through out is prepared.

v. [2'-O-EtOMe]/PS.[2'-OH]/PS.[2'-F]/PS oligoribonucleotide

In the manner of Example 8 a chimeric compound having 2'-O-methoxyethyl nucleosides in its 5' "wing" segment, 2'-OH nucleosides in its "gap" segment, 2'-fluoro nucleosides in its 3' "wing" segment, and phosphorothioate linkages through out is prepared.

vi. [2'-O-EtOMe]/PS.[2'-OH]/PS.[2'-O-Me]/PS oligoribonucleotide

In the manner of Example 8, a chimeric compound having 2'-O-methoxyethyl nucleosides in its 5' "wing" segment, 2'-OH nucleosides in its gap, 2'-O-methyl nucleosides in its 3' "wing" segment and phosphorothioate linkages through out is prepared.

EXAMPLE 14

Chimeric oligoribonucleotides Having Variable Backbone Linkages and Variable nucleosides i. [2'-O-Me]/PMe.[2'-OH]/PS.[2'-F]/PS oligoribonucleotide

In the manner of Example 8 using chemistries of Example 6, a chimeric compound having 2'-O-methyl nucleosides in its 5' "wing" segment, 2'-OH nucleosides in its "gap," 2'-O-fluoro nucleosides in its 3' "wing" segment, phosphorothioate linkages in the "gap" segment and the 3' "wing" segment and methyl phosphonate linkages in the 5' "wing" segment is prepared.

ii. [2'-O-Me]/PME.[2'-OH]/PS.[2'-Pr]/PI oligoribonucleotide

In the manner of Example 8 using chemistries of Example 6, a chimeric compound having 2'-O-methyl nucleosides in its 5' "wing" segment, 2'-OH nucleosides in its "gap," 2'-O-propyl nucleosides in its 3' "wing" segment, phosphorothioate linkages in the "gap" segment, methyl phosphonate linkages in 5' "wing" segment and phosphinate linkages in the 3' "wing" segment is prepared.

EXAMPLE 15

Chimeric oligoribonucleotides that Include Surrogate nucleosides i. Morpholino nucleoside Surrogate Containing oligoribonucleotide, e.g., [morpholino nucleoside Surrogate].[2'-OH]/PS.[morpholino nucleoside Surrogate] oligoribonucleotide In the manner of Examples 7 and 8, a chimeric compound having morpholino nucleosides prepared as per the teachings of U.S. Pat. No. 5,506,337 in its "wing" segments and 2'-OH nucleosides linked via phosphorothioate linkages in its "gap" segment is prepared.

ii. Cyclobutyl nucleoside Surrogate Containing oligoribonucleotide, e.g., [cyclobutyl nucleoside Surrogate]/PS.[2'-OH]/PS.[cyclobutyl nucleoside Surrogate]/PS oligoribonucleotide In the manner of Examples 7 and 8, a chimeric compound having cyclobutyl surrogate nucleosides prepared as per the teachings of U.S. Pat. No. 5,359,044 in its "wing" segments, 2'-OH nucleosides in its "gap" segment and phosphorothioate linkages through out is prepared.

iii. Pyrrolidine nucleoside Surrogate Containing oligoribonucleotide, e.g., [pyrrolidine nucleoside Surrogate]/PS.[2'-OH]/PS.[pyrrolidine Sugar]/PS oligoribonucleotide In the manner of Examples 7 and 8, a chimeric compound having pyrrolidine surrogate nucleosides prepared as per the teachings of U.S. Pat. No. 5,519,135 in its "wing" segments, 2'-OH nucleosides in its "gap" segment and phosphorothioate linkages through out is prepared.

iv. "3[1]-End" gapped PNA-phosphorothioate chimera, e.g. PNA.[2'-OH]/PS oligoribonucleotide In the manner of Example 8 in combination with the chemistry of Examples 7-b, a chimeric compound having an "open gap" at its 3' terminus" formed from 2'-OH nucleosides having phosphorothioate linkages and PNA surrogate nucleosides in the 5' "wing" segment, is prepared.

EXAMPLE 16

Chimeric oligoribonucleotides that Include nucleosides Having Modified Bases i. N-2 Modified Purine Containing oligoribonucleotide, e.g., [Mod-purine]/PS.[2'-OH]/PS.[Mod-purine]/PS oligoribonucleotide In the manner of Example 8, a chimeric compound having 4,7,10,13-tetraazahexadec-1-yl guanosine nucleosides prepared as per the teachings of U.S. Pat. No. 5,459,255 in its "wing" segments, 2'-OH nucleosides in its "gap" and phosphorothioate linkages through out is prepared.

ii. C-5 modified pyrimidine Containing oligoribonucleotide, e.g., [Mod-pyr]/PS.[2'-OH]/PS.[Mod-pyr]/PS oligoribonucleotide In the manner of Example 8, a chimeric compound having 5-propynyl pyrimidine nucleosides prepared as per the teachings of U.S. Pat. No. 5,484,908 in its "wing" segments, 2'-OH nucleosides in its "gap" segment and phosphorothioate linkages through out is prepared.

iii. N-2, C-6 Modified Purine Containing oligoribonucleotide, e.g., [Mod-purine]/PS.[2'-OH]/PS.[Mod-purine]/PS oligoribonucleotide In the manner of Example 8, a chimeric compound having 6-hydroxy-2-fluoro purine nucleosides prepared as per the teachings of U.S. Pat. No. 5,459,255 in its "wing" segments, 2'-OH nucleosides in its "gap" and phosphorothioate linkages through out is prepared.

iv. 2'-O-alkyl, C-5 Modified pyrimidine Containing oligoribonucleotide, e.g., [2'-O-Propyl-Mod-pyr]/PS.[2'-OH]/PS.[2'-O-propyl-Mod-pyr]/PS oligoribonucleotide In the manner of Example 8, a chimeric compound having 2'-O-propyl-5-methyl cytidine nucleosides in its "wing" segments, 2'-OH nucleosides in its "gap" segment and phosphorothioate linkages through out is prepared.

v. 2'-O-alkyl, N-2, C-5 Modified pyrimidine Containing oligoribonucleotide, e.g., [2'-O-propyl-Mod-pyr]/PS.[2'-OH]/PS.[2'-O-propyl-Mod-pyr]/PS oligoribonucleotide In the manner of Example 8, a chimeric compound having 2'-O-propyl-2-thio-5-methyl uridine nucleosides in its "wing" segments, 2'-OH nucleosides in its "gap" segment and phosphorothioate linkages through out is prepared.

vi. 2'-O-aminoalkyl, N-2, C-5 Modified pyrimidine Containing oligoribonucleotide, e.g., [2'-O-aminopropyl-Mod-pyr]/PS.[2'-OH]/PS.[2'-O-aminopropyl-Mod-pyr]/PS oligoribonucleotide In the manner of Example 8, a chimeric compound having 2'-O-aminopropyl-2-thio-5-methyl uridine nucleosides in its "wing" segments, 2'-OH nucleosides in its "gap" segment and phosphorothioate linkages through out is prepared.

vii. 2'-O-fluoro, N-2, C-5 Modified pyrimidine Containing oligoribonucleotide, e.g., [2'-O-fluoro-Mod-pyr]/PS.[2'-OH]/PS.[2'-O-fluoro-Mod-pyr]/PS oligoribonucleotide In the manner of Example 8, a chimeric compound having 2'-O-fluoro-2-thio-5-methyl uridine nucleosides in its "wing" segments, 2'-OH nucleosides in its "gap" segment and phosphorothioate linkages through out is prepared.

EXAMPLE 17

Cell Culture and Northern Blot Analysis of ras Target

T24 cells were maintained as monolayers in McCoys medium (GIBCO-BRL, Gaithersburg, Md.) supplemented with 10% fetal bovine serum and 100 units/ml penicillin. After treatment with oligomeric compounds for 24 hrs the cells were trypsinzed, centrifuged and total cellular RNA was isolated according to standard protocols (see Ausubel et al., *Current Protocols in Molecular Biology,* 1988, Wiley and Sons, New York, N.Y.). To quantify the relative abundance of Ha-ras mRNA, total RNA (10 ug) was transferred by northern blotting onto Bio-Rad Zeta probe membrane (Bio-Rad, Hercules, Calif.) and UV crosslinked (Stratalinker™, Stratagene, LaJolla, Calif.). Membrane bound RNA was hybridized to a $^{32}$P labeled 0.9 kb Ha-ras cDNA probe (Oncogene Science, Pasadena, Calif.) and exposure to XAR film (Kodak, Rochester, N.Y.). The relative amount of Ha-ras signal was determined by normalizing the Ha-ras signal to that obtained when the same membrane was stripped and hybridized with a probe for human glyceraldehyde 3-phosphate dehydrogenase (G3PDH, Clontech, Palo Alto, Calif.). Signals from northern blots were quantified using phosphoimager and image quant software (Molecular Dynamics, Sunnyvale, Calif.).

EXAMPLE 18

Compound Treatment of Cells

Cells growing in monolayer were washed once with warm PBS then Opti-MEM (GIBCO-BRL) medium containing Lipofectin (GIBCO-BRL) at a concentration of 5 ug/ml per 200 nM of oligo with a maximum concentration of 15 ug/ml was added. Oligomeric compounds were added and incubated at 37° C. for 4 hrs when the medium was replaced with full serum medium. After 24 hrs in the presence of the compound the cells were harvested and RNA prepared for further analysis.

EXAMPLE 19

RNase H Analysis

RNase H analysis was performed using 17 base oligoribonucleotides corresponding to bases (+23 to +47) of activated (codon 12 mutation) Ha-ras mRNA. 5' End labeled RNA (20 nM) was incubated with a 100-fold molar excess of the various test oligoribonucleotides in a reaction containing 20 mM Tris-Cl, pH 7.5, 100 mM KCl, 10 mM $MgCL_2$, 1 mM dithiothreitol, and 4 units of RNase inhibitor (Pharmacia, Newark, N.J.) in a final volume of 100 ul. The oligoribonucleotides were melted by heating to 95° C. for 5 minutes then allowed to cool slowly to room temperature in 2 liters bath of water 90° C. Duplex formation was confirmed by the shift in mobility between the single stranded end labeled sense RNA and the annealed duplex on non denaturing polyacrylamide gels. The resulting duplexes were tested as substrates for digestion by *E. coli* RNase H (USB, Cleveland, Ohio). 1 µl of a $1 \times 10^{-9}$ mg/ml solution of RNase H was added to 10 µl of the duplex reaction incubated at 37° C. for 30 minutes, the reaction was terminated by the addition of denaturing loading buffer and reaction products were resolved on a 12% polyacrylamide gel containing 7 M Urea and exposed to XAR film (Kodak).

EXAMPLE 20

Cell Free in vitro Nuclease Assay

Duplexes used in the cell free T24 extract experiments were annealed as described above with the exception that after formation of the duplex, the reaction was treated with 1 µl of a mixture RNase T and A (Ambion RPAII kit, Austin, Tex.) and incubated for 15 min at 37° C., and then gel purified from a nondenaturing 12% polyacrylamide gel. T24 cell nuclear and cytosolic fractions were isolated as described previously (Szyf, M., Bozovic, V., and Tanigawa, G., *J. Biol. Chem.,* 1991, 266, 10027-10030). Annealed duplexes (10 µl) were incubated with 3 µg of the T24 cytosolic extract at 37° C. The reaction was terminated by phenol/chloroform extraction and ethanol precipitated with the addition of 10 µg of tRNA as a carrier. Pellets were resuspended in 10 µl of denaturing loading dye, products were resolved on 12% denaturing acrylamide gels as described above. $^{32}$P-labeled 17-base RNA was hydrolysed by heating to 95° C. for 10 minutes in the presence of 50 mM $NaCO_3$ pH=9.0 to generate a molecular weight ladder.

EXAMPLE 21

Determination of 5' and 3' termini

Non-labeled duplex was treated with T24 extracts as done previously, half of this reaction was treated with calf intestinal phosphatase (CIP, Stratagene) and half was left untreated. The phosphatase was inactivated by heating to 95° C. and the reactions were extracted with phenol/chloroform and then precipitated in ethanol with glycogen as a carrier. The precipitates were then treated with T4 polynucleotide kinase (Stratagene) and $^{32}$P-γ-ATP (ICN, Irvine, Calif.). The samples were again extracted by phenol/chloroform and precipitated with ethanol, the products of the reaction were then resolved on a 12% acrylamide gel and visualized by exposure to XAR film. The 3'-terminus of the cleaved duplex was evaluated by the reaction of duplex digestion products with T4 RNA ligase (Stratagene) and $^{32}$P-pCp (ICN).

EXAMPLE 22

Chimeric 2'-methoxy oligoribonucleotides Mediate Digestion of Target RNA in T24 Cells Structure activity analyses of antisense oligonucleotides specific for codon 12 of the Ha-ras oncogene containing various 2'-sugar modifications were reported by Monia, et al., *J. Biol. Chem.*, 1992, 267, 19954-19962 and Monia et al., *J. Biol. Chem.*, 1993, 268, 14514-14522. In those reports, although the 2'-modified oligonucleotides hybridized with greater affinity to RNA than did unmodified 2'-deoxy oligos they were completely ineffective in inhibiting Ha-ras gene expression. The lack of activity observed with these 2'-modified oligos was directly attributed to their inability to create duplexes that could serve as substrates for degradation by RNase H. Following a similar protocol, stretches of ribonucleotides were introduced into the center of 17 base 2'-methoxy oligoribonucleotides targeting Ha-ras mRNA to form 2'-methoxy-2'-hydorxy-2'-methoxy phosphorothioate oligoribonucleotide "gapped" chimeric compounds that have varying ribonucleotide content in the central gap segment (see FIG. 1 for a representation of these compounds as well as their base sequence). When hybridized to their cellular target the resultant duplex consists of two stretches that are not targets for nucleolytic degradation (the 2'-methoxy "wings") and one 2'-hydroxyl oligoribonucleotide stretch that was found to be a target for a novel ribonuclease activity that recognizes RNA:RNA duplexes. T24 human bladder carcinoma cells were used that contain an activating G-T transversion mutation in the Ha-ras gene at the codon 12 position. The "gapped" chimeric compounds specific for this mutation were transfected into T24 cells growing in culture. After incubation with the compounds for 24 hrs, cells were harvested, total cytosolic RNA isolated and Northern blot analysis for Ha-ras mRNA levels performed. Fully modified 2'-methoxy oligonucleotides did not support nucleolytic cleavage of target mRNA and therefore did not lead to a reduction in steady state levels of Ha-ras mRNA even at the highest concentration tested (FIGS. 2A and 2B). An RNA gapmer oligonucleotide with only 3 ribonucleotides in the gap was also incapable of inducing nucleolytic cleavage of the target RNA (FIGS. 2C and 2D). However, T24 cells treated with RNA gapmer oligonucleotides containing 5, 7 and 9 ribonucleotides in the gap as well as a full phosphorothioate oligoribonucleotide molecule all displayed dose dependent reductions in Ha-ras steady state mRNA levels (FIGS. 3B-3D). T24 cells treated with a control 9 RNA gapmer oligonucleotide that contained four mismatched bases in its sequence did not show dose dependent reduction in Ha-ras mRNA suggesting that hybridization to the target RNA is essential for activity (FIG. 3E). The RNA gapmer compounds showed dose dependent inhibition of Ha-ras steady state mRNA levels.

The ability of the RNA gapmer compounds to reduce Ha-ras mRNA was dependent on the size of the RNA gap and thus the size of the RNA:RNA duplex formed in vivo. Treatment of cells with the 3 base RNA gapmer compounds resulted in no cleavage of the target whereas the 5, 7 and 9 base RNA gapmer compounds resulted in reduction in Ha-ras mRNA (FIG. 4). The fact that the RNA gapmer oligonucleotide containing 3 ribonucleotides in the gap was unable to induce reduction in target mRNA suggests that the activity involved requires a minimal RNA:RNA duplex region of at least four ribonucleotides for binding and cleavage of the target. Interestingly, chimeric DNA gapmer oligonucleotides that contain deoxynucleotides in the gap instead of ribonucleotides show the same minimal gap size requirements to form substrates for RNase H mediated degradation of the target mRNA (Crooke et al., *Annu. Rev. Pharmacol.*, 1996, 36, 107), suggesting that RNase H and the double stranded RNase activity described here may share some properties, although their substrates are clearly different.

A control 9 RNA gapmer compound that contains four mismatched bases in its sequence resulted in essentially no reduction in Ha-ras mRNA as expected as is shown in FIG. 3E. A full phosphorothioate oligoribonucleotide molecule had approximately the same activity as the 5 RNA gapmer oligo (FIG. 3D). This might have been due to the relative decrease in stability of the full oligoribonucleotide in vivo resulting from inactivation by single stranded ribonucleases, as 2'-methoxy phosphorothioate oligodeoxynucleotides are considerably more stable than phosphorothioate oligoribonucleotides. Crooke et al., *J. Pharmacol Exp. Ther.*, 1996, 277, 923-937. Treatment of T24 cells with the various oligonucleotides and various concentrations up to 800 nM was done in triplicate and quantification of Ha-ras mRNA levels indicate that at 600 nM the 5 gapmer reduces Ha-ras mRNA by 51%, the 7 gapmer by 49%, the 9 gapmer by 77% and the full ribonucleotide by 38% when compared to non treated controls. This suggests that RNA gapmer oligoribonucleotides protected by 2'-methoxy wings would be more potent molecules. As shown in this example, an endoribonuclease activity in T24 human bladder carcinoma cells recognizes the internal RNA:oligoribonucleotide portion of a chimeric duplex and reduced the target mRNA levels.

EXAMPLE 23

An Activity Present in T24 Cellular Extracts Induces Cleavage of Gapmer oligoribonucleotide:RNA Duplex within the Internal RNA:RNA Portion in vitro To further characterize the double-stranded RNA cleavage activity in T24 cells, T24 cellular extracts were prepared and tested for the ability to cleave the 9 gap oligoribonucleotide: RNA duplex in vitro. The 9 gap compound: $^{32}$P-end labeled RNA duplex was incubated with 3 µg of cytosolic extract at 37° C. for varying time periods as shown in FIG. 4, followed by phenol chloroform extraction ethanol precipitation and separation of the products on a denaturing gel. That this duplex was a substrate for digestion by an activity present in T24 extracts is shown by the loss of full length end labeled RNA and the appearance of lower molecular weight digestion products indicated by arrows in FIG. 4. In addition, the activity responsible for the cleavage of the duplex has specificity for the RNA:RNA portion of the duplex molecule, as indicated by the sizes of the cleavage products it produces (see the physical map of the $^{32}$P-end labeled RNA, far right in FIG. 4. RNase H cleavage of a 9 deoxynucleotide gap oligonucleotide:RNA duplex and cleavage of the 9 ribonucleotide gap oligoribonucleotide: RNA duplex by T24 cellular extracts appears to result in similar digestion products. This is seen by comparing the gels of FIGS. 4 and 5. Both activities displayed preferred cleavage sites near the 3' end of the target RNA in their respective duplexes which suggests that they may share binding as well as mechanistic properties. Cellular extracts prepared from human umbilical vein epithelial cells (HUVEC), human lung carcinoma (A549) and Hela cell lines all contained an activity able to induce cleavage of the 9 RNA gapmer:RNA target duplex in vitro.

EXAMPLE 24

Cleavage of Target RNA in Both Cytoplasmic and Nuclear Fractions of Cell Products The cellular distribution of the double stranded RNase activity described herein was further evaluated. Nuclear extracts were prepared from T24 cells and tested for the ability to digest the 9 RNA gapmer oligonucleotide:RNA duplex. Nuclear extracts prepared from T24 cells were able to degrade the target duplex, and the activity was found to be present in the nuclear fraction at comparable levels to that in the cytoplasmic fractions.

An RNA gapmer oligonucleotide was synthesized that contained phosphorothioate linkages throughout the entire length of the molecule. Since this results in increased stability to single stranded nucleases, it was reasoned that it would inhibit cleavage of the antisense strand by the dsRNase as well. Therefore, to determine if the activity described above can cleave both strands in a RNA duplex molecule, a 9 RNA gapmer antisense oligonucleotide that contained phosphorothioate linkages in the wings between the 2' methoxy nucleotides but had phosphodiester linkages between the nine ribonucleotides in the gap was synthesized. A duplex composed of this $^{32}$P-labeled 9 RNA gapmer phosphodiester/phosphorothioate oligonucleotide and its complementary oligoribonucleotide was tested as a substrate for double stranded RNase activity in T24 extracts. The activity was capable of cleaving the antisense strand of this duplex as well as the sense strand and the pattern of the digestion products indicated that cleavage was again restricted to the RNA:RNA phosphodiester portion of the duplex.

EXAMPLE 25

An RNA Gapmer oligonucleotide:RNA Duplex is not a Substrate for RNase H

Figure 5:
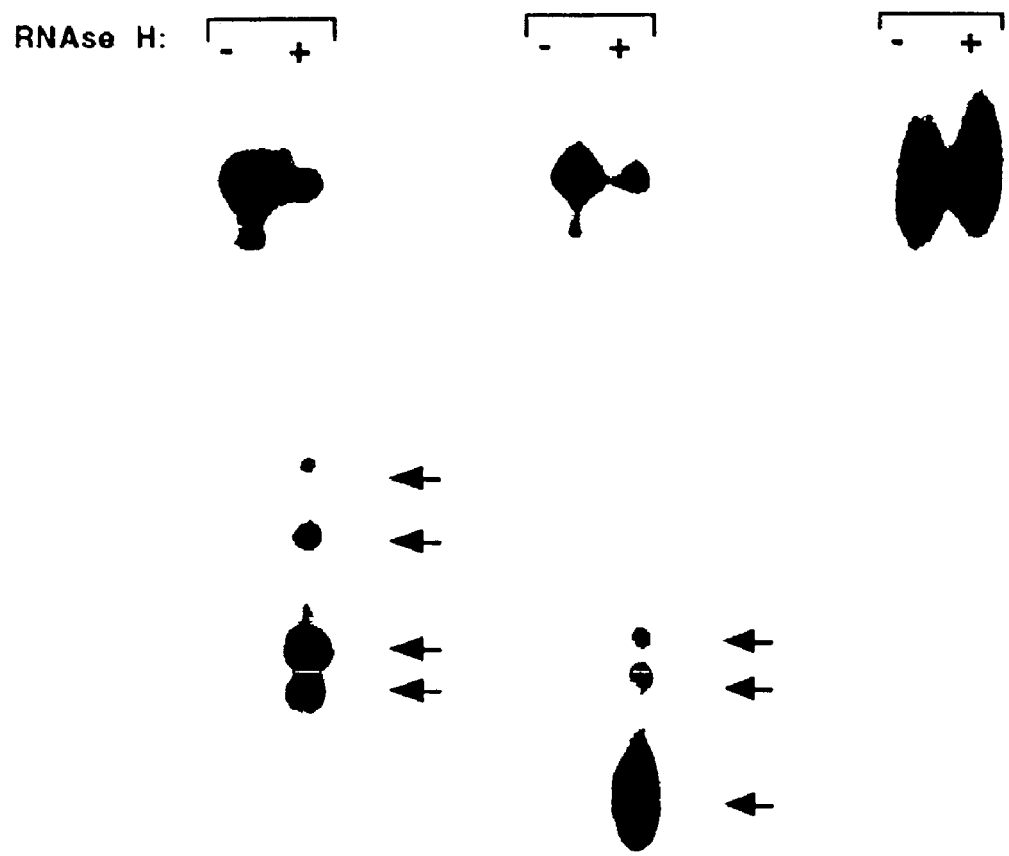
FIG. 5 shows the same 9 RNA gapmer oligonucleotide:RNA duplex as in FIG. 4, incubated with or without *E. coli* RNase H (− and +, respectively). The lack of digestion products indicates that this duplex is not a substrate for RNase H. Duplexes consisting of $^{32}$P-labeled RNA annealed to either a full oligodeoxynucleotide (middle panel) or 9 DNA gapmer oligonucleotide (left panel) are substrates for cleavage by RNase H and thus generate digestion products as expected (arrows).

To exclude the possibility that the cleavage shown in Example 23 might be due to RNase H, the ability of *E. coli* RNase H to cleave a 17 base pair duplex of the 9 gapmer oligoribonucleotide and its complementary 5' $^{32}$P-labeled RNA in vitro was tested. FIG. 5 shows the expected shift in electrophoretic mobility when duplexes were formed and analyzed on a native gel next to the single stranded $^{32}$P-end labeled RNA. As can be seen in FIG. 5 in the far right panel, the 9 Gapmer oligoribonucleotide:RNA duplex was not a substrate for RNase H cleavage as no lower molecular weight bands appeared when it was treated with RNase H. However, as expected a full deoxy oligonucleotide:RNA duplex was cleaved by RNase H under the same conditions, as is evident by the appearance of lower molecular species in the enzyme treated lane (FIG. 5, left panel). A duplex composed of a 9 gapmer DNA oligonucleotide and its complementary RNA was a substrate for RNase H cleavage. The fact that the RNase H cleavage sites in this particular duplex were localized to the DNA:RNA portions of the duplex further demonstrates that the RNA gapmer oligoribonucleotide:RNA duplex is not a substrate for RNase H digestion.

It is interesting to note that RNase H cleavage of the 9 DNA gapmer oligonucleotide:RNA duplex (FIG. 5, left panel) and cleavage of the 9 RNA gapmer oligonucleotide:RNA duplex by T24 cellular extracts resulted in similar digestion products (see FIG. 4). Both RNase H and the activity in T24 cells displayed the same preferred cleavage sites on their respective duplexes. Moreover, at this site, both the oligonucleotides were roughly comparable in potency. Cleavage was restricted to the 3' end of the target RNA in the region opposite either the DNA or RNA gap of the respective antisense molecule.

While not wishing to be bound by any particular theory, the immediately preceding result suggests that RNase H and the dsRNase of the invention may share binding as well as mechanistic properties. However, analysis of DNA and RNA gapmer oligonucleotides targeting four sites on c-Raf mRNA revealed that RNase H and the dsRNase activity described here clearly have different substrate specificities. "RNA-like" gapmer oligonucleotides targeted to the c-Raf mRNA were not able to induce reduction in mRNA whereas RNase H active oligodeoxynucleotides targeted to the same site were able to reduce target mRNA levels. To determine if the lack of cleavage induced by the four c-Raf "RNA gapmers" in T24 cells was due to possible sequence specificity or cleavage, the four c-Raf "RNA-like gapmers," the ras "RNA-like gapmer" and the corresponding "DNA-like gapmers" were prehybridized to $^{32}$P-labeled target oligoribonucleotides and incubated with T24 homogenates. The ras "RNA-like gapmer" supported cleavage of the ras target RNA almost as efficiently as the "DNA gapmer." However, only one of the "RNA-like gapmers" targeted to c-Raf segments (SEQ ID NO: 8) supported any cleavage and the rate of cleavage for the "RNA-like gapmer" was much slower than the comparable "DNA-like gapmer." Thus, in contrast to RNase H, the dsRNase displays considerable sequence specificity.

EXAMPLE 26

Nuclease Activity Generates 5'-phosphate and 3'-hydroxyl termini

To determine the nature of the 5' termini left by nuclease cleavage of the duplex in vitro, non-labeled duplex was incubated with T24 cellular extracts as previously described then reacted with T4 polynucleotide kinase and [$^{32}$P-γ-ATP] with or without prior treatment with calf intestinal phosphatase. Phosphatase treatment of the duplex products was seen to be essential for the incorporation of 32p label during the reaction with polynucleotide kinase, indicating the presence of a phosphate group at the 5' termini. The 3' termini were evaluated by the reaction of duplex digestion products with T4 RNA ligase and $^{32}$P-pCp. T4 RNA ligase requires a free 3'-hydroxyl terminus for the ligation of $^{32}$P-pCp. The ability of the duplex digestion products to incorporate $^{32}$P-pCp by T4 RNA ligase indicates the presence of 3'-hydroxyl groups.

EXAMPLE 27

Purification and Characterization of Double-Stranded ribonucleases from mammalian Tissues In order to determine if mammalian cells, other than cultured cell lines, contain double-strand RNase activity, and to provide a source from which such ribonucleases might be purified, the following efforts were undertaken to identify and purify dsRNases from rat liver homogenates.

EXAMPLE 27-a

Substrates and assays for dsRNases

In preliminary experiments, double-strand RNase activity was observed in rat liver homogenates, but the homogenates also displayed high levels of single-strand RNases that complicated analysis of the dsRNase activities because of cleavage of the oligoribonucleotide overhangs after cleavage by the dsRNases. To solve this problem, two additional substrates and a non-denaturing gel assay were used. The "sense" strand was an oligoribonucleotide having phosphodiester linkages in an eight-base gap with flanks having either (a) residues with phosphorothioate linkages or (b) 2'-methoxynucleosides with phosphorothioate linkages. The "antisense" strand in both substrates contained 2'-methoxy phosphorothioate wings on either side of an eight-base ribonucleotide gap having either phosphodiester or phosphorothioate linkages (Table 1). Such dsRNase substrates were more stable to exonuclease digestion than an oligoribonucleotide and substrates with both phosphorothioate linkages and 2'-methoxy nucleosides was extremely stable. These features are important because of the abundance of single-strand RNases relative to the double-strand RNase activity in the rat liver and supported the use of non-denaturing assays.

TABLE 1

Artificial Substrates for Mammalian dsRNases*

Ha-ras TARGETED SENSE/ANTISENSE OLIGONUCLEOTIDES

| | |
|---|---|
| SEQ ID NO:1 | 5'-GGG CGC CGU CGG UGU GG-3' |
| SEQ ID NO:2 | 3'-CCC GCG GCA GCC ACA CC-5' |

C-raf TARGETED SENSE/ANTISENSE OLGONUCLEOTIDES

| | |
|---|---|
| SEQ ID NO:3 | 5'-CCG AAU GUG ACC GCC UCC CG-3' |
| SEQ ID NO:4 | 3'-GGC UUA CAC UGG CGG AGG GC-5' |
| SEQ ID NO:5 | 5'-UCA AUG GAG CAC AUA CAG GG-3' |
| SEQ ID NO:6 | 3'-AGU UAC CUC GUG UAU GUC CC-5' |
| SEQ ID NO:7 | 5'-AAU GCA UGU CAC AGG CGG GA-3' |
| SEQ ID NO:8 | 3'-UUA CGU ACA GUG UCC GCC CU-5' |

Both rat liver cytosolic and nuclear extracts induced cleavage of the duplex substrate. Both extracts resulted in more rapidly migrating bands on native gel electrophoretic analyses. The cytosolic extract appeared to be more active than the nuclear extract. A double-strand RNase, RNase V1 (Pharmacia, Piscataway, N.J.) cleaved the substrate; T24 extracts also cleaved the substrate. Neither bacterial nor single-strand RNase cleaved the substrate, with the exception of RNase A, which at very high concentrations resulted in some cleavage. It is unclear whether that cleavage was due to a contaminating double-strand RNase or if RNase A can, under some conditions, cleave double-strand substrates.

EXAMPLE 27-b

Purification of dsRNases from Rat Liver Cytosolic and Nuclear Extracts

In order to purify the mammalian dsRNase identified herein, 0.5 kg of rat liver was homogenized in Bufferx[10 mM Hepes (ph 7.5), 25 mM KCl, 0.15 mM spermine, 0.5 mM spermidine, 1 mM EDTA, 2 M sucrose, 10% glycerol; all reagents from Sigma Chemical Co., St. Louis, Mo.] and centrifuged in a Beckman J2-21M centrifuge (Beckman, Fullerton, Calif.) at 10,000 rpm for 1.5 hours. The supernatant was precipitated with 40% ammonium sulfate (Sigma). All the dsRNase activity was recovered in the 40% ammonium sulfate precipitate. The pellet was resuspended in Buffer A [20 mM Hepes (ph 6.5), 5 mM EDTA, 1 mM DTT, 0.25 mM phenylmethylsulfonyl fluoride (PMSF), 0.1 M KCl, 5% glycerol, 0.1% NP40, 0.1% Triton X-100; all reagents from Sigma] and dialyzed to remove ammonium sulfate. Approximately 40 g of cytosolic extract were obtained from 0.5 kg liver.

A crude nuclear pellet, prepared as in the previous Examples, was resuspended and homogenized in Buffer Y [20 mM Hepes (ph 7.5), 0.42 M NaCl, 1.5 mM $MgCl_2$, 0.2 mM EDTA, 0.5 mM DTT, 0.5 mM PMSF, 25% glycerol]. The homogenate was centrifuged in a J2-21M centrifuge (Beckman) at 10,000 rpm for 1.5 hrs. The supernatant was precipitated with 70% ammonium sulfate. The pellet was resuspended in Buffer A and dialyzed. All the dsRNase activity was recovered in the 70% ammonium sulfate precipitate. Approximately 5 g Of nuclear extract were obtained from 0.5 kg liver.

Ion exchange chromatography was then performed in order to further purify the dsRNases of the invention. Nuclear and cytosolic extracts in Buffer A were loaded onto Hi-Trap columns (Pharmacia, Piscataway, N.J.) for FPLC. The extracts were eluted with a linear gradient of NaCl and samples were collected. The UV absorption at 257 ηM of the samples was determined. Samples were centrifuged at 8,000 g for 10 minutes, resuspended in Buffer A, concentrated in Ultrafree-centrifugal filter devices (Millipore, Bedford, Mass.) and analyzed for activity. The dsRNase activity eluted in fractions corresponding 300-450 mM NaCl. In contrast, the dsRNase activity in the nuclear extract eluted at 700-800 mM NaCl.

Fractions from the ion exchange chromatography were concentrated and subjected to size exclusion chromatography. Active samples from the ion exchange chromatography were pooled, applied to a TSK G-3000 column (TosoHaas, Mongomeryville, Pa.) and run with Buffer A containing 100 mM NaCl. Samples (200 to 400 ul) were collected and their UV absorption at 257 ηM was determined. Samples were concentrated using Ultrafree-15 centrifugal filter devices (Millipore) and then analyzed for activity.

Figure 6:
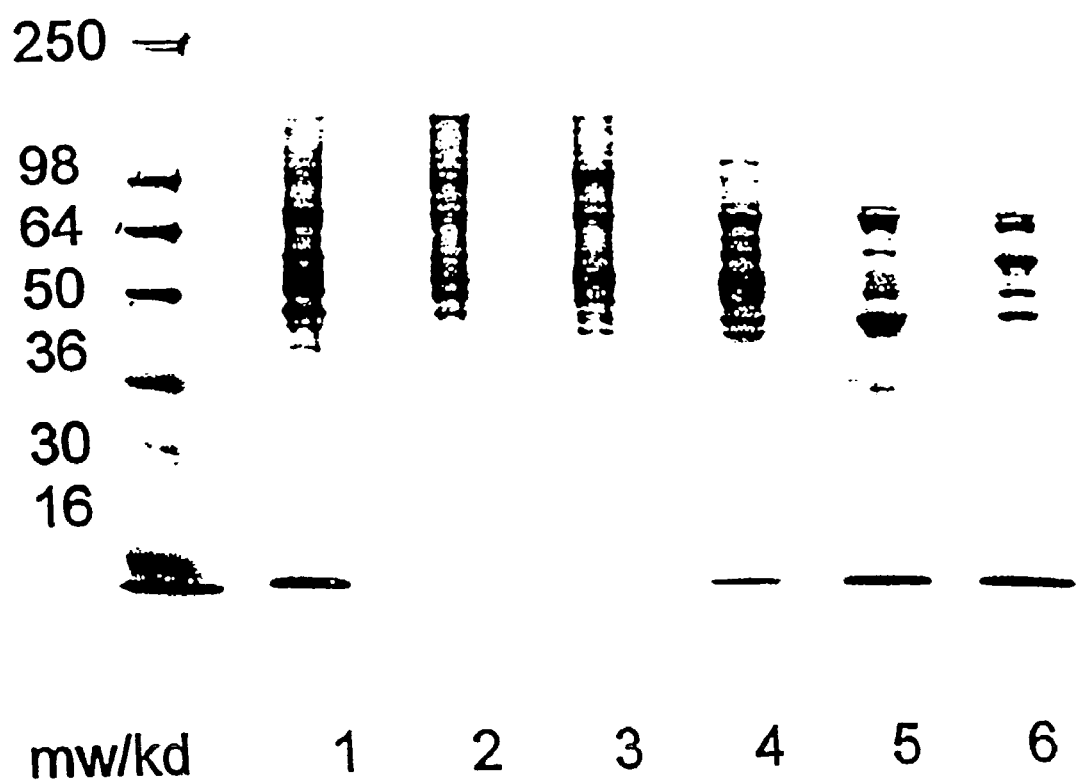
FIG. 6 depicts SDS-polyacrylamide gel electrophoretic analysis of the concentrated rat liver active fractions after size exclusion chromatography. MW, molecular weight markers in kilodaltons (kD). Fraction 3 (lane 4), having an apparent molecular weight in the range of about 35 to about 100 kD, with much of the material having an apparent molecular weight in the range 50 to about 80 kD, had the greatest amount of dsRNase activity.

FIG. 6 shows a polyacrylamide gel electrophoretic analysis of the concentrated active fractions after the ion-exchange chromatography, and the fractions from the size exclusion chromatography. The fraction with greatest dsRNase activity (lane 4, FIG. 6) had a molecular weight range of about 50 to about 80 kilodaltons, and a band at approximately 50 kilodaltons appeared to be enhanced on 12% polyacrylamide gel electrophoresis (PAGE) performed using precast gels (Novex, San Diego, Calif.).

Table 2 provides a summary of the purification and recovery of dsRNase activities from nuclear and cytosolic liver extracts.

TABLE 2

Summary of Purification of dsRNases from Rat Liver Homogenates

| Fraction | Protein (mg) | Total Activity (units*) | Specific Activity (unit/mg) | Purification Factor | Recovery (%) |
|---|---|---|---|---|---|
| Cytosolic extract | 30,000 | 1,020,000 | 34 | 1 | 100 |
| Ion Exchange (Pool) | 991 | 459,000 | 463 | 14 | 56 |
| Gel Filtration | 18.4 | 100,980 | 5,600 | 165 | 22 |

One unit is defined as the amount of sample required to digest 10 fMol dsRNA duplex in 15 minutes at 37° C. under the conditions described herein.

Purification of the dsRNase activities from liver nuclei and cytosol suggests that at least two dsRNases with differing properties are capable of cleaving double-strand RNA. The nuclear dsRNase eluted at higher NaCl concentrations from the ion exchange column than the cytosolic dsRNase. However, both require $Mg^{++}$ and cleave at several sites within the oligoribonucleotide gap. Both require a duplex substrate and can cleave oligoribonucleotides in a duplex that is made up of oligoribonucleotide "sense" and a 2' methoxy phosphorothioate chimeric "antisense" strand when the duplex has phosphorothioate or phosphorothioate-2' methoxy nucleoside wings.

Having (1) established a reproducible and activity-specific assay for, (2) determined several sources of and (3) achieved an adequate degree of purification of the dsRNases of the invention via the methods described above, the dsRNases are further purified by a variety of means. In all instances, the use of organic solvents is avoided as the dsRNases of the invention are unstable in acetonitrile or methanol (see below), and the assays described herein are used to evaluate the presence or absence of the desired dsRNase in a sample. Further purification steps may include, but are not limited to, the following means.

Several types of heparin columns have been used to purify a variety of ribonucleases. For example, Sepharose columns have been utilized in the purification of a sequence-specific ribonuclease from *Rana catesbeiana* (bullfrog) oocytes (Liao, *Nucl. Acids Res.*, 1992, 20, 1371), a ribonuclease from *Xenopus laevis* oocytes (Nitta et al., *Biol. Pharm. Bull.* (Jpn.), 1993, 16, 353), several ribonucleases from the thermophilic archaebacterium Sulfobus Solfataricus (Fusi et al., *Eur. J. Biochem.*, 1993, 211, 305), and a ribonuclease from human spleen (Yasuda et al., *Eur. J. Biochem.*, 1990, 191, 523).

Hydrophobic interaction chromatography is a powerful protein purification means which depends on strong salting-out salts to increase the hydrophobic interactions between the desired protein and a ligand therefor (Narhi et al., *Anal. Biochem.*, 1989, 182, 266). Hydrophobic interaction columns (HICs) have been used to purify ribonuclease A from undesired contaminants (Wu et al., *Methods in Enzymology*, 1996, 270, 27; Wetlaufer et al., *J. Chromatography*, 1986, 359, 55).

The dsRNases of the invention may also be further purified by hydroxyapatite chromatography (Kennedy, *Methods in Enzymology*, 1990, 182, 339). Endo- and exo-ribonuclease have been purified from *Trypanosoma brucei* using hydroxyapatite chromatography (Gbenle, *Exp. Parisitol.*, 1990, 71, 432; Gbenle, *Mol. Biochem. Parasitol.*, 1985, 15, 37).

RNA affinity columns may also be used to further purify the dsRNases of the invention. In particular, a commercially available double-stranded RNA affinity column (Pharmacia, Piscataway, N.J.) may be used. Alternatively, a column is prepared in which the matrix thereof comprises one or more of the dsRNase substrates of the invention (for details, see the following Example). Due to the relative sequence specificity of the dsRNase of the present invention, the latter type of affinity column may be preferable. In order to prevent degradation of the matrix of either type of double-stranded affinity matrix, samples comprising the dsRNases of the invention are treated in such a manner so as to limit the degradative capacity of the dsRNase without significantly altering its ability to bind to the double-stranded RNA substrate of the matrix. For example, the degradative activity of the dsRNase of the invention is inhibited in solutions lacking available $Mg^{++}$ due to, for example, the addition of appropriate chelating agents such as EDTA, or by addition of NaCl to a sample containing such dsRNases to a final concentration of at least 300 mM (see the following subsection).

Those skilled in the art will recognize that the above means, as well as others not herein described, will need to be optimized for optimal efficiency in purifying the dsRNases of the invention. For example, the selection of one or more of the above means as a further purification step, and of the order in which such means are applied, will effect the degree of purity and specific activity of the dsRNase so treated. However, such optimization is believed to be within the skill of the art given that the assays described herein can be readily utilized by a skilled artisan to determine the effect of further purification steps on the activity of the desired dsRNase. Other techniques known in the art, such as SDS-PAGE, can be used to determine the purity of samples subjected to the above purification means.

EXAMPLE 27-c

Characterization of Purified Mammalian dsRNases

The effects of various conditions on the dsRNase activity were evaluated using the active fractions after ion exchange chromatography. The dsRNase activity was demonstrable in Tris or phosphate buffers from about pH 7 to about pH 10. The dsRNase activity was not stable in solution in acetonitrile or methanol. Furthermore, the activity was inhibited by NaCl; dsRNase activity was inhibited by 30% at 10 mM NaCl, >60% at 100 mM NaCl and 100% at 300 mM NaCl. Heating for five minutes at 60° C., 80° C. or 100° C., inactivated the dsRNase. Optimum activity was seen in the temperature range of about 37° C. to about 42° C. At 25° C., the dsRNase activity was approximately 50% of that observed at 37° C. The dsRNase activity was inhibited at 10, 20 and 50 mM EDTA, but not at 5 mM, in agreement with its requirement for $Mg^{++}$, and was stable to multiple freeze/thaws.

EXAMPLE 28

Further Characterization of the dsRNase Cleavage Site Using Purified Rat dsRNase The purified dsRNases were used to characterize the site of cleavage in more detail. Because it was necessary to minimize any single-strand cleavage from occurring after endonuclease cleavage and during handling, particularly after denaturing of the duplex. Consequently, the most stable duplex substrate, i.e., one in which both strands of the duplex contained flanking regions comprised of 2' methoxy nucleosides and phosphorothioate linkages was used.

EXAMPLE 28-a $^{32}P$ Labeling of oligonucleotides

The sense oligonucleotide was 5'-end labeled with $^{32}P$ using $[g^{32}P]ATP$, T4 polynucleotide kinase, and standard procedures (Ausubel et al., 1989). The labeled oligonucleotide was purified by electrophoresis on 12% denaturing PAGE (Sambrook et al., 1989). The specific activity of the labeled oligonucleotide was approximately 5000 cpm/fmol.

EXAMPLE 28-b

Double-Strand RNA Digestion Assay

Oligonucleotide duplexes were prepared in 30 μL reaction buffer [20 mM tris-HCl (pH 7.5), 20 mM KCl, 10 mM $MgCl_2$, 0.1 mM DTT] containing 10 nM antisense oligonucleotide and $10^5$ cpm $^{32}P$ labeled sense oligonucleotide. Reactions were heated at 90° C. for 5 min and incubated at 37° C. for 2 h. The oligonucleotide duplexes were incubated in either unpurified and semipurified cellular extracts at a total protein concentration of 75 ug unpurified cytosolic extract, 60 ug unpurified nuclear extract, 5 ug ion exchange purified cytosolic fraction, 5 ug ion exchange purified nuclear fraction, or 0.5 ug ion exchange and gel filtration purified nuclear fraction. Digestion reactions were incubated at 37° C. for 0-240 min. Following incubation, 10 uL of each reaction was removed and quenched by addition of denaturing gel loading buffer [5 uL 8 M urea, 0.25% xylene cyanole FF, 0.25% bromphenol blue]. The reactions were heated at 95° C. for 5 min and resolved in a 12% denaturing polyacrylamide gel. The remaining aliquot was quenched in 2 uL native gel loading buffer [glycerol, 0.25% xylene cyanole FF. The reactions were resolved at 10° C. in a 12% native polyacrylamide gel containing 44 mM Tris-borate and 1 mM $MgCl_2$. Gels were analyzed using a Molecular Dynamics Phosphorimager.

Figure 7:
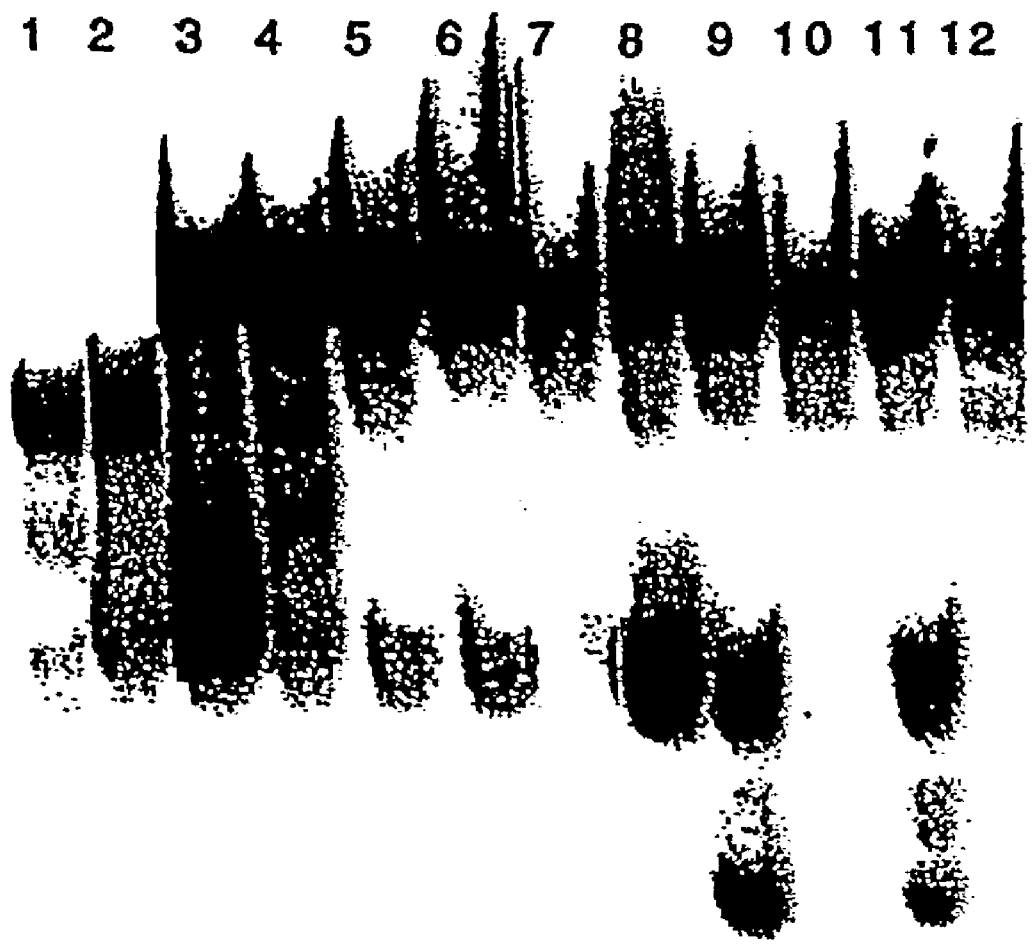
FIG. 7 shows analysis of products of digestion of dsRNAse substrates by native polyacrylamide gel electrophoresis. Antisense and sense oligonucleotides were preannealed and incubated with cellular extracts and purified dsRNases as described herein. Lane 1, untreated "sense" strand RNA; lane 2, "sense" strand RNA treated with 0.02 units RNase V1; remaining lanes: dsRNAse substrates treated with 0.02 (lane 3) and 0.002 (lane 4) units of RNase V1, with unpurified nuclear extract for 0 minutes (lane 5) or 240 minutes (lane 6), with unpurified nuclear extract for 240 minutes without $Mg^{++}$ (lane 7), with unpurified cytosolic extract for 240 minutes (lane 8), with ion exchange purified cytosolic extract for 240 minutes in the presence (lane 9) or absence (lane 10) of $Mg^{++}$, and with ion exchange/gel filtration purified cytosolic extract for 240 minutes in the presence (lane 9) or absence (lane 10) of $Mg^{++}$.

FIG. 7 displays the native gel results. Lane 1 shows the position at which the untreated $^{32}P$-labeled sense strand migrated in the native gel, and lane 2 shows "sense" strand RNA treated with 0.02 units RNase V1. In the remaining lanes, the results of treatment of dsRNAse substrates with 0.02 (lane 3) and 0.002 (lane 4) units of RNase V1, unpurified nuclear extract for 0 minutes (lane 5) or 240 minutes (lane 6), unpurified nuclear extract for 240 minutes without $Mg^{++}$ (lane 7), unpurified cytosolic extract for 240 minutes (lane 8), ion exchange purified cytosolic extract for 240 minutes in the presence (lane 9) or absence (lane 10) of $Mg^{++}$, and ion exchange/gel filtration purified cytosolic extract for 240 minutes in the presence (lane 9) or absence (lane 10) of $Mg^{++}$ are shown.

Figure 8:
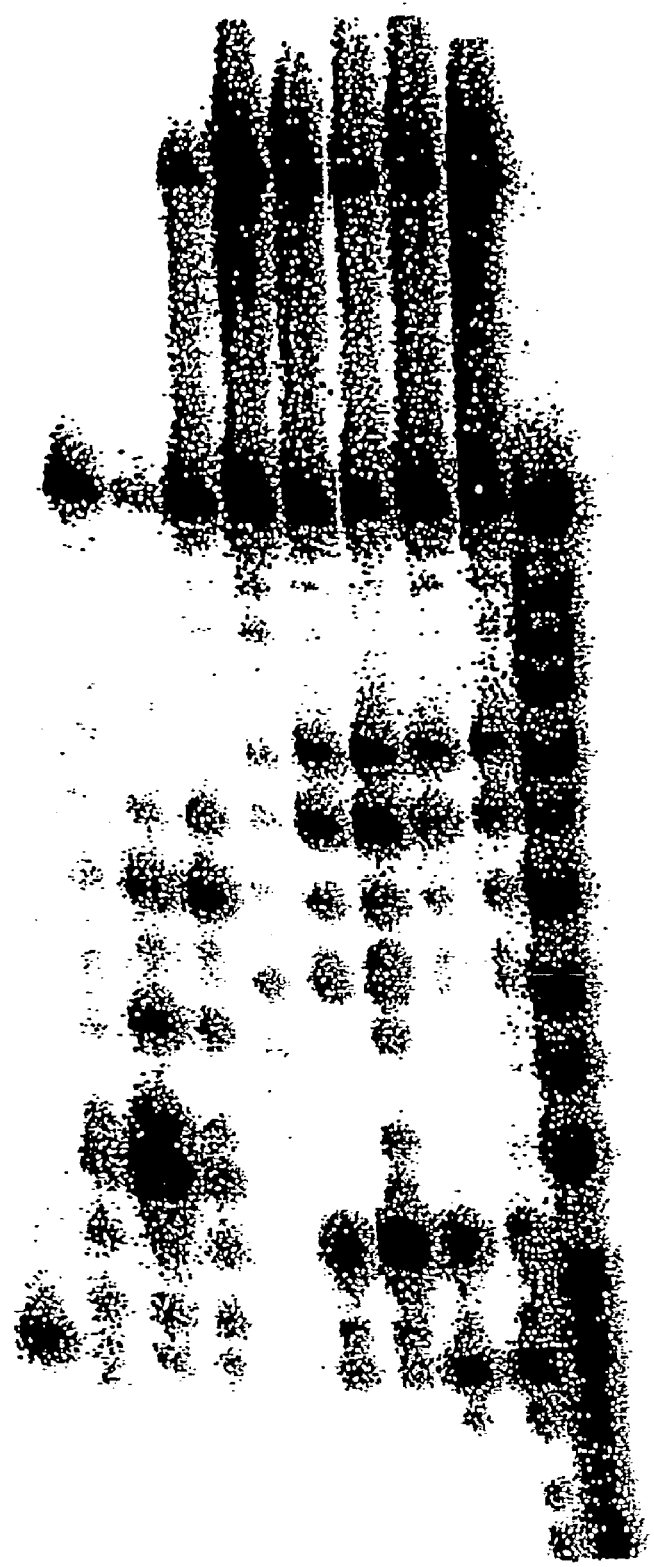
FIG. 8 shows analysis of products of digestion of dsRNAse substrates by denaturing polyacrylamide gel electrophoresis. Lane 1, "sense" strand RNA treated with $5\times10^{-3}$ units of RNase A; lane 2, "sense" strand RNA treated with 0.02 units RNase V1; lanes 3-9: dsRNAse products treated with 0.02 (lane 3) and 0.002 (lane 4) units of RNase V1, with unpurified nuclear extract for 0 minutes (lane 5) or 240 minutes (lane 6), with unpurified cytosolic extract for 240 minutes (lane 7), with ion exchange purified cytosolic extract for 240 minutes (lane 8), and with ion exchange/gel filtration purified cytosolic extract for 240 minutes (lane 9). Lane 10, base hydrolysis ladder.

FIG. 8 shows the results of analysis of products of digestion of dsRNAse substrates by denaturing polyacrylamide gel electrophoresis. Lane 1 shows "sense" strand RNA treated with $5\times10^{-3}$ units of RNase A, and lane 2 shows "sense" strand RNA treated with 0.02 units RNase V1. The remaining lanes show dsRNAse products treated with 0.02 (lane 3) and 0.002 (lane 4) units of RNase V1, with unpurified nuclear extract for 0 minutes (lane 5) or 240 minutes (lane 6), with unpurified cytosolic extract for 240 minutes (lane 7), with ion exchange purified cytosolic extract for 240 minutes (lane 8), and with ion exchange/gel filtration purified cytosolic extract for 240 minutes (lane 9). Lane 10 is an RNA base hydrolysis ladder included for sizing purpose. RNase V1 digestion of the single-strand substrate resulted in little degradation (lane 2). RNase V1 digestion of the duplex resulted in degradates reflecting cleavage at several sites within the gap (lanes 3 and 4). In lanes 4-9, the band at the top of the gel demonstrates that even after denaturation, some of the duplex remained annealed, reflecting the very high affinity of duplexes comprised to 2'-methoxy nucleosides. Lanes 6-9 show that both the nuclear and cytosolic ribonucleases cleaved the triplex substrate at several sites with the oligoribonucleotide gap and that the sites of degradation were different from those of RNase V1. The position of the degradates in lanes 6-9 is consistent with them being the 2' methoxy phosphorothioate flanking regions (wings).

EXAMPLE 29

RNA Affinity Columns and Methods of Purifying ribonucleases

Techniques for preparing nucleic acid affinity columns are known in the art (see, e.g., Kadonaga, *Methods in Enzymology,* 1991, 208, 10). Such affinity columns comprise a matrix comprising a nucleic acid substrate for a desired compound that binds the substrate either nonspecifically or in a sequence-specific manner. Initially utilized in the purification of DNA-binding proteins, RNA affinity columns have also been employed to purify RNA-binding proteins and ribonucleases (see, e.g., Prokipcak et al., *J. Biol. Chem.,* 1994, 269, 9261; Dake et al., *J. Biol. Chem.,* 1988, 263, 7691). A matrix comprising one or more dsRNase substrates of the invention has the advantage of providing a dsRNA substrate that is resistant to the action of single-stranded ribonuclease which are prevalent in many tissues and cells. Such a matrix also comprises a suitable solid support and a linker that provides a bridge between the solid support and the dsRNase substrate(s).

Suitable solid supports include, but are not limited to, graft polymers (U.S. Pat. No. 4,908,405 to Bayer and Rapp); polyacrylamide (Fahy et al., *Nucl. Acids Res.,* 1993, 21, 1819); polyacrylmorpholide, polystyrene and derivatized polystyrene resins (Syvanen et al., *Nucl. Acids Res.,* 1988, 16, 11327; U.S. Pat. Nos. 4,373,071 and 4,401,796 to Itakura), including amino methyl styrene resins (U.S. Pat. No. 4,507,433 to Miller and Ts'O); copolymers of N-vinylpyrrolidone and vinylacetate (Selinger et al., *Tetrahedron Letts.,* 1973, 31, 2911; Selinger et al., *Die Makromolekulare Chemie,* 1975, 176, 609; and Selinger, *Die Makromolekulare Chemie,* 1975, 176, 1611); TEFLON™ (Lohrmann et al., *DNA,* 1984, 3, 122; Duncan et al., *Anal. Biochem.,* 1988, 169, 104); controlled pore glass (Chow et al., *Anal. Biochem.,* 1988, 175, 63); polysaccharide supports such as agarose (Kadonaga, *Methods Enzymol.,* 1991, 208, 10; Arndt-Jovin et al., *Eur. J. Biochem.,* 1975, 54, 411; Wu et al., *Science,* 1987, 238, 1247; Blank et al., *Nucleic Acids Res.,* 1988, 16, 10283) or cellulose (Goldkorn et al., *Nucl. Acids Res.,* 1986, 14, 9171; Alberts et al., *Meth. Enzymol.,* 1971, 21, 198) or derivatives thereof, e.g., DEAE-cellulose (Schott, *J. Chromatogr.,* 1975, 115, 461) or phosphocellulose (Siddell, *Eur. J. Biochem.,* 1978, 92, 621; Bunemann et al., *Nucl. Acids Res.,* 1982, 10, 7163; Noyes et al., *Cell,* 1975, 5, 301; Bunemann et al., *Nucl. Acids Res.,* 1982, 10, 7181); dextran sulfate (Gingeras et al., *Nucl. Acids Res.,* 1987, 15, 5373); polypropylene (Matson et al., *Anal. Biochem.,* 1994, 217, 306), agarose beads (Kadonaga et al., *Proc. Natl. Acad. Sci. U.S.A.,* 1986, 83, 5889); latex particles (Kawaguchi et al., *Nucleic Acids Res.,* 1989, 17, 6229); nylon beads (Van Ness et al., *Nucl. Acids Res.,* 1991, 19, 3345); paramagnetic beads (Gabrielson et al., *Nucl. Acids Res.,* 1989, 17, 6253; Lund, et al., *Nucl. Acids Res.,* 1988, 16, 10861; Day et al., Biochem. J., 1991, 278, 735); silica gels (Yashima et al., *J. Chromatogr.,* 1992, 603, 111); derivatized forms of silica gels, polytetrafluoroethylene, cellulose or metallic oxides (U.S. Pat. No. 4,812,512 to Buendia); and art-recognized equivalents of any of the preceding solid supports; microtiter plates (Drmanac et al., *Science,* 1993, 260, 1649); crosslinked copolymers of N-vinylpyrrolidone, other N-vinyl-lactam monomers and an ethylenically unsaturated monomer having at least one amine or amine-displacable functionality as disclosed in U.S. Pat. No. 5,391,667. In one set of preferred embodiments, polystyrene or long chain alkyl CPG (controlled pore glass) beads are employed. In another set of preferred embodiments, microscopic glass slides are employed (Fodor et al., *Science,* 1991, 251, 767; Maskos et al., *Nucleic Acids Research,* 1992, 20, 1679; Guo et al., 1994, 22, 5456; Pease et al., *Proc. Natl. Acad. Sci. U.S.A.,* 1994, 91, 5022).

With regard to the linker, a variety of chemical linking groups or chains may be employed in the matrices of the invention. Any chemical group or chain capable of forming a chemical linkage between the solid support and the dsRNase substrate may be employed. A suitable linker has the preferred characteristic of non-reactivity with compounds introduced during the various steps of oligonucleotide synthesis. It will be appreciated by those skilled in the art that the chemical composition of the solid support and the dsRNase substrate will influence the choice of the linker. Many suitable linkers will comprise a primary amine group at either or both termini, as many chemical reactions are known in the art for linking primary amine groups to a variety of other chemical groups; however, other terminal reactive moieties are known and may be used in the invention. Suitable linkers include, but are not limited to, linkers having a terminal thiol group for introducing a disulfide linkages to the solid support (Day et al., *Biochem. J.,* 1991, 278, 735; Zuckermann et al., *Nucl. Acids Res.,* 15, 5305); linkers having a terminal bromoacetyl group for introducing a thiol-bromoacetyl linkage to the solid support (Fahy et al., *Nucl. Acids Res.,* 1993, 21, 1819); linkers having a terminal amino group which can be reacted with an activated 5' phosphate of an oligonucleotide (Takeda et al., *Tetrahedron Letts.,* 1983, 24, 245; Smith et al., *Nucl. Acids Res.,* 1985, 13, 2399; Zarytova et al., *Anal. Biochem.,* 1990, 188, 214); poly(ethyleneimine) (Van Ness et al., *Nucl. Acids Res.,* 1991, 19, 3345); acyl chains (Akashi et al., *Chem. Lett.,* 1988, 1093; Yashima et al., *J. Chromatogr.,* 1992, 603, 111); polyvinyl alcohol (Schott, *J. Chromatogr.,* 1975, 115, 461); alkyl chains (Goss et al., *J. Chromatogr.,* 1990, 508, 279); alkylamine chains (Pon et al., *BioTechniques,* 1988, 6, 768); biotin-avidin or biotin-streptavidin linkages (Kasher et al., *Mol. Cell. Biol.,* 1986, 6, 3117; Chodosh et al., *Mol. Cell. Biol.,* 1986, 6, 4723; Fishell et al., *Methods Enzymol.,* 1990, 184, 328); and art-recognized equivalents of any of the preceding linkers. In a preferred embodiment of the invention, an n-aminoalkyl chain is the linker. Methods of determining an appropriate (i.e., providing the optimal degree and specificity of hybridization between the sensor array and the target oligonucleotide) linker length are known in the art (see, e.g., Day et al., *Biochem. J.,* 1991, 278, 735).

What is claimed is:

1. A composition comprising a pharmaceutically acceptable diluent or carrier and a single-stranded oligomeric compound, wherein said compound:
   is 15 to 25 nucleoside subunits in length;
   specifically hybridizes with a preselected target RNA;
   comprises at least four consecutive nucleosides with 2'-hydroxyl-pentofuranosyl sugar moieties; and
   further comprises at least one sugar modified nucleoside subunit, wherein the modification improves affinity or specificity of said compound to said target RNA or increases resistance of said compound to single-stranded nucleases.

2. The composition of claim 1 wherein said compound further comprises at least one modified internucleoside linkage that is more stable to degradation than is a phosphodiester linkage.

3. The composition of claim 2 wherein said modified internucleoside linkage of said compound is phosphorothioate.

4. The composition of claim 3 wherein each internucleoside linkage of said compound is phosphorothioate.

5. The composition of claim 1 wherein said compound comprises four to twelve consecutive nucleosides each having a 2'-hydroxyl-pentofuranosyl sugar moiety.

6. The composition of claim 5 wherein said compound comprises five to nine consecutive nucleosides each having a 2'-hydroxyl-pentofuranosyl sugar moiety.

7. The composition of claim 1 wherein said compound comprises at least two nucleoside subunits with 2' modifications.

8. The composition of claim 7 wherein the 2' modifications of said compound are fluoro, $C_1$-$C_{20}$ alkoxy, $C_1$-$C_9$ aminoalkoxy, allyloxy, imidazolylalkoxy or polyethylene glycol.

9. The composition of claim 8 wherein at least one 2' modification of said compound is 2'-O-methoxyethyl.

10. The composition of claim 8 wherein at least one 2' modification of said compound is 2'-O-methyl.

11. The composition of claim 8 wherein at least one 2' modification of said compound is 2'-fluoro.

12. The composition of claim 1 wherein the modified nucleoside subunits of said compound are located at the 3' terminus or 5' terminus of the compound.

13. The composition of claim 1 wherein said compound comprises nucleoside subunits with 2'-hydroxyl-pentofuranosyl sugar moieties positioned between two segments of modified nucleoside subunits.

14. The composition of claim 1 wherein said compound is 100% complementary to said target RNA.

15. The composition of claim 1 wherein said compound is 17 to 20 nucleoside subunits in length.

16. A composition comprising a pharmaceutically acceptable diluent or carrier and a single-stranded oligomeric compound, wherein said compound:
  is 15 to 25 nucleoside subunits in length;
  is specifically hybridizable with a preselected target RNA;
  comprises at least one sugar modification; and
  comprises a plurality of nucleoside subunits with 2'-hydroxyl pentofuranosyl sugar moieties.

17. The composition of claim 16 wherein said sugar modification increases resistance of said compound to single-stranded nucleases or increases affinity of said compound to said target RNA.

18. The composition of claim 16 wherein at least one sugar modification is a 2'-substituted sugar modification.

19. The composition of claim 16 wherein at least one sugar modification is a 2'-alkoxy sugar modification.

20. The composition of claim 16 wherein at least one sugar modification is a 2'-methoxy sugar modification.

21. The composition of claim 16 wherein at least one sugar modification is a 2'-fluoro sugar modification.

22. The composition of claim 16 wherein at least one sugar modification is a 2'-O-methoxyethyl sugar modification.

23. The composition of claim 16 wherein said compound further comprises at least one modified internucleoside linkage.

24. The method of claim 23 wherein said modified internucleoside linkage is a phosphorothioate.

25. The method of claim 24 wherein each internucleoside linkage of said compound is phosphorothioate.

26. The composition of claim 16 wherein said compound is 100% complementary to said target RNA.

27. The composition of claim 16 wherein said compound is 17 to 20 nucleoside subunits in length.

* * * * *

SEQUENCE LISTING

```
<160> NUMBER OF SEQ ID NOS: 8
<210> SEQ ID NO 1
<211> LENGTH: 17
<212> TYPE: RNA
<213> ORGANISM: Artificial Sequence
<220> FEATURE:
<223> OTHER INFORMATION: Oligonucleotide

<400> SEQUENCE: 1
gggcgccguc ggugugg                                              17

<210> SEQ ID NO 2
<211> LENGTH: 17
<212> TYPE: RNA
<213> ORGANISM: Artificial Sequence
<220> FEATURE:
<223> OTHER INFORMATION: Oligonucleotide

<400> SEQUENCE: 2
ccacaccgac ggcgccc                                              17

<210> SEQ ID NO 3
<211> LENGTH: 20
<212> TYPE: RNA
<213> ORGANISM: Artificial Sequence
<220> FEATURE:
<223> OTHER INFORMATION: Oligonucleotide

<400> SEQUENCE: 3
ccgaauguga ccgccucccg                                           20

<210> SEQ ID NO 4
<211> LENGTH: 20
<212> TYPE: RNA
<213> ORGANISM: Artificial Sequence
<220> FEATURE:
<223> OTHER INFORMATION: Oligonucleotide

<400> SEQUENCE: 4
```

```
cgggaggcgg ucacauucgg                                              20

<210> SEQ ID NO 5
<211> LENGTH: 20
<212> TYPE: RNA
<213> ORGANISM: Artificial Sequence
<220> FEATURE:
<223> OTHER INFORMATION: Oligonucleotide

<400> SEQUENCE: 5
ucaauggagc acauacaggg                                              20

<210> SEQ ID NO 6
<211> LENGTH: 20
<212> TYPE: RNA
<213> ORGANISM: Artificial Sequence
<220> FEATURE:
<223> OTHER INFORMATION: Oligonucleotide

<400> SEQUENCE: 6
cccuguaugu gcuccauuga                                              20

<210> SEQ ID NO 7
<211> LENGTH: 20
<212> TYPE: RNA
<213> ORGANISM: Artificial Sequence
<220> FEATURE:
<223> OTHER INFORMATION: Oligonucleotide

<400> SEQUENCE: 7
aaugcauguc acaggcggga                                              20

<210> SEQ ID NO 8
<211> LENGTH: 20
<212> TYPE: RNA
<213> ORGANISM: Artificial Sequence
<220> FEATURE:
<223> OTHER INFORMATION: Oligonucleotide

<400> SEQUENCE: 8
ucccgccugu gacaugcauu                                              20
```